(12) United States Patent
Park et al.

(10) Patent No.: US 8,986,287 B2
(45) Date of Patent: Mar. 24, 2015

(54) ADJUSTABLE LAPAROSCOPIC INSTRUMENT HANDLE

(75) Inventors: Adrian E. Park, Crownsville, MD (US);
Brady R. Shirley, Lewisville, TX (US);
Daniel J. Triplett, Providence, UT (US);
Darin Ewer, Providence, UT (US)

(73) Assignees: Adrian E. Park, Crownsville, MD (US);
IMDS LLC, Providence, UT (US)

( * ) Notice: Subject to any disclaimer, the term of this patent is extended or adjusted under 35 U.S.C. 154(b) by 318 days.

(21) Appl. No.: 13/326,911

(22) Filed: Dec. 15, 2011

(65) Prior Publication Data

US 2012/0209254 A1 Aug. 16, 2012

Related U.S. Application Data

(60) Provisional application No. 61/442,510, filed on Feb. 14, 2011.

(51) Int. Cl.
*A61B 17/00* (2006.01)
*A61B 17/29* (2006.01)
*A61B 17/06* (2006.01)
*A61B 19/00* (2006.01)

(52) U.S. Cl.
CPC ....... *A61B 17/2909* (2013.01); *A61B 17/06061* (2013.01); *A61B 19/34* (2013.01); *A61B 2017/00424* (2013.01); *A61B 2017/291* (2013.01); *A61B 2017/292* (2013.01)
USPC ................................ 606/1; 606/130; 606/167

(58) Field of Classification Search
USPC ..................... 606/1, 130, 167–171, 205–209; 600/101, 104–106, 111, 14, 135–139, 600/160, 166

See application file for complete search history.

(56) References Cited

U.S. PATENT DOCUMENTS

| | | | |
|---|---|---|---|
| 4,950,273 A | 8/1990 | Briggs | |
| 5,174,300 A | 12/1992 | Smith | |
| 5,234,460 A * | 8/1993 | Stouder, Jr. | ................... 606/205 |
| 5,275,608 A | 1/1994 | Milder | |
| 5,282,800 A | 2/1994 | Foshee | |

(Continued)

FOREIGN PATENT DOCUMENTS

WO WO2004047653 6/2004

OTHER PUBLICATIONS

Amaral, Joseph; Ergonomic Evaluation of a New Rotating, Dual Position Laparoscopic Instrument Handle. Jun. 1994, #0-7803-2050.

(Continued)

*Primary Examiner* — Ahmed Farah
(74) *Attorney, Agent, or Firm* — Maywood IP Law; G. Jo Hays; David W. Meibos

(57) ABSTRACT

Instrument handles are adjustable relative to an end effector of the instrument. The handles may be releasably locked in selected positions and/or orientations relative to the end effector. When the lock is released, the handles may be moved to a different position and/or orientation relative to the end effector, and locked in place. The handles may pivot relative to the end effector around one or more joints. The handles may pivot about an axis of a hinge joint or a point of a ball and socket joint. The axis of the hinge joint may be aligned parallel or perpendicular to a center longitudinal axis of the end effector, or of a shaft between the handles and the end effector.

88 Claims, 90 Drawing Sheets

(56) References Cited

U.S. PATENT DOCUMENTS

| | | | |
|---|---|---|---|
| 5,308,358 A | 5/1994 | Bond | |
| 5,330,502 A | 7/1994 | Armstong | |
| 5,334,198 A | 8/1994 | Winter | |
| 5,336,238 A | 8/1994 | Holmes | |
| 5,342,391 A | 8/1994 | Foshee | |
| 5,350,391 A | 9/1994 | Iacovelli | |
| 5,368,606 A | 11/1994 | Petruschke | |
| 5,374,277 A | 12/1994 | Hassler | |
| 5,403,342 A | 4/1995 | Pasqualucci | |
| 5,472,451 A | 12/1995 | Hurley | |
| 5,482,197 A | 1/1996 | Sienkiewicz | |
| 5,484,095 A | 1/1996 | Green | |
| 5,499,992 A | 3/1996 | Meade | |
| 5,520,678 A | 5/1996 | Heckele | |
| 5,527,339 A | 6/1996 | Koscher | |
| 5,549,637 A | 8/1996 | Crainich | |
| 5,556,416 A * | 9/1996 | Clark et al. | 606/205 |
| 5,564,615 A | 10/1996 | Hibner | |
| 5,575,799 A | 11/1996 | Bolanos | |
| 5,577,654 A | 11/1996 | Bishop | |
| 5,582,617 A | 12/1996 | Klieman | |
| 5,588,580 A | 12/1996 | Paul | |
| 5,588,581 A | 12/1996 | Hibner | |
| 5,601,224 A | 2/1997 | Hibner | |
| 5,603,723 A | 2/1997 | Aranyi | |
| 5,609,601 A | 3/1997 | Kolesa | |
| 5,626,587 A | 5/1997 | Sambi | |
| 5,634,584 A | 6/1997 | Okorocha | |
| 5,636,780 A | 6/1997 | Sienkiewicz | |
| 5,643,294 A | 7/1997 | Aranyi | |
| 5,645,561 A | 7/1997 | King | |
| 5,662,662 A | 9/1997 | Sambi | |
| 5,702,408 A | 12/1997 | Stefanchik | |
| 5,704,534 A | 1/1998 | Schulze | |
| 5,725,536 A | 3/1998 | Oberlin | |
| 5,743,456 A | 4/1998 | Nelson | |
| 5,746,759 A | 5/1998 | Meade | |
| 5,752,973 A | 5/1998 | Kieturakis | |
| 5,782,749 A * | 7/1998 | Riza | 600/117 |
| 5,797,536 A | 8/1998 | Graves | |
| 5,797,538 A | 8/1998 | Milliman | |
| 5,797,958 A | 8/1998 | Yoon | |
| 5,827,323 A | 10/1998 | Klieman | |
| 5,830,231 A | 11/1998 | Geiges | |
| 5,836,960 A | 11/1998 | Kolesa | |
| 5,868,785 A | 2/1999 | Orth | |
| 5,901,895 A | 5/1999 | Milliman | |
| 5,928,255 A | 7/1999 | Meads | |
| 5,954,731 A | 9/1999 | Yoon | |
| 5,976,121 A | 11/1999 | Matern | |
| 5,984,939 A | 11/1999 | Yoon | |
| 5,993,467 A * | 11/1999 | Yoon | 606/147 |
| 5,997,565 A * | 12/1999 | Inoue | 606/205 |
| 6,077,286 A * | 6/2000 | Cuschieri et al. | 606/170 |
| 6,250,532 B1 | 6/2001 | Sienkiewicz | |
| 6,261,307 B1 | 7/2001 | Yoon | |
| 6,436,122 B1 * | 8/2002 | Frank et al. | 606/208 |
| 6,540,737 B2 | 4/2003 | Frank | |
| 6,619,529 B2 | 9/2003 | Green et al. | |
| 6,644,532 B2 | 11/2003 | Sienkiewicz | |
| 6,666,854 B1 * | 12/2003 | Lange | 606/1 |
| 6,786,382 B1 | 9/2004 | Hoffman | |
| 6,877,647 B2 | 4/2005 | Sienkiewicz | |
| 6,936,061 B2 | 8/2005 | Sasaki | |
| 6,964,363 B2 | 11/2005 | Heuil | |
| 6,981,628 B2 | 1/2006 | Wales | |
| 7,055,731 B2 | 6/2006 | Weisenburgh | |
| 7,111,769 B2 | 9/2006 | Swayze | |
| 7,159,750 B2 | 1/2007 | Racenet | |
| 7,213,736 B2 | 5/2007 | Wales | |
| 7,246,734 B2 | 7/2007 | Shelton | |
| 7,296,724 B2 | 11/2007 | Sienkiewivz | |
| 7,328,828 B2 | 2/2008 | Ortiz | |
| 7,404,508 B2 | 7/2008 | Kline | |
| 7,404,509 B2 | 7/2008 | Ortiz | |
| 7,410,086 B2 | 8/2008 | Ortiz | |
| 7,419,080 B2 | 9/2008 | Kline | |
| 7,424,965 B2 | 9/2008 | Racenet | |
| 7,431,189 B2 | 10/2008 | Timperman | |
| 7,438,209 B1 | 10/2008 | Hess | |
| 7,441,684 B2 | 10/2008 | Timperman | |
| 7,441,685 B1 | 10/2008 | Boudreaux | |
| 7,448,525 B2 | 11/2008 | Timperman | |
| 7,494,039 B2 | 2/2009 | Racenet | |
| 7,506,790 B2 | 3/2009 | Shelton | |
| 7,510,107 B2 | 3/2009 | Timm | |
| 7,513,408 B2 | 4/2009 | Wales | |
| 7,568,603 B2 | 8/2009 | Gillum | |
| 7,584,880 B2 | 9/2009 | Racenet | |
| 7,588,176 B2 | 9/2009 | Timperman | |
| 7,597,230 B2 | 10/2009 | Racenet | |
| 7,604,151 B2 | 10/2009 | Hess | |
| 7,637,410 B2 | 12/2009 | Marczyk | |
| 7,644,848 B2 | 1/2010 | Doll | |
| 7,673,780 B2 | 3/2010 | Swayze | |
| 7,673,782 B2 | 3/2010 | Hess | |
| 7,674,255 B2 | 3/2010 | Braun | |
| 7,703,653 B2 | 4/2010 | Maffei | |
| 7,721,931 B2 | 5/2010 | Giordano | |
| 7,721,934 B2 | 5/2010 | Gillum | |
| 7,721,935 B2 | 5/2010 | Racenet | |
| 7,721,936 B2 | 5/2010 | Shalton | |
| 7,731,072 B2 | 6/2010 | Swayze | |
| 7,735,703 B2 | 6/2010 | Hess | |
| 7,740,159 B2 | 6/2010 | Timperman | |
| 7,753,904 B2 | 7/2010 | Swayze | |
| 7,758,608 B2 | 7/2010 | DiCesare | |
| 7,780,660 B2 | 8/2010 | Bourne | |
| D624,649 S | 9/2010 | Seeh | |
| 7,793,814 B2 | 9/2010 | Stearns | |
| 7,794,475 B2 | 9/2010 | Hess | |
| 7,799,028 B2 | 9/2010 | Solga | |
| 7,799,039 B2 | 9/2010 | Morgan | |
| 7,815,091 B2 | 10/2010 | Marczyk | |
| 7,819,298 B2 | 10/2010 | Tanguay | |
| 7,845,537 B2 | 12/2010 | Ouwerkerk | |
| 7,861,906 B2 | 1/2011 | Kolata | |
| 7,866,527 B2 | 1/2011 | Tanguay | |
| 7,922,739 B2 | 4/2011 | Downey | |
| 7,954,682 B2 | 6/2011 | Giordano | |
| 2001/0027312 A1 | 10/2001 | Bacher | |
| 2002/0055758 A1 | 5/2002 | Sasaki | |
| 2005/0103819 A1 | 5/2005 | Racenet | |
| 2006/0095074 A1 * | 5/2006 | Lee et al. | 606/205 |
| 2006/0190031 A1 | 8/2006 | Wales | |
| 2006/0226196 A1 | 10/2006 | Hueil | |
| 2006/0229665 A1 | 10/2006 | Wales | |
| 2006/0289602 A1 | 12/2006 | Wales | |
| 2007/0023477 A1 | 2/2007 | Whitman | |
| 2007/0084897 A1 | 4/2007 | Shelton | |
| 2007/0106317 A1 | 5/2007 | Shelton | |
| 2007/0175949 A1 | 8/2007 | Shelton | |
| 2007/0175951 A1 | 8/2007 | Shelton | |
| 2007/0175952 A1 | 8/2007 | Shelton | |
| 2007/0175953 A1 | 8/2007 | Shelton | |
| 2007/0175955 A1 | 8/2007 | Shelton | |
| 2007/0175958 A1 | 8/2007 | Shelton | |
| 2007/0175960 A1 | 8/2007 | Shelton | |
| 2007/0175962 A1 | 8/2007 | Shelton | |
| 2007/0175964 A1 | 8/2007 | Shelton | |
| 2007/0299469 A1 | 12/2007 | Carpenter | |
| 2008/0029570 A1 | 2/2008 | Shelton | |
| 2008/0029573 A1 | 2/2008 | Shelton | |
| 2008/0029574 A1 | 2/2008 | Shelton | |
| 2008/0029575 A1 | 2/2008 | Shelton | |
| 2008/0078800 A1 | 4/2008 | Hess | |
| 2008/0078802 A1 | 4/2008 | Hess | |
| 2008/0078803 A1 | 4/2008 | Shelton | |
| 2008/0078804 A1 | 4/2008 | Shelton | |
| 2008/0078806 A1 | 4/2008 | Omaits | |
| 2008/0078807 A1 | 4/2008 | Hess | |
| 2008/0078808 A1 | 4/2008 | Hess | |
| 2008/0167522 A1 | 7/2008 | Giordano | |
| 2008/0167644 A1 | 7/2008 | Shelton | |

(56) References Cited

U.S. PATENT DOCUMENTS

| | | |
|---|---|---|
| 2008/0167672 A1 | 7/2008 | Giordano |
| 2008/0296346 A1 | 12/2008 | Shelton |
| 2008/0300580 A1 | 12/2008 | Shelton |
| 2008/0308602 A1 | 12/2008 | Timm |
| 2008/0308603 A1 | 12/2008 | Shelton |
| 2009/0001121 A1 | 1/2009 | Hess |
| 2009/0001130 A1 | 1/2009 | Hess |
| 2009/0005807 A1 | 1/2009 | Hess |
| 2009/0005808 A1 | 1/2009 | Hess |
| 2009/0005809 A1 | 1/2009 | Hess |
| 2009/0209990 A1 | 8/2009 | Yates |
| 2009/0247994 A1 | 10/2009 | Bacher |
| 2009/0289096 A1 | 11/2009 | Shelton |
| 2009/0292282 A9 * | 11/2009 | Dycus .................... 606/51 |
| 2009/0312773 A1 | 12/2009 | Cabrera |
| 2010/0030018 A1 | 2/2010 | Fortier |
| 2010/0030218 A1 * | 2/2010 | Prevost .................... 606/80 |
| 2010/0032470 A1 | 2/2010 | Hess |
| 2010/0069942 A1 | 3/2010 | Shelton |
| 2010/0076260 A1 | 3/2010 | Taylor |
| 2010/0076474 A1 | 3/2010 | Yates |
| 2010/0076475 A1 | 3/2010 | Yates |
| 2010/0089970 A1 | 4/2010 | Smith |
| 2010/0089974 A1 | 4/2010 | Shelton |
| 2010/0133317 A1 | 6/2010 | Shelton |
| 2010/0179382 A1 | 7/2010 | Shelton |
| 2010/0193566 A1 | 8/2010 | Scheib |
| 2010/0193567 A1 | 8/2010 | Scheib |
| 2010/0193568 A1 | 8/2010 | Scheib |
| 2010/0193569 A1 | 8/2010 | Yates |
| 2010/0198220 A1 | 8/2010 | Boudreaux |
| 2010/0224669 A1 | 9/2010 | Shelton |
| 2010/0243706 A1 | 9/2010 | Cohen |
| 2010/0243709 A1 | 9/2010 | Hess |
| 2010/0305552 A1 | 12/2010 | Shelton |
| 2011/0024480 A1 | 2/2011 | Marczyk |
| 2011/0062211 A1 | 3/2011 | Ross |
| 2011/0068148 A1 | 3/2011 | Hall |
| 2011/0132962 A1 | 6/2011 | Hall |
| 2011/0155788 A1 | 6/2011 | Hillstead |

OTHER PUBLICATIONS

Buchel, D.; Ergonomics of Disposable Handles for Minimally Invasive Surgery. Sug. Endosc. (2010) 24:992-1004.

Matern, U.; MIS Instruments. Surgical Endoscopy, (199) 13; 756-762.

Matern, U.; Ergonomic Aspects of Five Different Types of Laparoscopic Instrument Handles Under Dynamic Conditions with respect to Specific Laparoscopic Tasks: An Electromyographic-Based Study. Surg. Endosc (2004) 18: 1231-1241.

Matern, U.; Instruments for Minnimally Invasive Surgery. Sug. Endosc (199) 13: 174-182.

Veelen, MA; Improved Phusical Ergonomics of Laparoscopic Surgery. Min Invas Ther & Allied Technology (2004) 13; 3 161-166.

Youssef, Yassar; Laparoscopic Cholecystectomy Poses Physical Injury Risk to Surgeon's: Analysis of Hand Technique and Standing Position. Surg. Endosc. (2011) 25: 2168-2174.

* cited by examiner

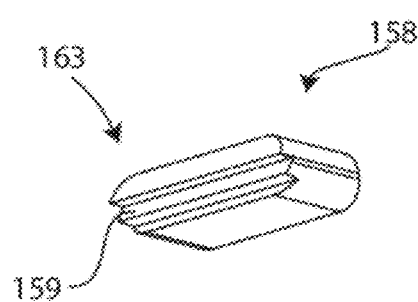
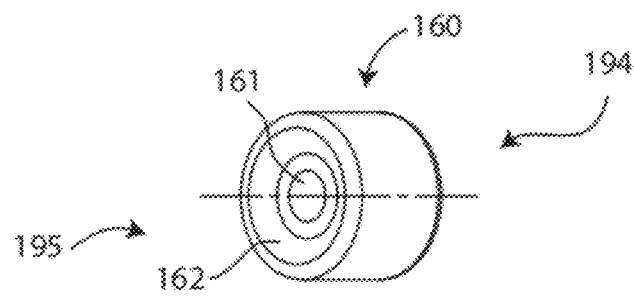
Fig. 9     Fig. 10
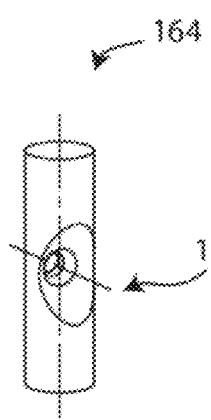
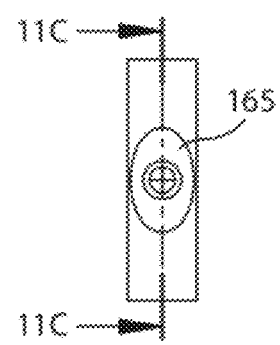
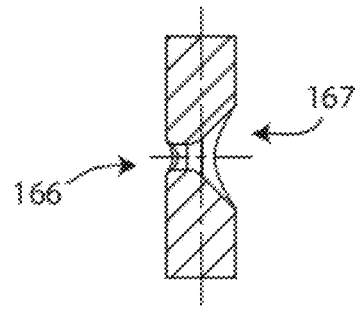
Fig. 11A     Fig. 11B     Fig. 11C
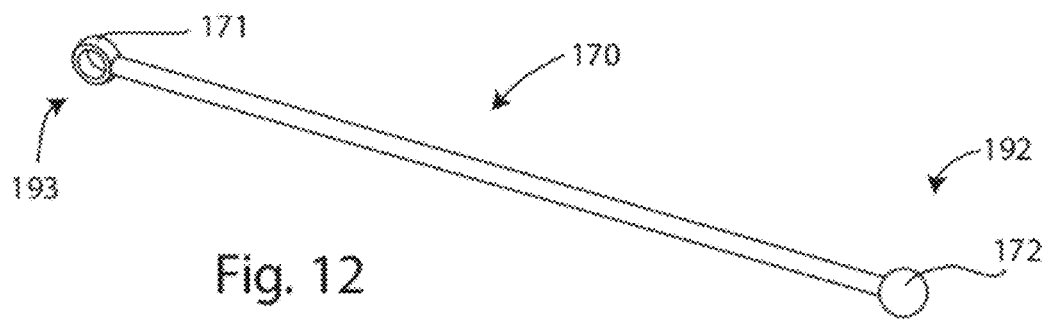
Fig. 12

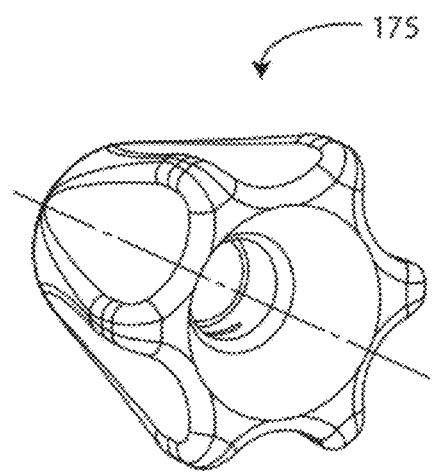
Fig. 13A
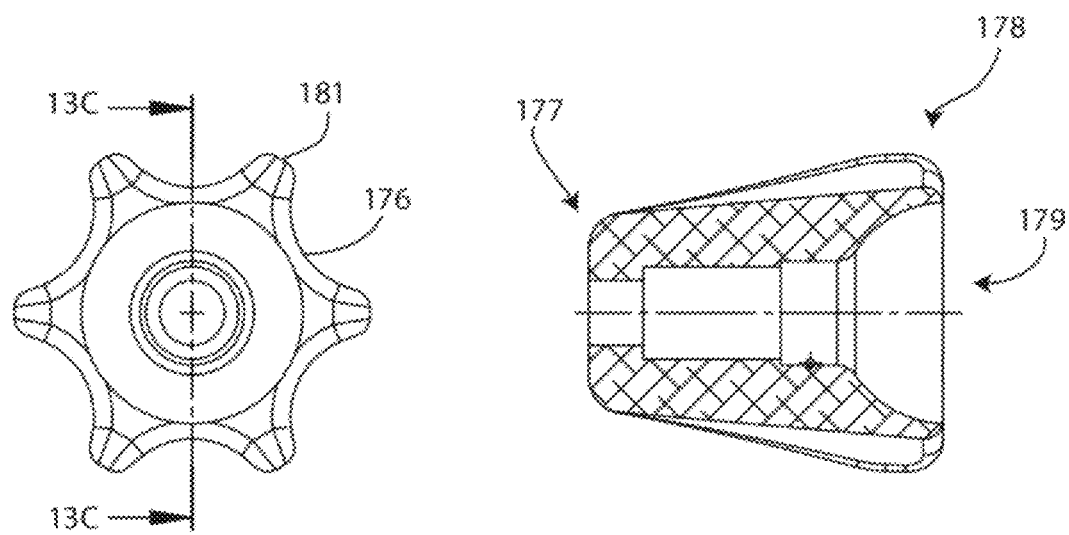
Fig. 13B
Fig. 13C

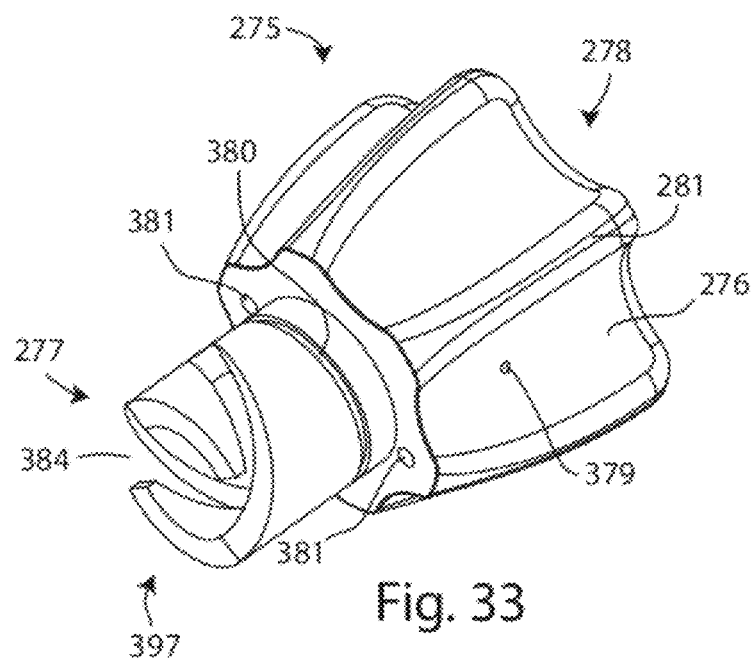
Fig. 33
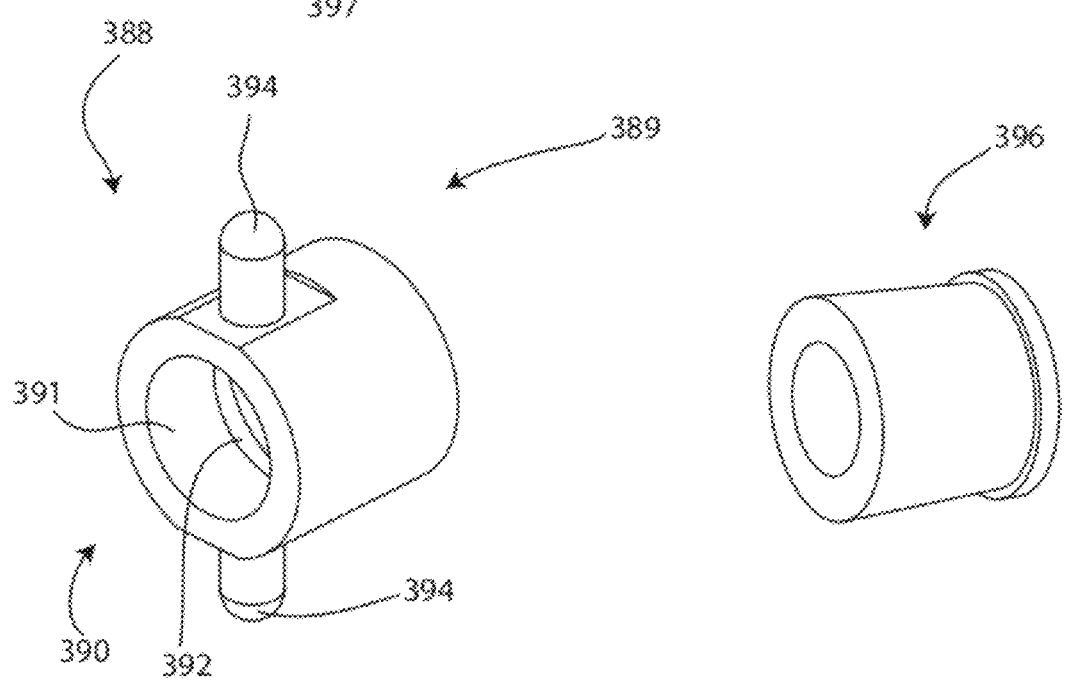
Fig. 34
Fig. 35

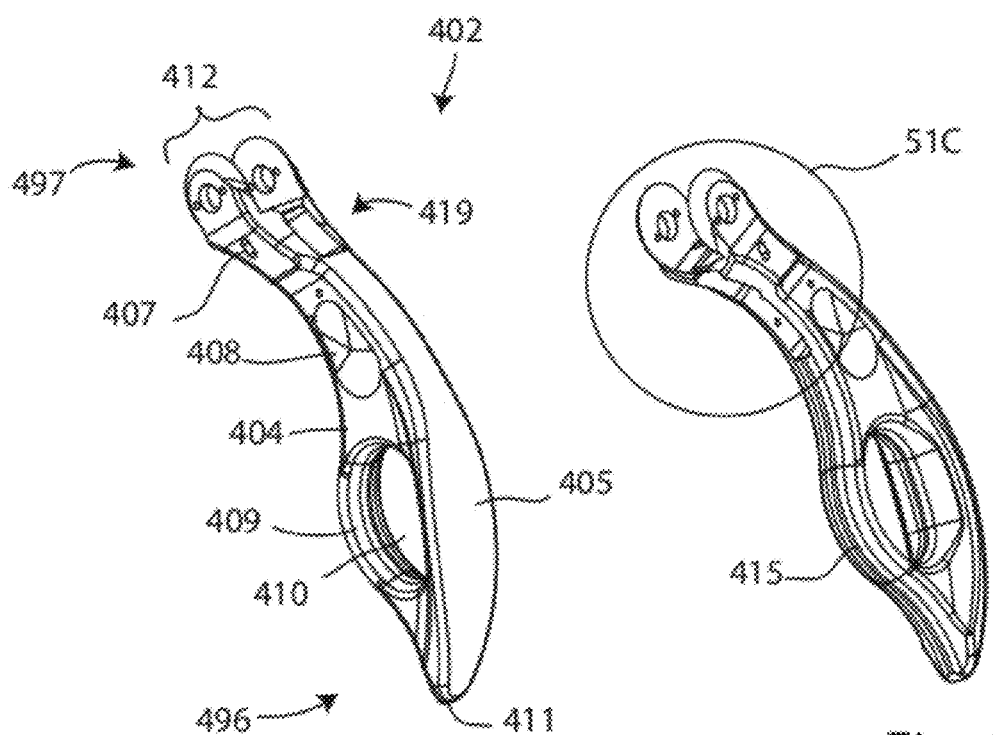
Fig. 51A
Fig. 51B
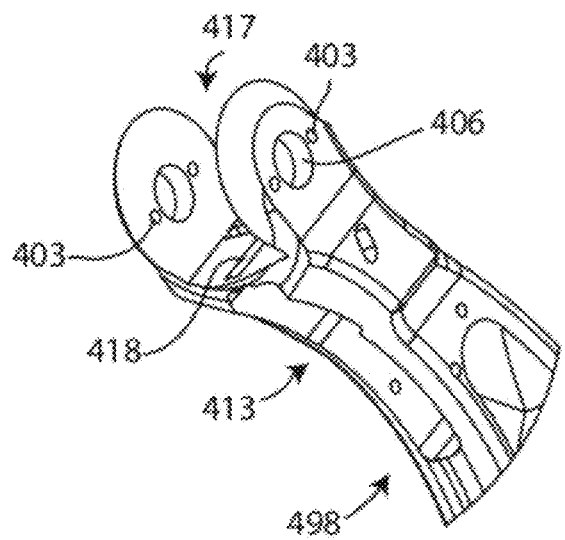
Fig. 51C

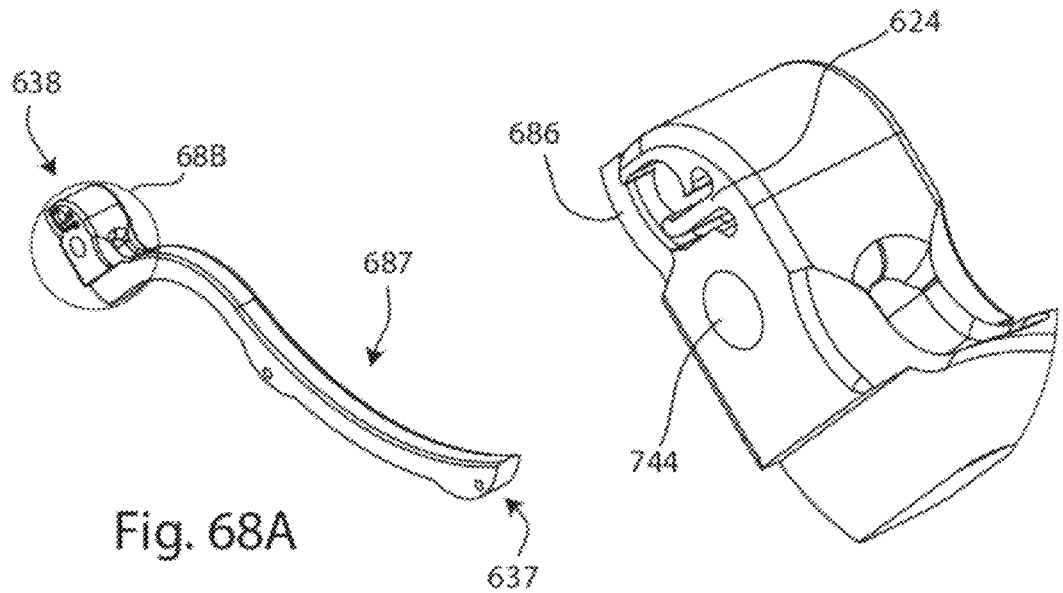
Fig. 68A
Fig. 68B
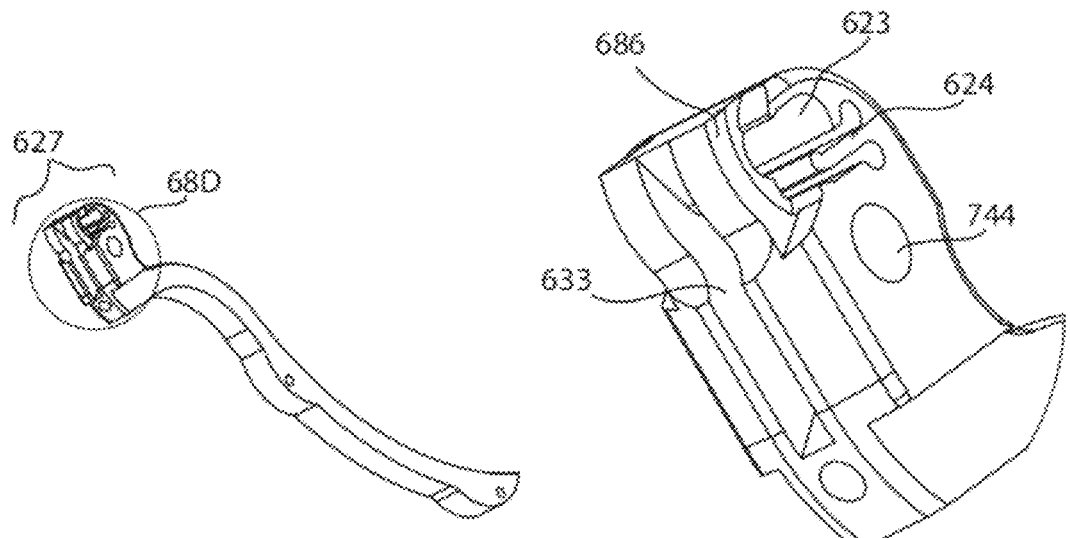
Fig. 68C
Fig. 68D

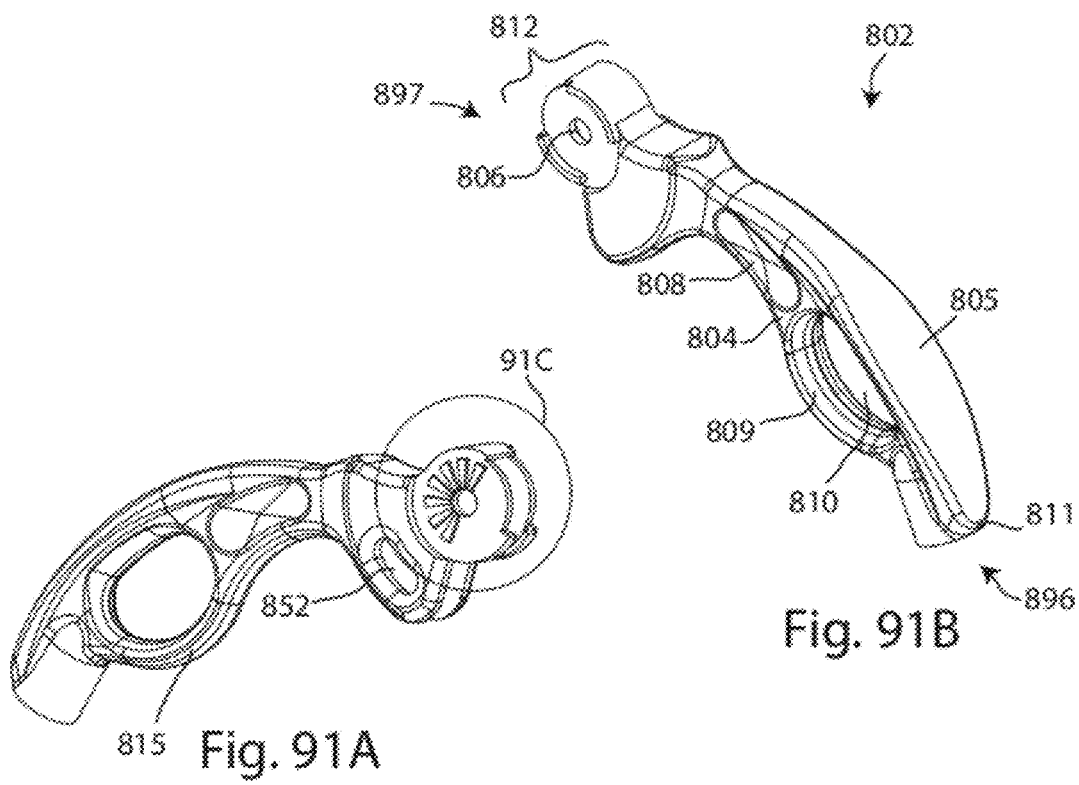
Fig. 91A
Fig. 91B
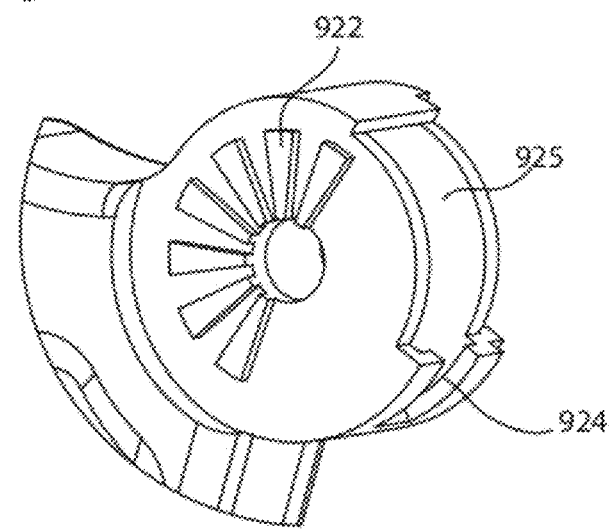
Fig. 91C

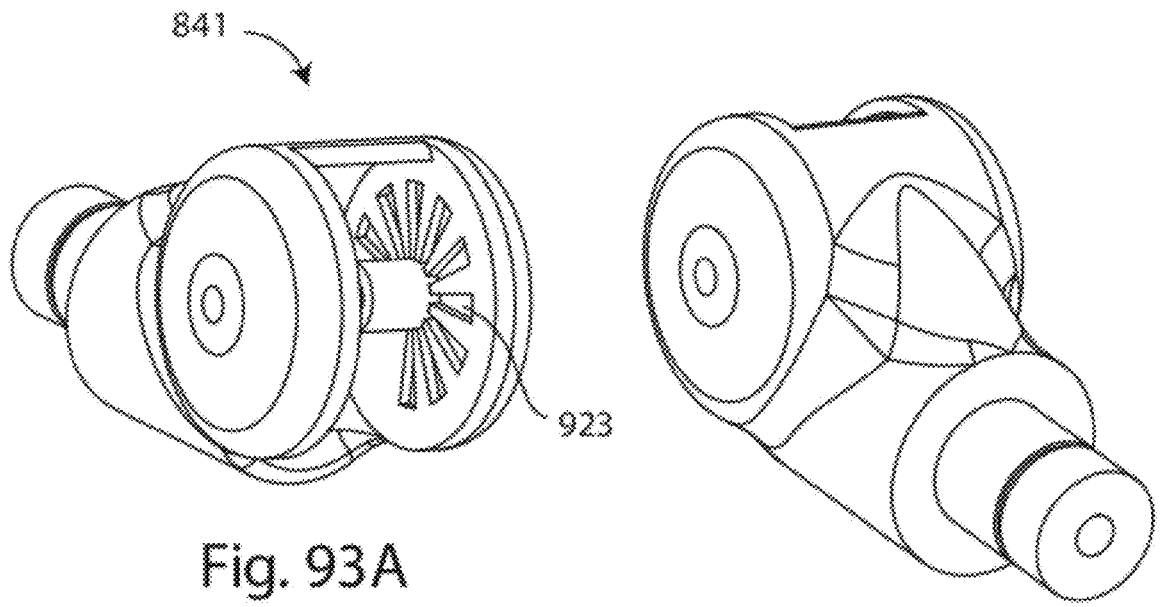
Fig. 93A
Fig. 93B
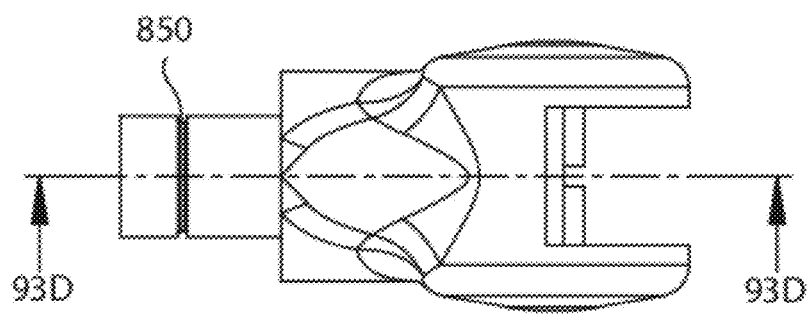
Fig. 93C
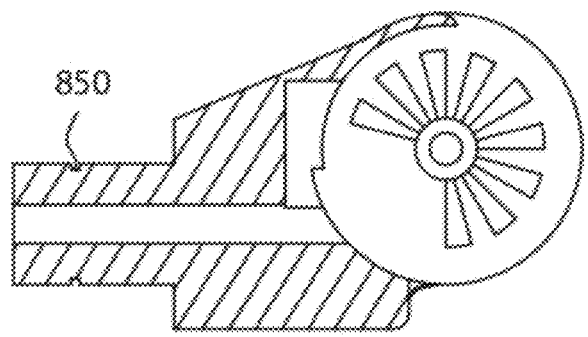
Fig. 93D

ADJUSTABLE LAPAROSCOPIC INSTRUMENT HANDLE

CROSS-REFERENCE TO RELATED APPLICATIONS

This application claims the benefit of:

U.S. Provisional Patent Application No. 61/442,510, which was filed on Feb. 14, 2011, is entitled: ADJUSTABLE LAPAROSCOPIC INSTRUMENT HANDLE. The contents of U.S. Application No. 61/442,510 are hereby incorporated by reference in its entirety as part of this application.

BACKGROUND

The present disclosure relates to instruments with adjustable handles. While the present disclosure is made in the context of laparoscopic instruments for the purposes of illustrating the concepts of the design, it is contemplated that the present design and/or variations thereof may be suited to other types of surgical instruments, such as arthroscopic, endoscopic, orthopedic, neurologic, cardiologic, suture passing, stapling, or minimally invasive instruments, among others. Furthermore, the principles embodied in the present disclosure may be applicable outside the fields of surgery or medical devices.

Laparoscopy is an established field of surgery, but opportunities remain for improvement to the instruments. Existing laparoscopic instruments may present significant challenges to a surgeon. For example, the design of laparoscopic instruments may force a surgeon to place his hands, arms, and/or body in non-ergonomic, uncomfortable, and sometimes physically harmful positions. Articulated instrument tips have been introduced. In at least some of these designs, the handle position and/or orientation may be altered in order to reposition and/or reorient the end effector. However, the handle position and/or orientation tends to be dependent on, or tied to, the end effector position and/or orientation.

There is a need for instrument designs that improve the ergonomics of the instruments in the user's hands. There is a need for instrument designs in which the handle position and/or orientation is independent of the end effector position and/or orientation. There is a need for instrument designs in which the user may adjust the instrument to keep the hands, arms, and/or body in an ergonomically appropriate or physiologically neutral position while positioning and/or orienting the end effector, or a working shaft of the instrument, to perform a procedure. There is also a need for instruments that reduce or eliminate the need to switch between different handle styles in the course of a procedure.

BRIEF DESCRIPTION OF THE DRAWINGS

FIG. 9 is a perspective view of a locking member according to one embodiment of the present disclosure;

FIG. 10 is a perspective view of a connector according to one embodiment of the present disclosure;

FIG. 11A is a perspective view of a pivot pin according to one embodiment of the present disclosure;

FIG. 11B is a front view of the pivot pin of FIG. 11A having a section line 11C-11C;

FIG. 11C is a cross-sectional side view of the pivot pin of FIG. 11B, taken along the section line 11C-11C in FIG. 11B.

FIG. 12 is an isometric view of an actuator according to one embodiment of the present disclosure;

FIG. 13A is an isometric view of a rotation knob according to one embodiment of the present disclosure;

FIG. 13B is a front view of the rotation knob of FIG. 13A having a section line 13C-13C;

FIG. 13C is a cross-sectional side view of the rotation knob of FIG. 13B, taken along the section line 13C-13C in FIG. 13B;

FIG. 33 is an isometric view of a rotation knob according to one embodiment of the present disclosure;

FIG. 34 is an isometric view of a control member according to one embodiment of present disclosure;

FIG. 35 is an isometric view of a working shaft collet;

FIG. 51A is an isometric view of a first handle in accordance with another embodiment of the present disclosure;

FIG. 51B is another isometric view of the first handle of FIG. 51A;

FIG. 51C is an enlarged view of the encircled area in FIG. 51B;

FIG. 68A is an isometric view of a portion of a second handle according to another embodiment of the present disclosure;

FIG. 68B is an enlarged view of the encircled area in FIG. 68A;

FIG. 68C is another isometric view of the portion of the second handle in FIG. 68A;

FIG. 68D is an enlarged view of the encircled area in FIG. 68C;

FIG. 69B is another isometric view of the pivot housing in FIG. 69A;

FIG. 70A is a top view of the pivot housing in FIGS. 69A-69B having a section line 70B;

FIG. 70B is a cross-sectional side view of the pivot housing in FIG. 70A, taken along the section line 70B-70B;

FIG. 71A is an isometric view of a locking member according to another embodiment of the present disclosure;

FIG. 71B is an isometric view of an actuator according to another embodiment of the present disclosure;

FIG. 72A is an isometric view of a connector according to another embodiment of the present disclosure;

FIG. 72B is another isometric view of the connector in FIG. 72A;

FIG. 73A is an isometric view of a rotation knob according to another embodiment of the present disclosure;

FIG. 73B is another isometric view of the rotation knob in FIG. 73A;

FIG. 73C is a front view of the rotation knob in FIG. 73A having section lines 73D-73D and 73E-73E;

FIG. 73D is a cross-sectional side view of the rotation knob in FIG. 73C, taken along the section line 73D-73D;

FIG. 73E is a cross-sectional side view of the rotation knob in FIG. 73C, taken along the section line 73C-73C;

Figure 61:
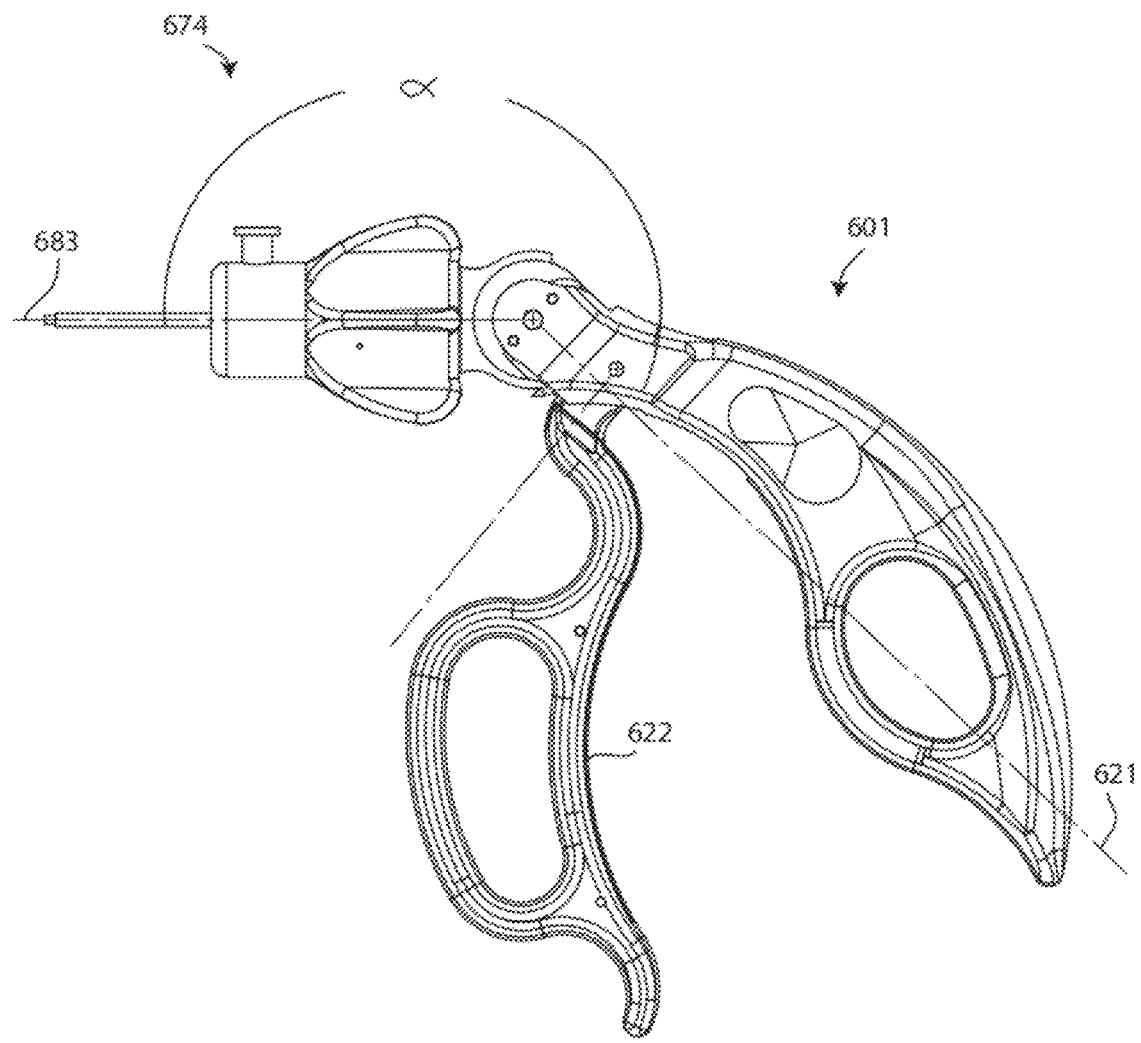
FIG. 61 is a side view of the surgical instrument of FIG. 60 with the handles of the surgical instrument in a "drop-down" position and with the second handle in an "at rest" position.
Figure 62:
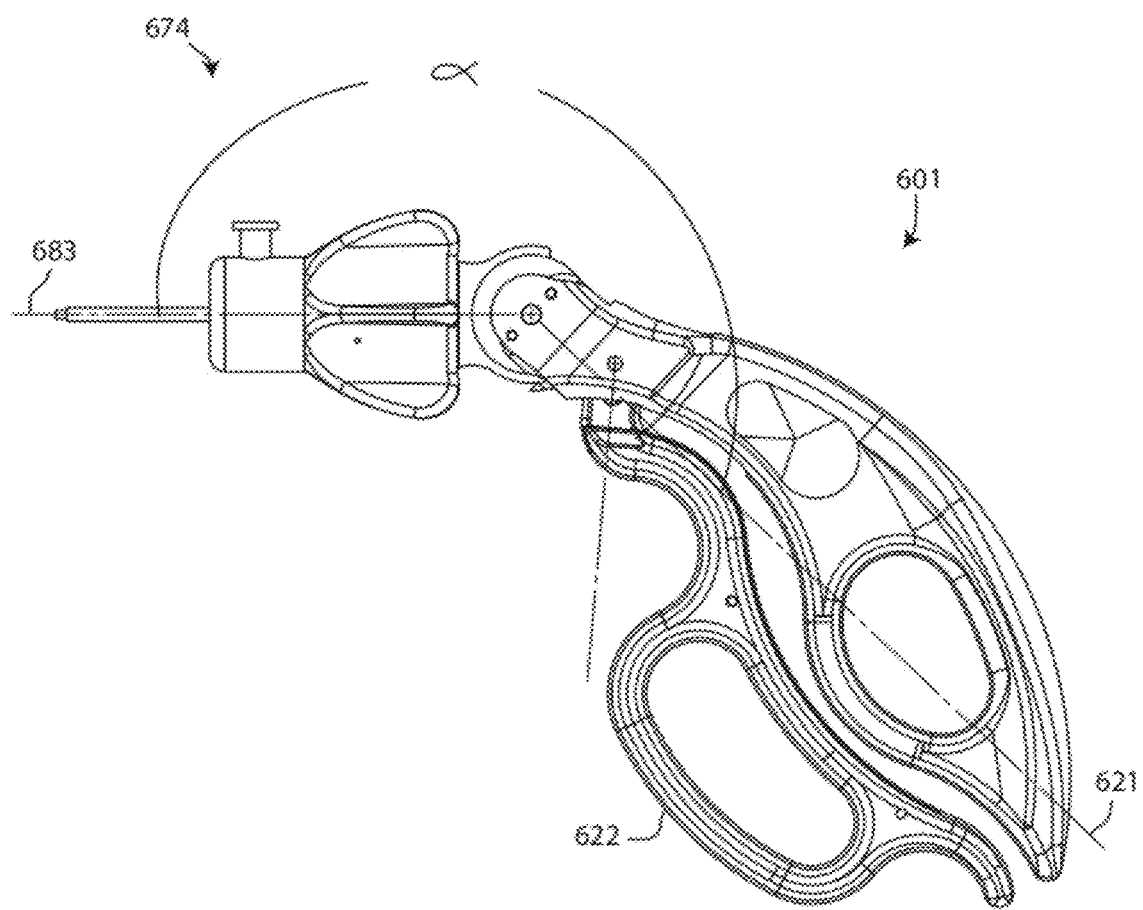
FIG. 62 is a side view of the surgical instrument of FIG. 61 with the second handle pivoted toward the first handle.
Figure 63:
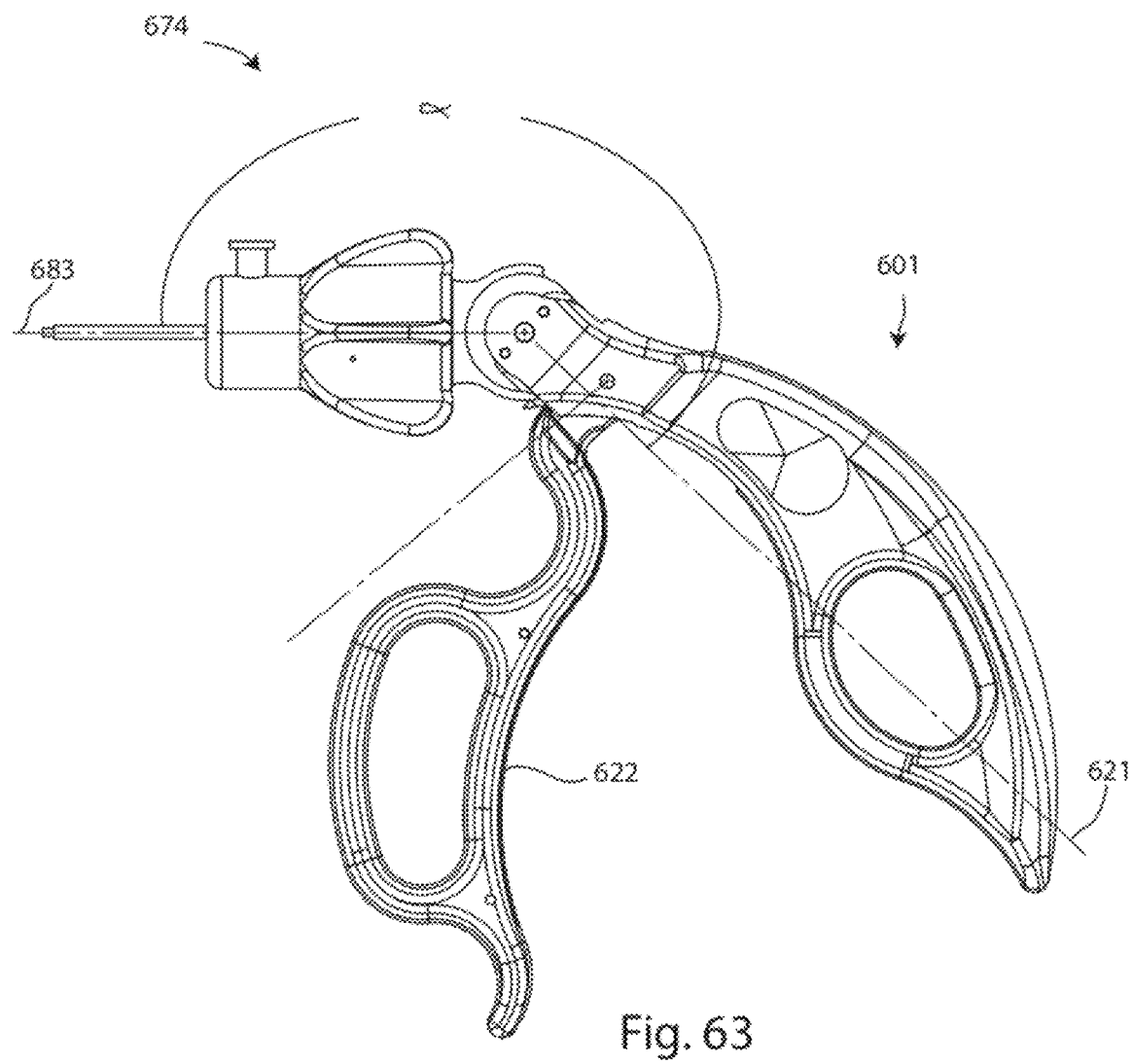
FIG. 63 is a side view of the surgical instrument of FIG. 61 with the second handle in a "forward" position.
Figure 64:
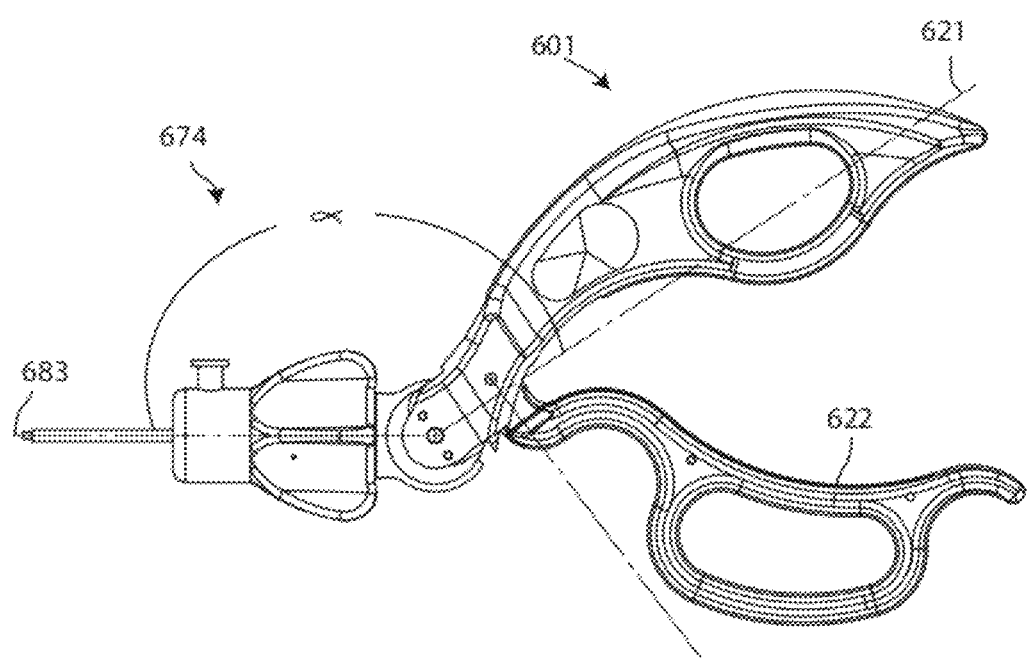
FIG. 64 is a side view of the surgical instrument of FIG. 60 with the handles of the surgical instrument in an "angled-up" position.
Figure 65:
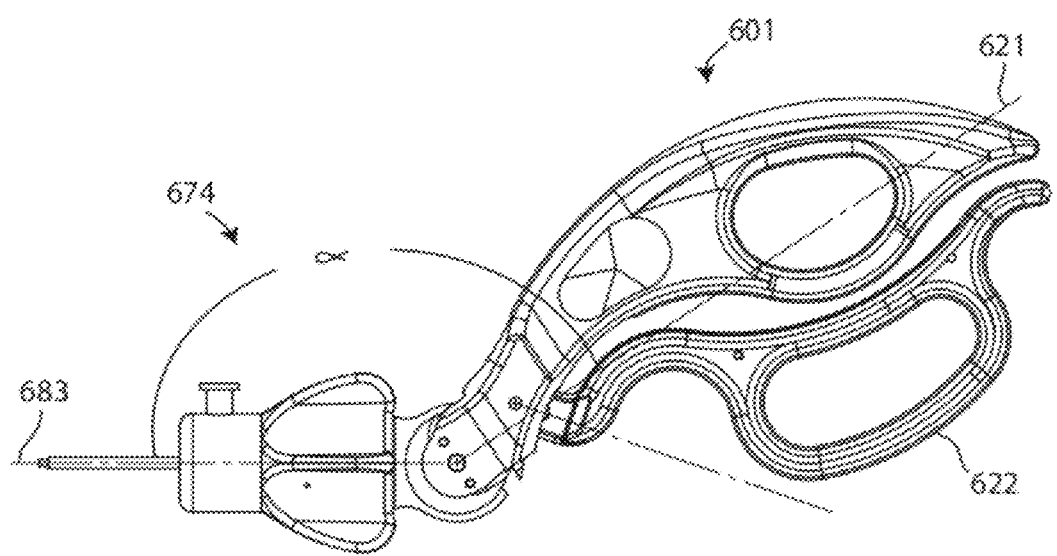
FIG. 65 is a side view of the surgical instrument of FIG. 64 with the second handle pivoted toward the first handle.
Figure 74A:
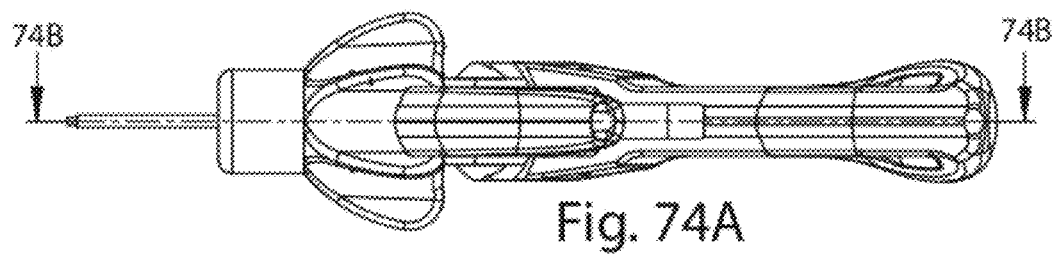
Figure 74B:
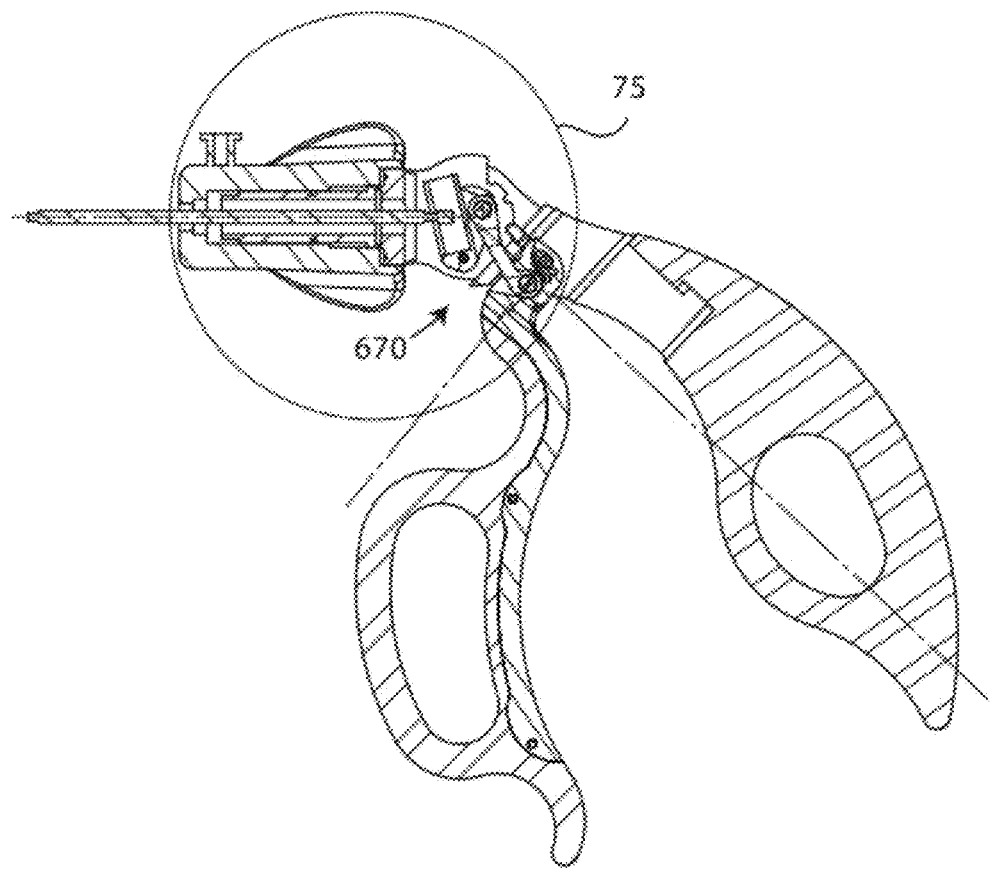
Figure 75:
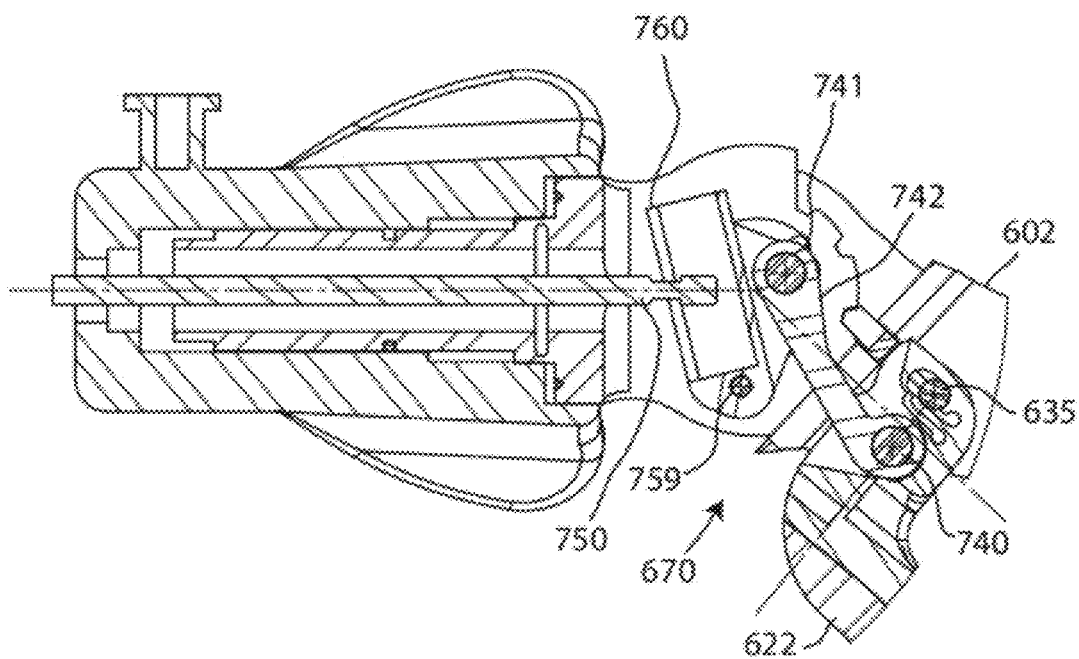
Figure 76A:
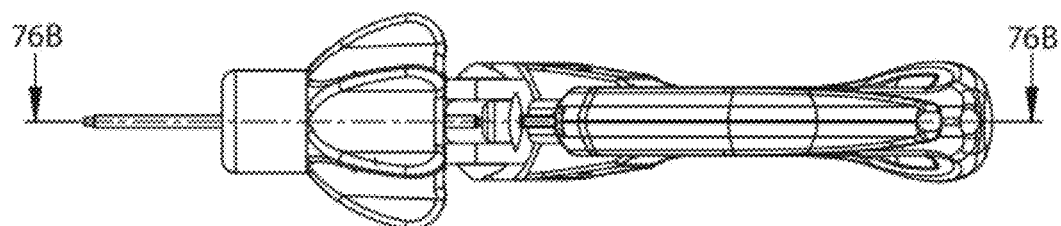
Figure 76B:
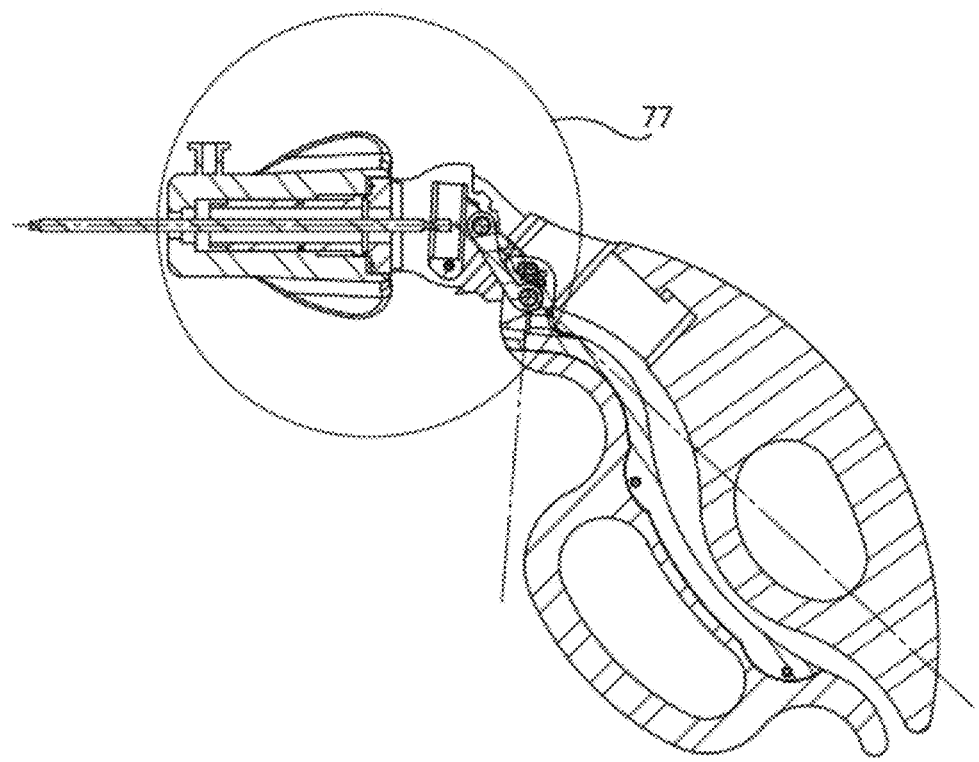
Figure 77:
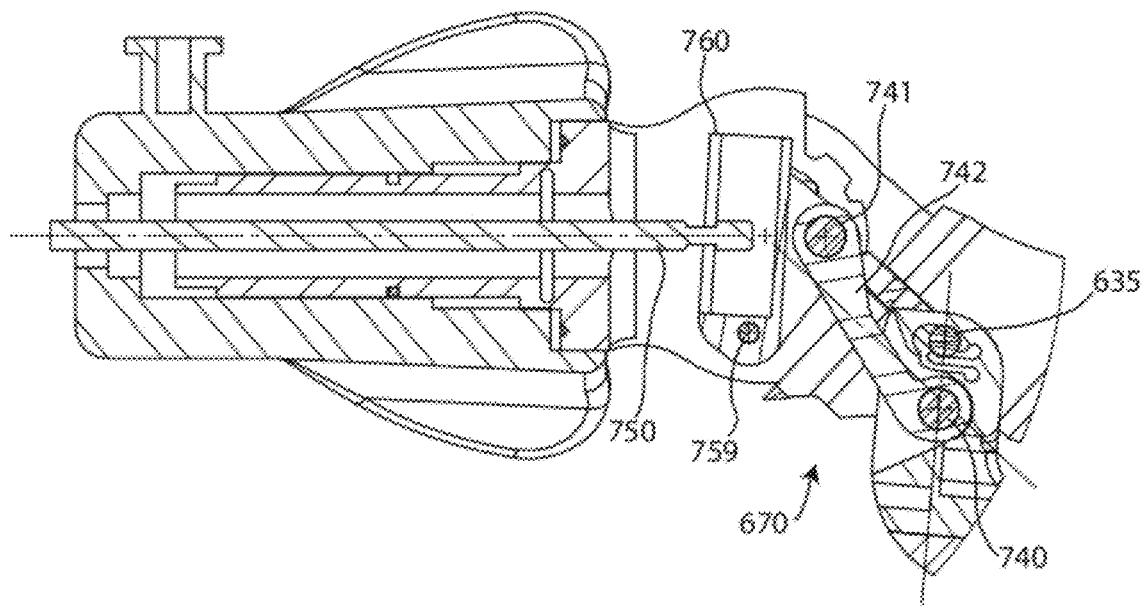
Figure 78A:
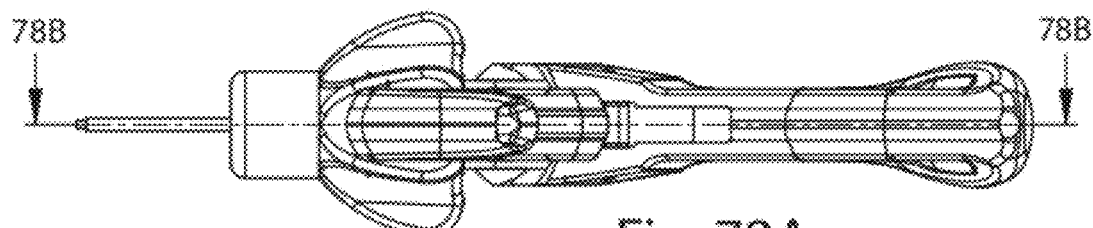
Figure 78B:
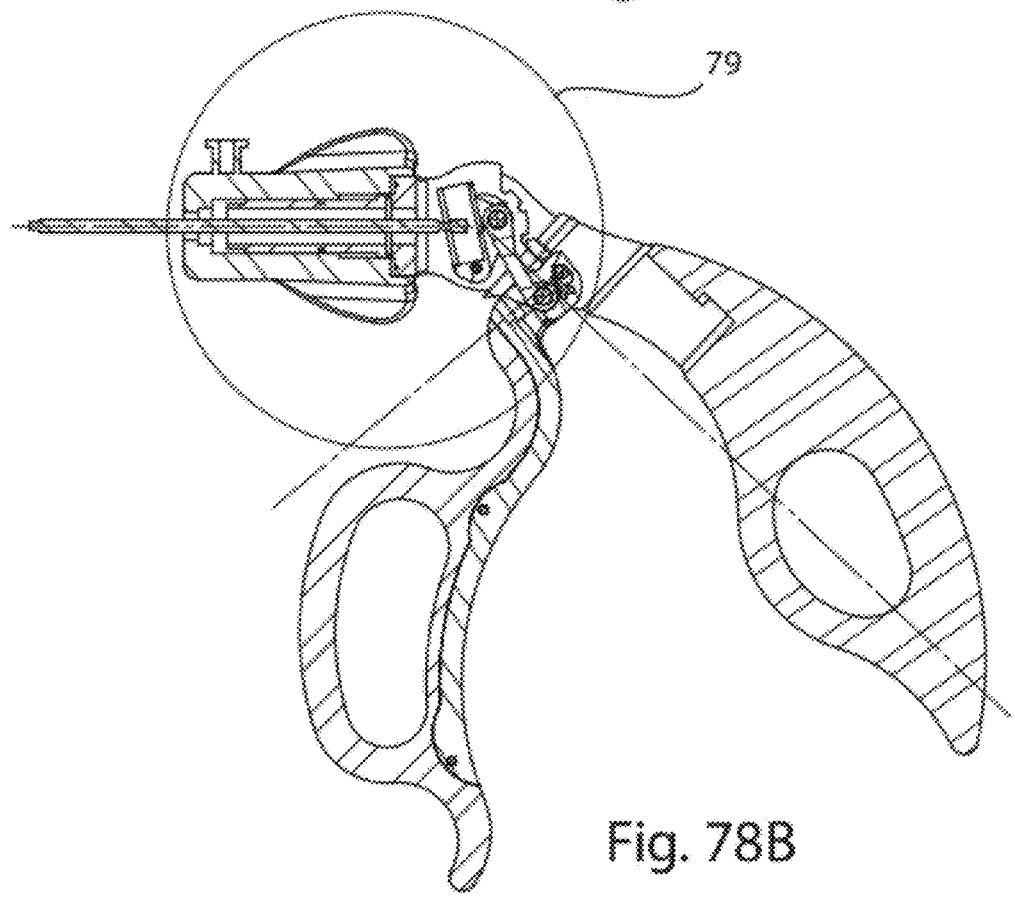
Figure 79:
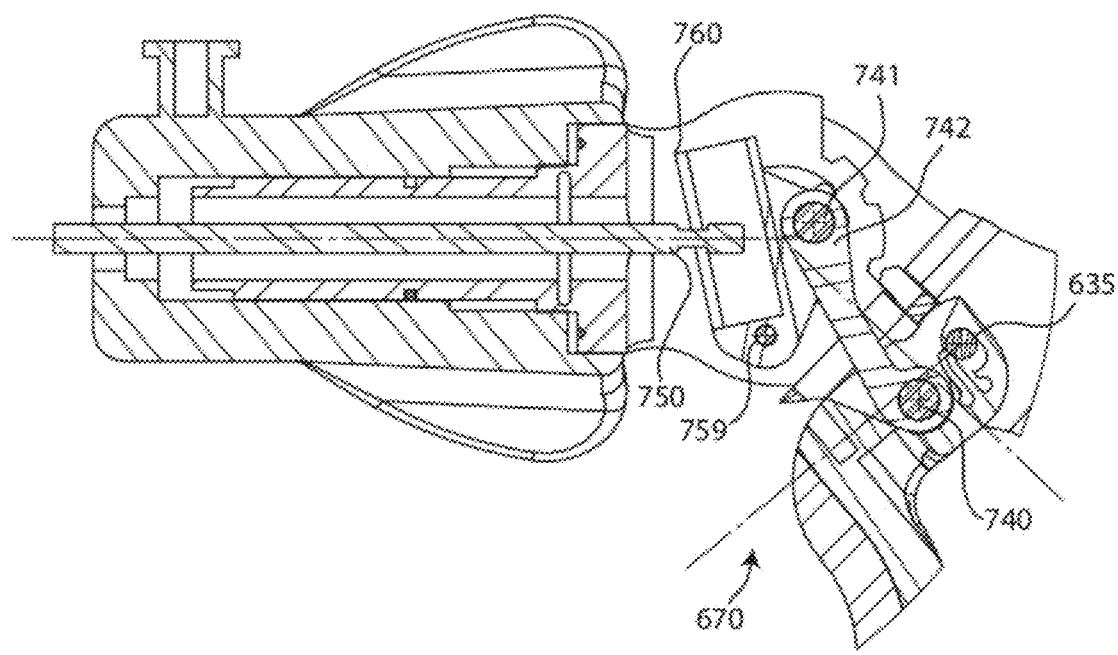
Figure 80A:
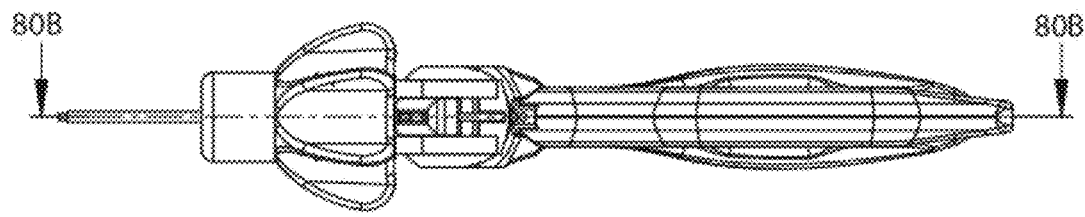
Figure 80B:
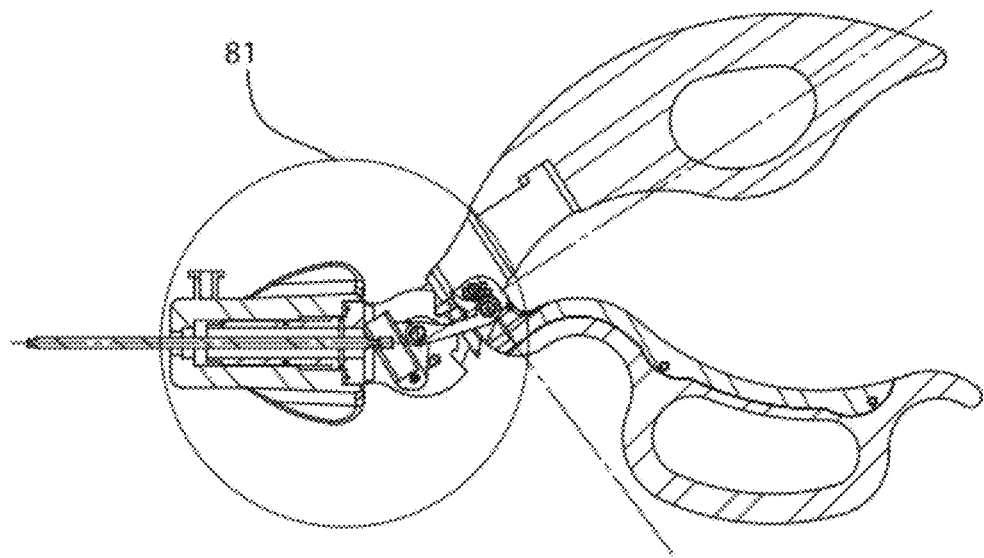
Figure 81:
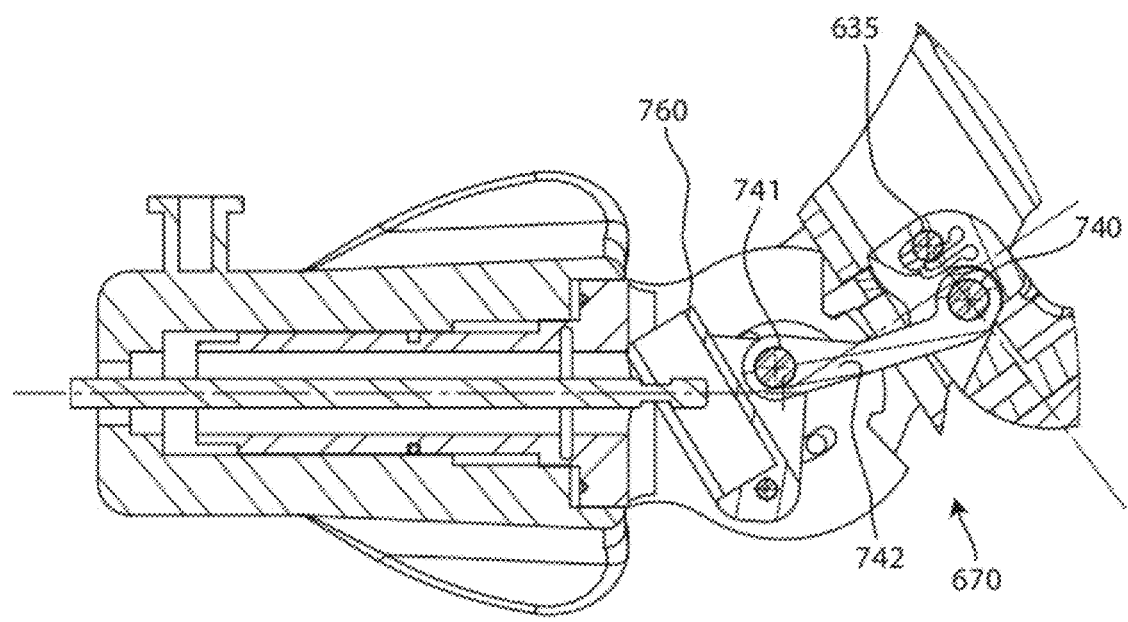
Figure 82A:
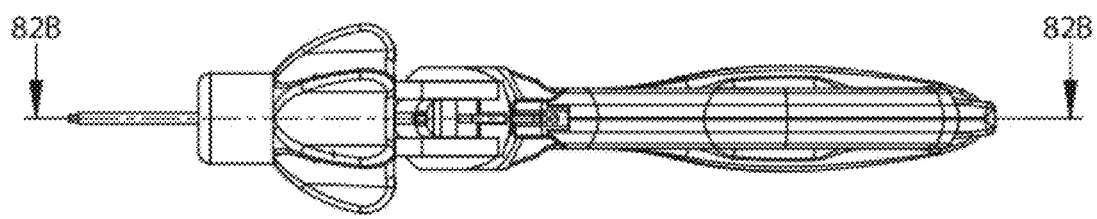
Figure 82B:
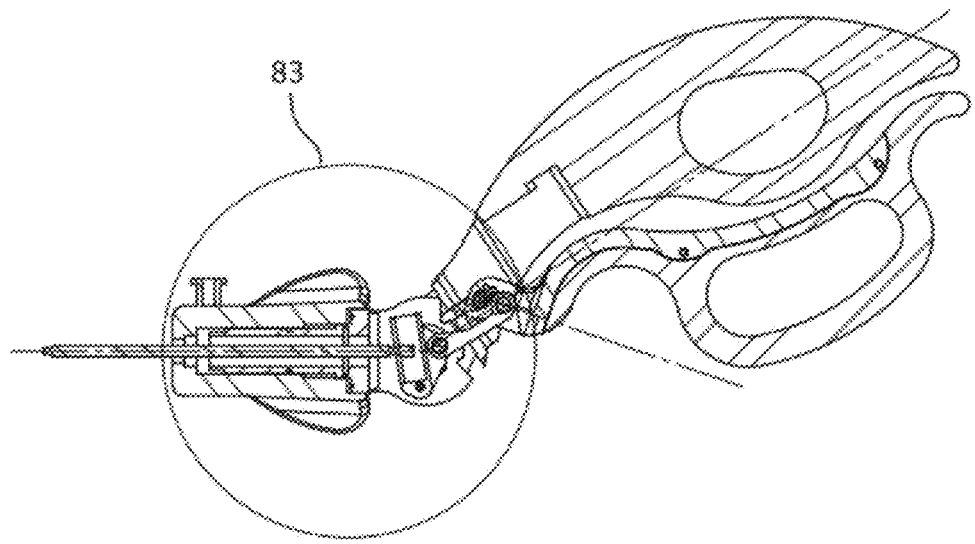
Figure 83:
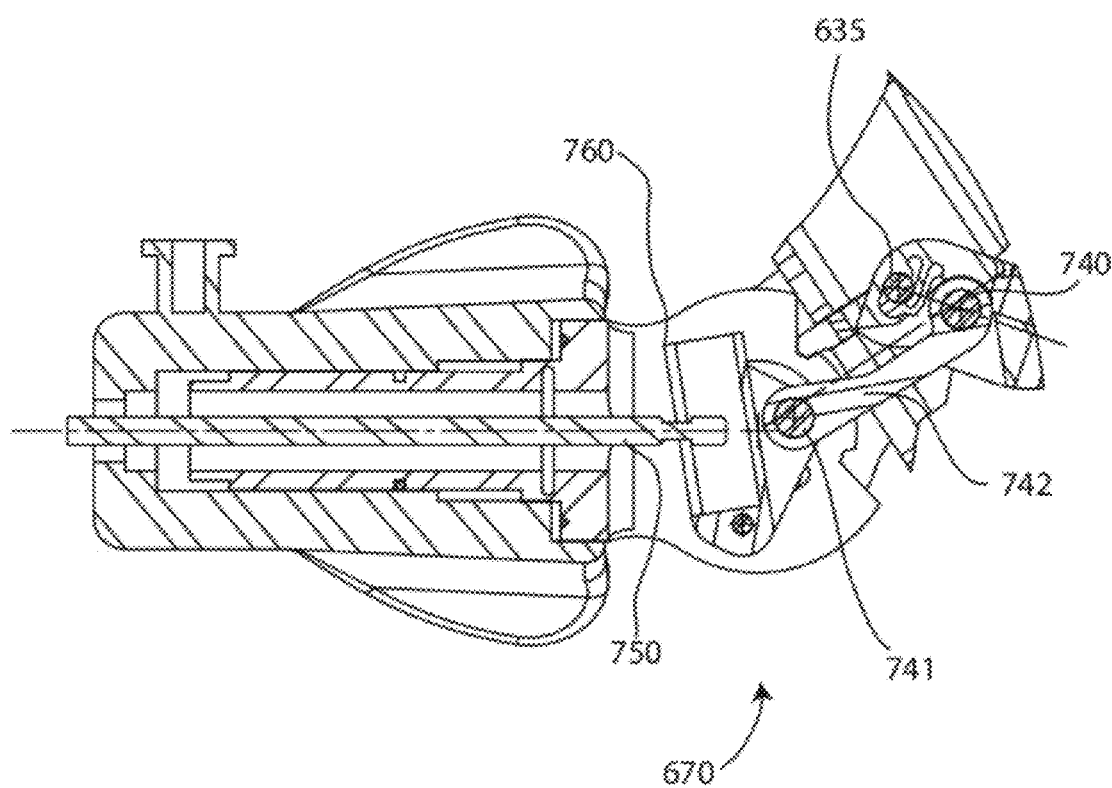
Figure 84:
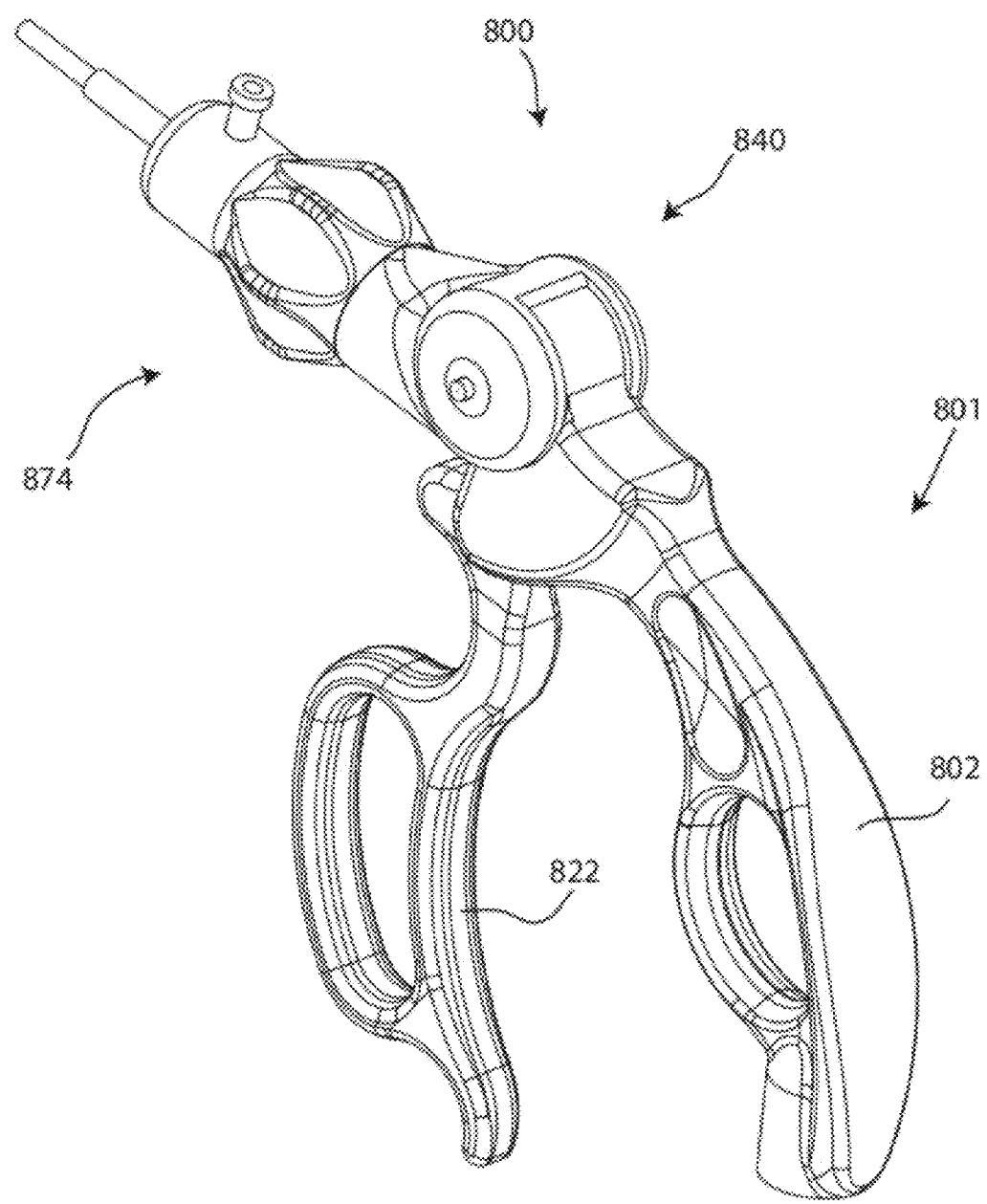
Figure 85:
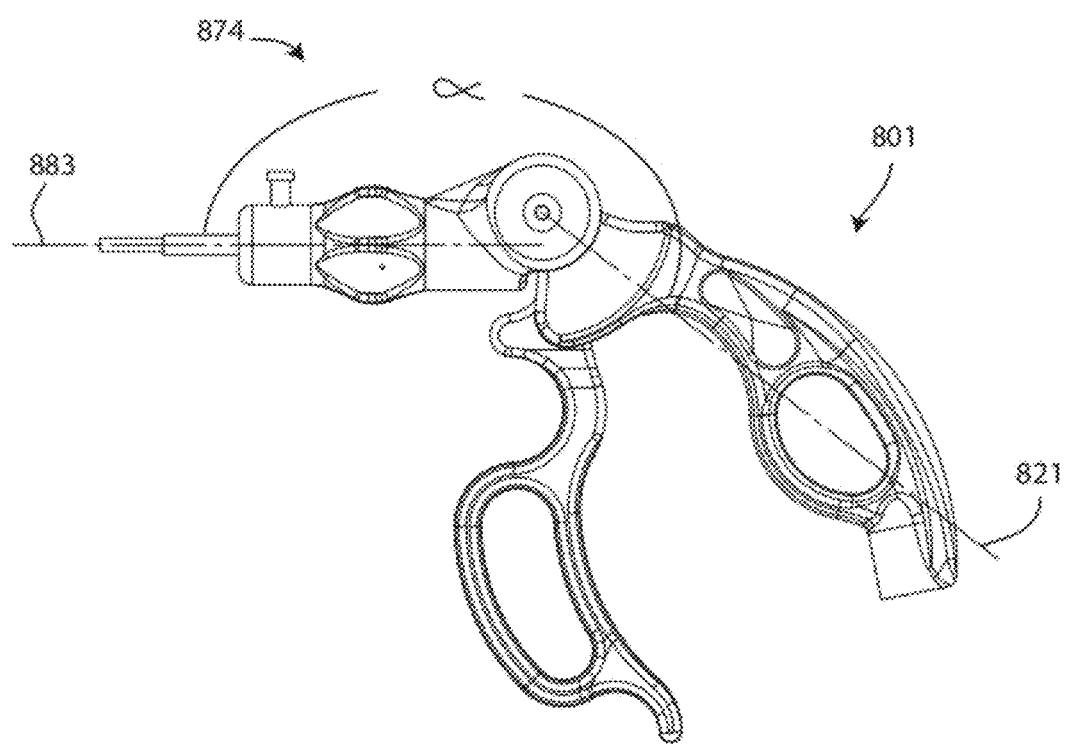
Figure 86:
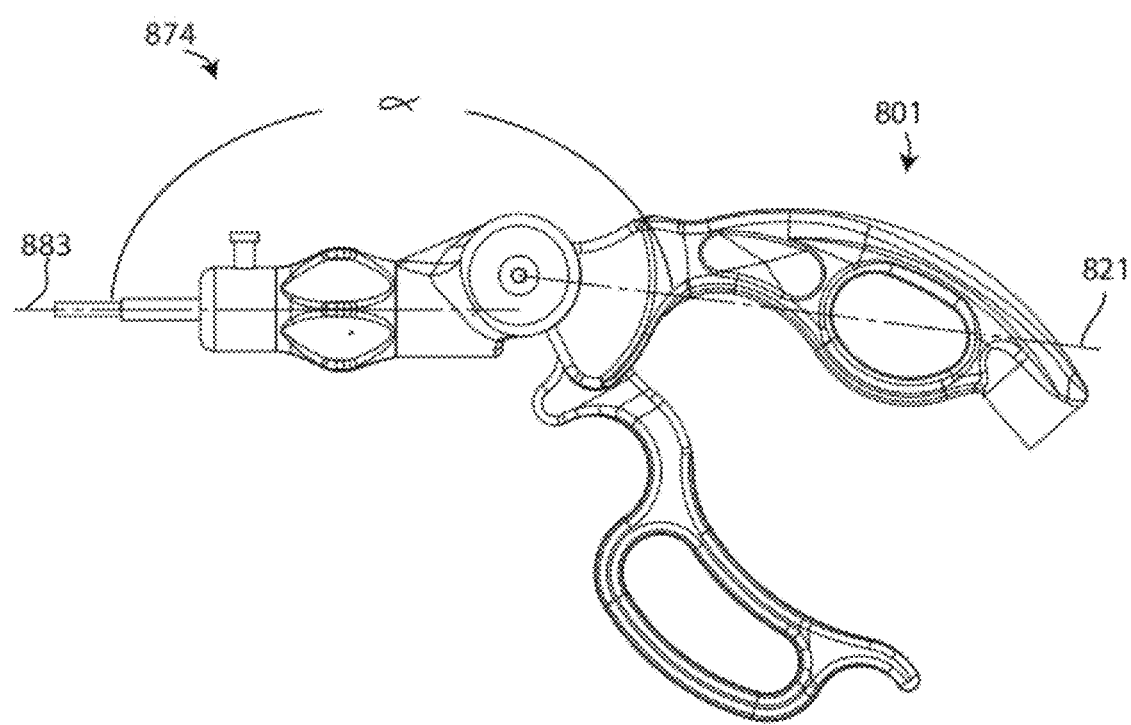
Figure 87:
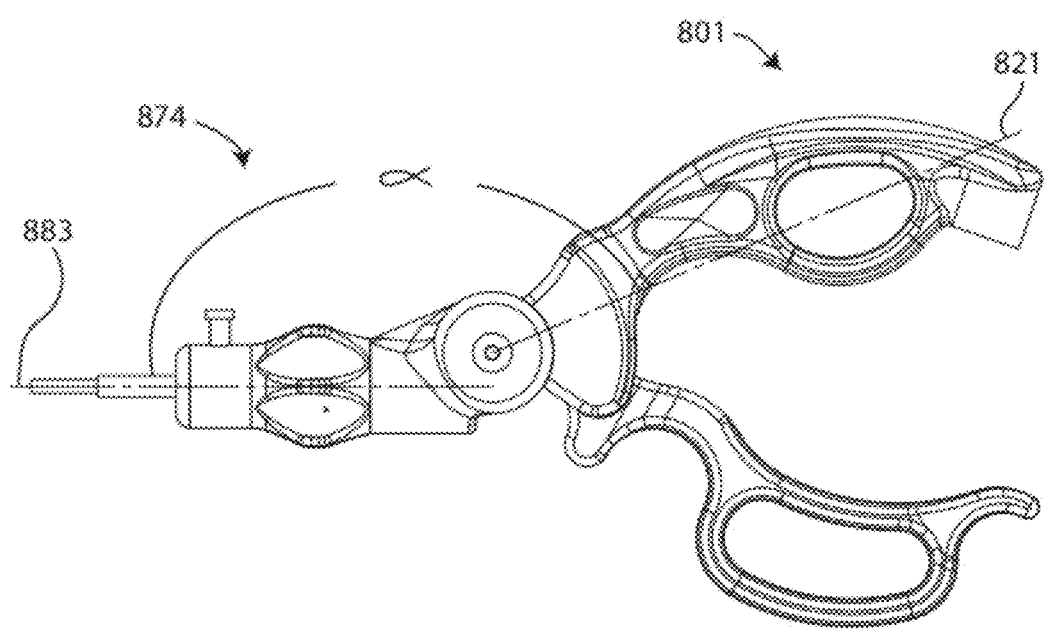
Figure 88:
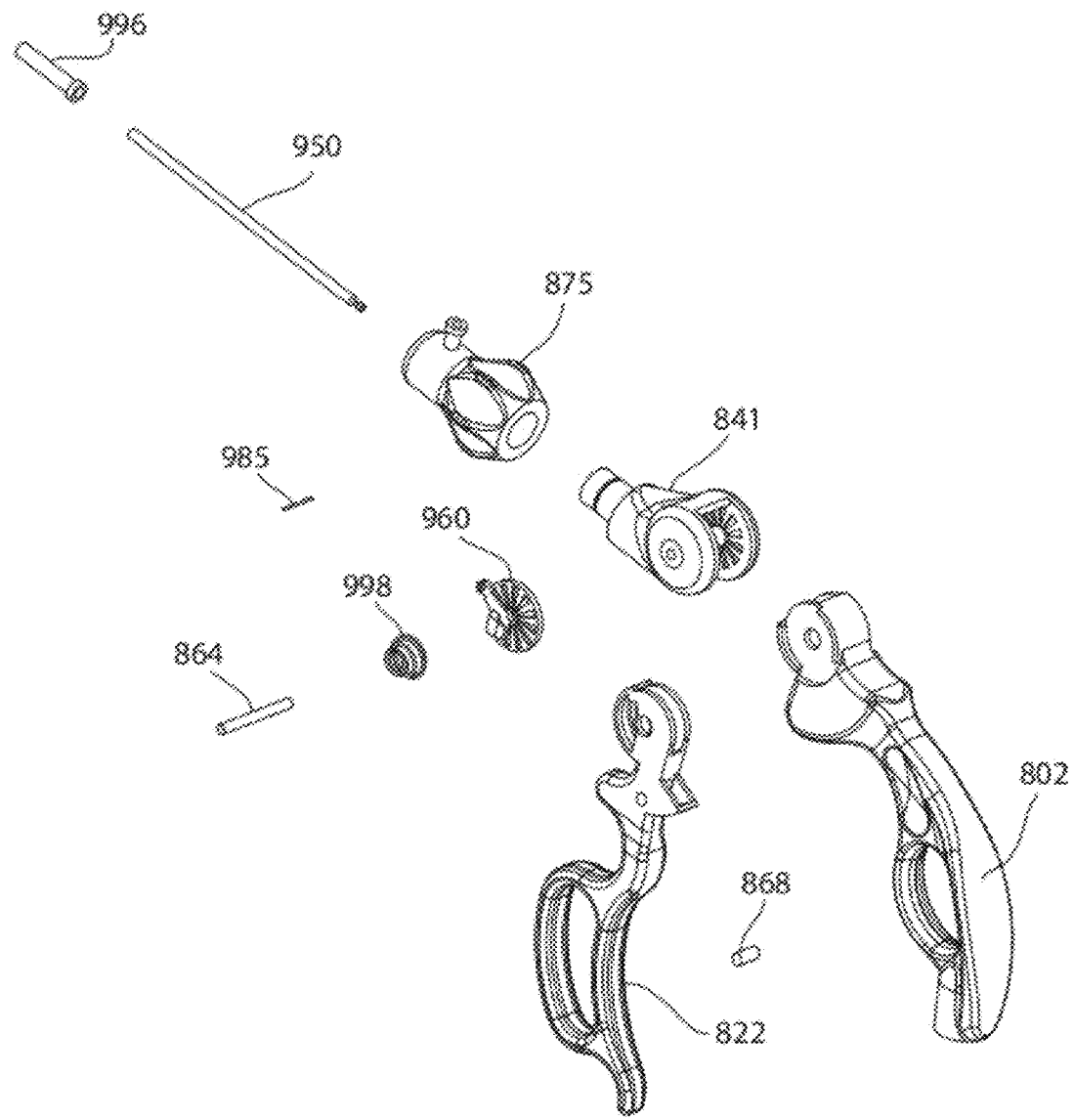
Figures 89A, 89B:
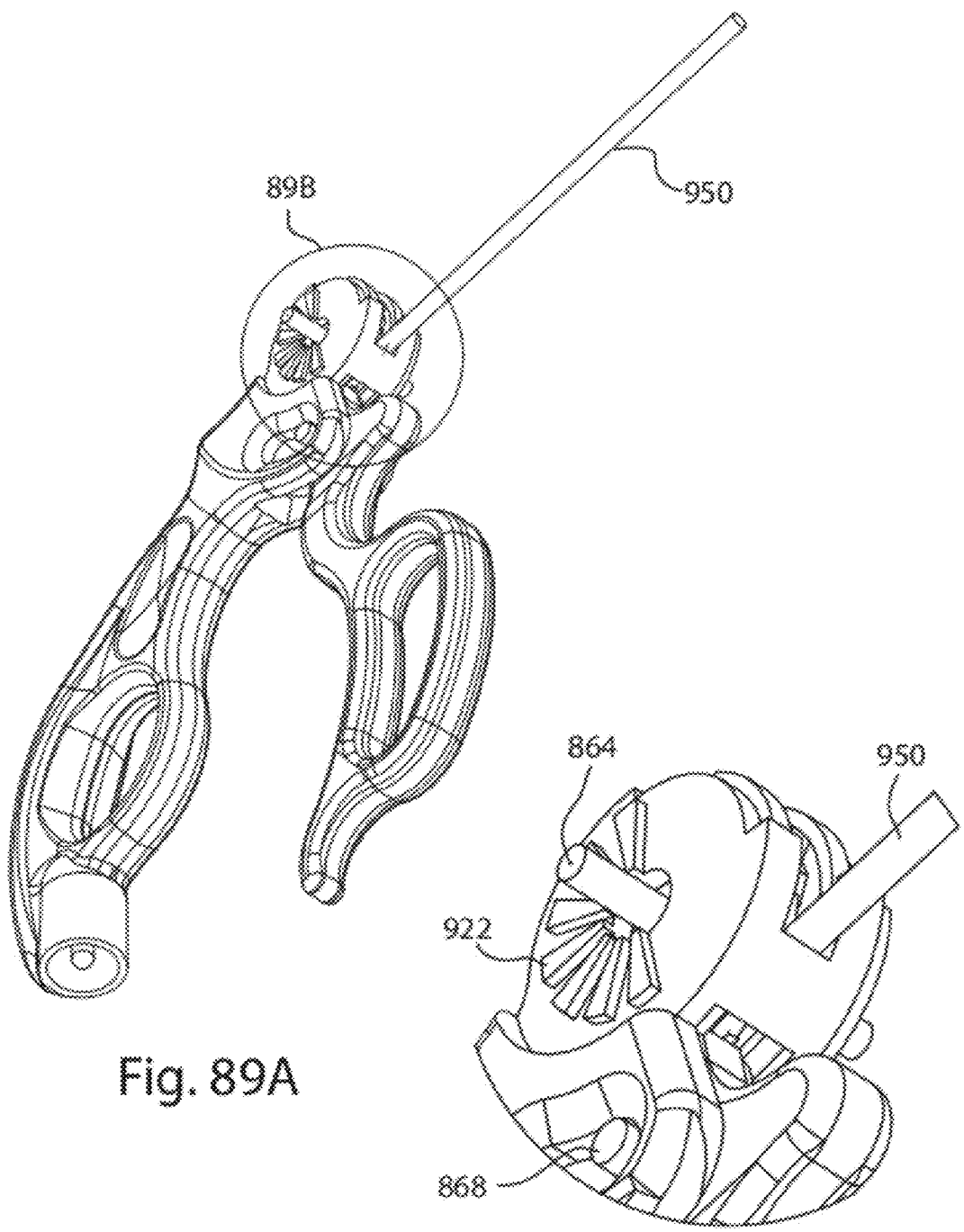
Figure 90A:
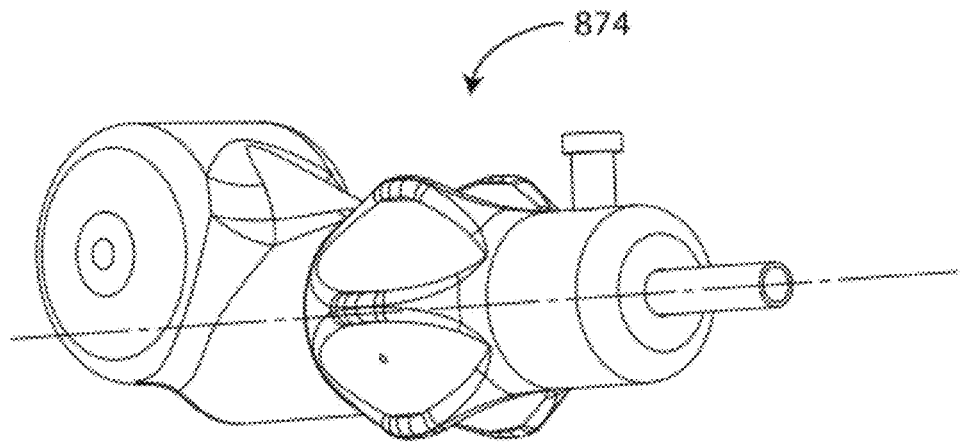
Figure 90B:
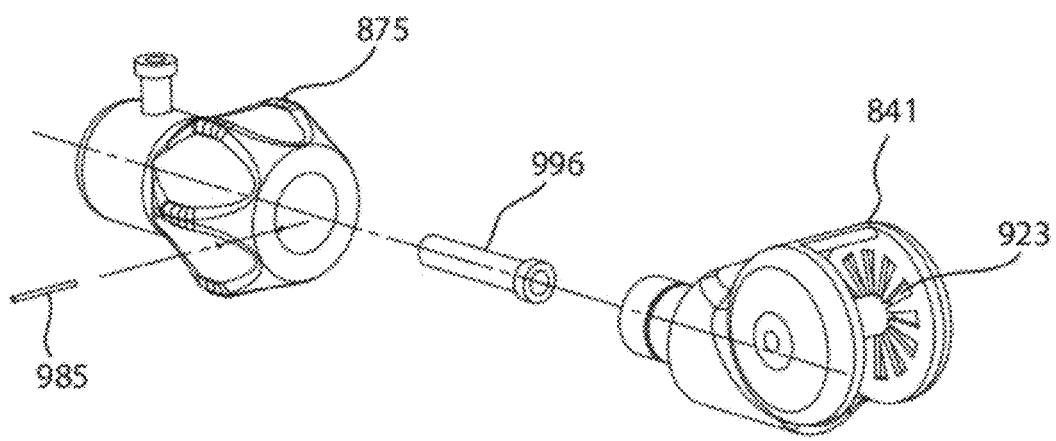
Figure 92A:
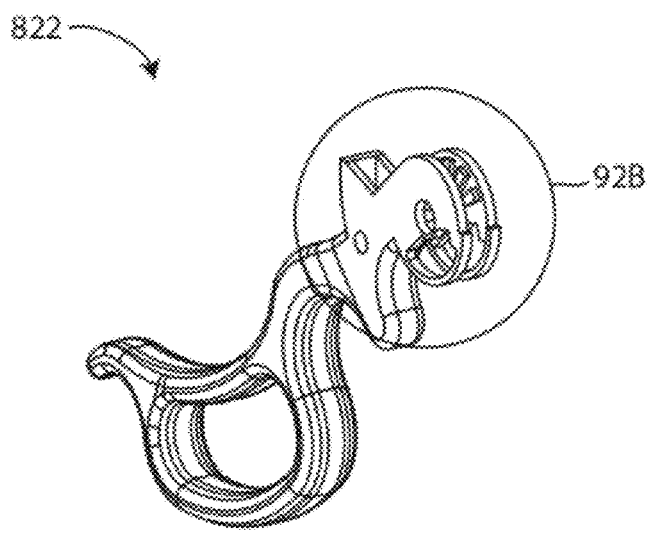
Figure 92B:
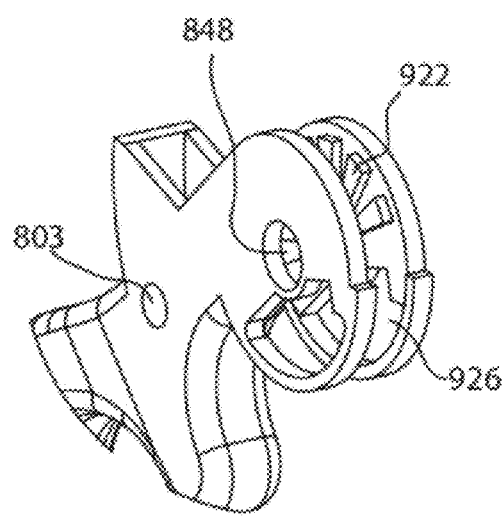
Figure 92C:
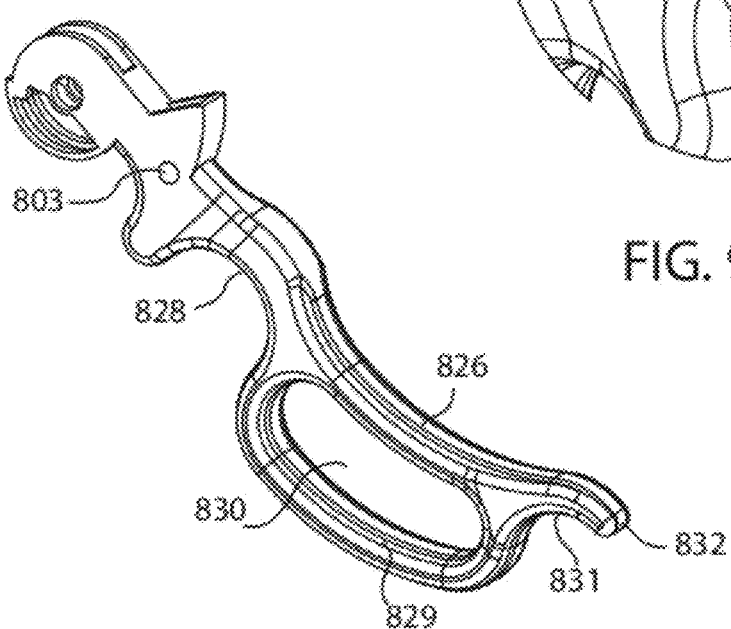
Figure 94A:
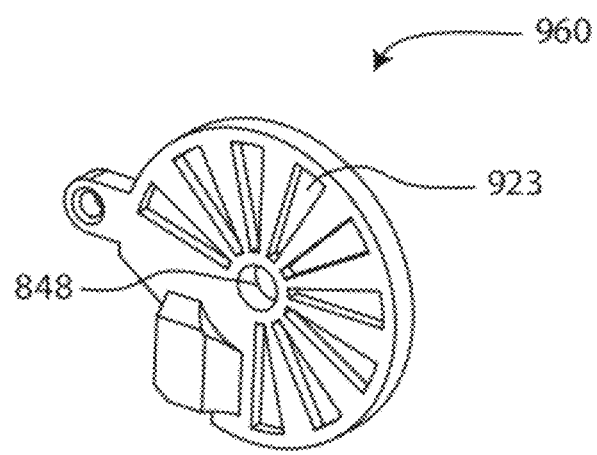
Figure 94B:
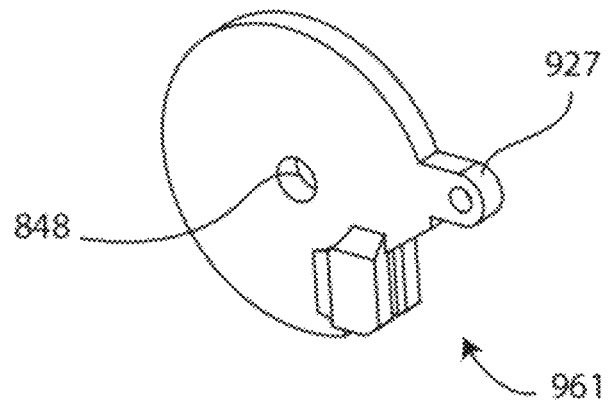
Figure 95A:
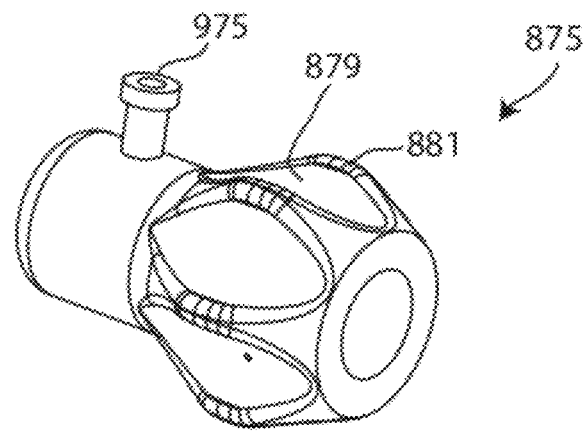
Figure 95B:
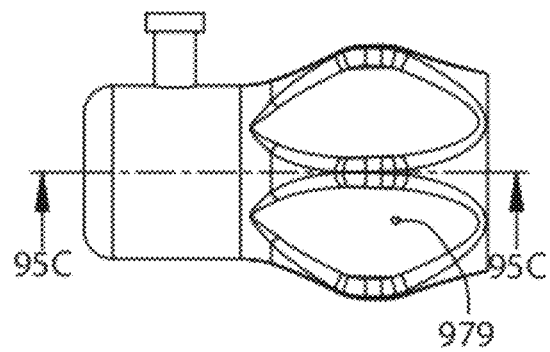
Figure 95C:
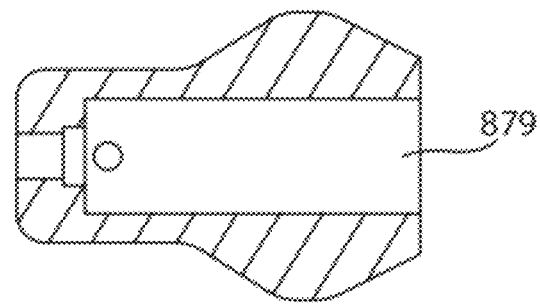
Figure 96A:
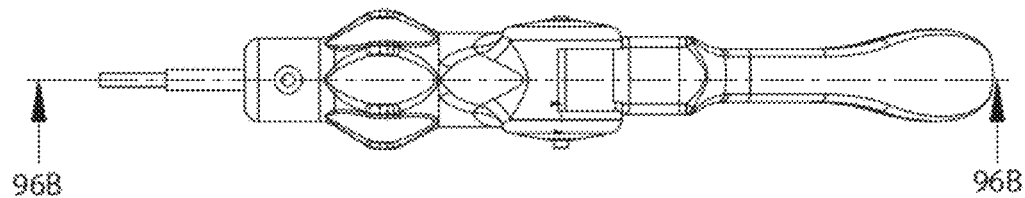
Figure 96B:
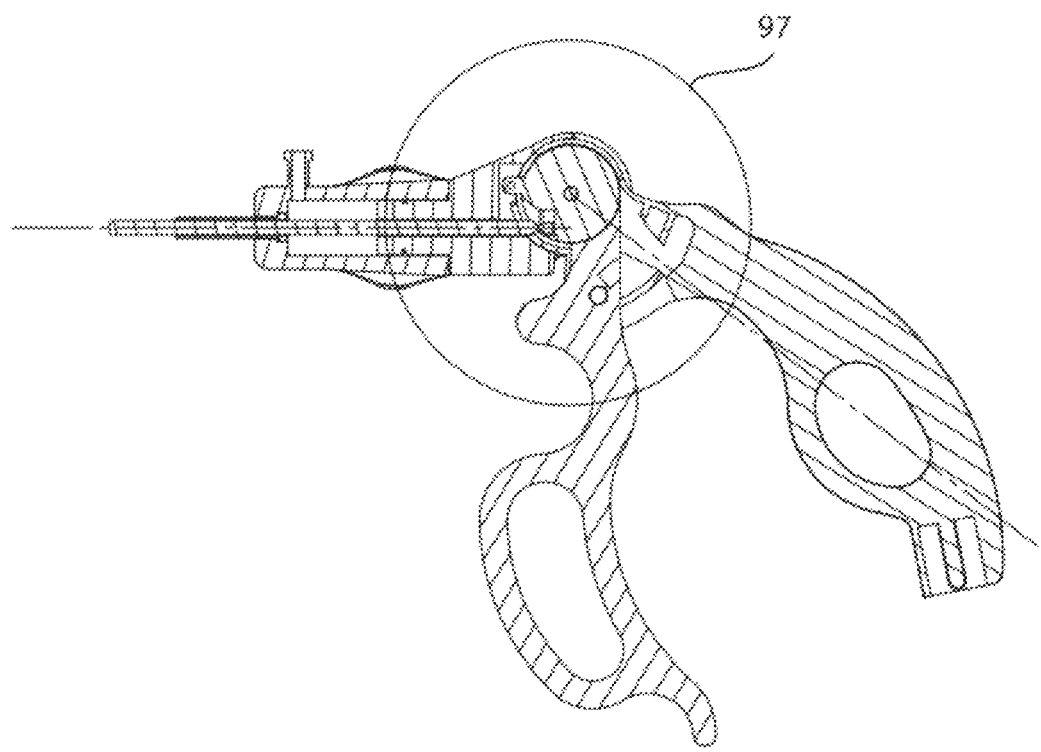
Figure 97:
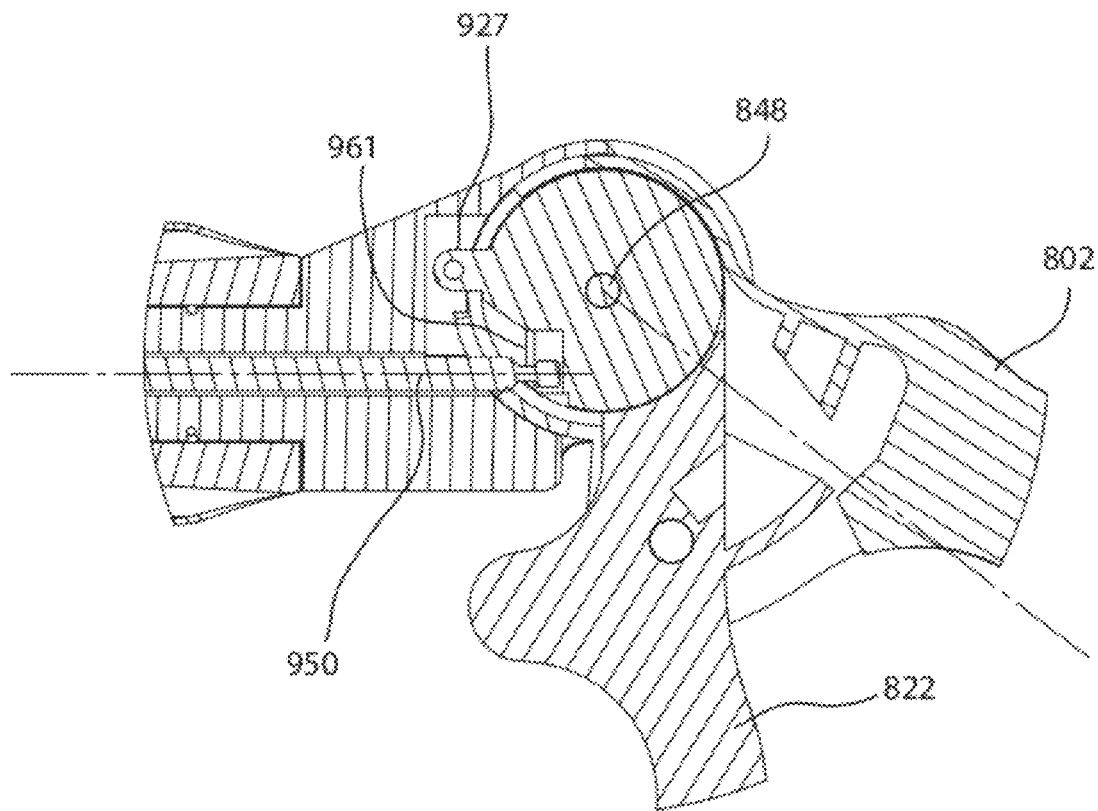

FIG. 74A is a top view of the surgical instrument shown in FIG. 61 having a section line 74B-74B;

FIG. 74B is a cross-sectional side view of the surgical instrument of FIG. 74A, taken along the section line 74B-74B in FIG. 74A;

FIG. 75 is an enlarged view of the encircled area in FIG. 74B;

FIG. 76A is a top view of the surgical instrument shown in FIG. 62 having a section line 76B-76B;

FIG. 76B is a cross-sectional side view of the surgical instrument of FIG. 76A, taken along the section line 76B-76B in FIG. 76A;

FIG. 77 is an enlarged view of the encircled area in FIG. 76B;

FIG. 78A is a top view of the surgical instrument shown in FIG. 63 having a section line 78B-78B;

FIG. 78B is a cross-sectional side view of the surgical instrument of FIG. 78A, taken along the section line 78B-78B in FIG. 78A;

FIG. 79 is an enlarged view of the encircled area in FIG. 78B;

FIG. 80A is a top view of the surgical instrument shown in FIG. 64 having a section line 80B-80B;

FIG. 80B is a cross-sectional side view of the surgical instrument of FIG. 80A, taken along the section line 80B-80B in FIG. 80A;

FIG. 81 is an enlarged view of the encircled area in FIG. 80B;

FIG. 82A is a top view of the surgical instrument shown in FIG. 65 having a section line 82B-82B;

FIG. 82B is a cross-sectional side view of the surgical instrument of FIG. 82A, taken along the section line 82B-82B in FIG. 82A;

FIG. 83 is an enlarged view of the encircled area in FIG. 82B;

FIG. 84 is an isometric view of a surgical instrument with an adjustable handle section according to another embodiment of the present disclosure;

FIG. 85 is a side view of the surgical instrument of FIG. 84 with the handles of the surgical instrument in a "drop-down" position;

FIG. 86 is a side view of the surgical instrument of FIG. 84 with the handles of the surgical instrument in an "in-line" position;

FIG. 87 is a side view of the surgical instrument of FIG. 84 with the handles of the surgical instrument in an "up-angled" position;

FIG. 88 is exploded view of the surgical instrument of FIG. 84;

FIG. 89A is an isometric view of the surgical instrument of FIG. 84 with the working shaft section removed;

FIG. 89B is an enlarged view of the encircled area in FIG. 89A;

FIG. 90A is an isometric view of a working shaft section according to one embodiment of the present disclosure;

FIG. 90B is an exploded view of the working shaft section in FIG. 90A;

FIG. 91A is an isometric view of a first handle according to another embodiment of the present disclosure;

FIG. 91B is another isometric view of the first handle in FIG. 91A;

FIG. 91C is an enlarged view of the encircled area in FIG. 91A;

FIG. 92A is an isometric view of a second handle according to another embodiment of the present disclosure;

FIG. 92B is an enlarged view of the encircled area in FIG. 92A;

FIG. 92C is another isometric view of the second handle in FIG. 92A;

FIG. 93A is an isometric view of a pivot housing according to another embodiment of the present disclosure;

FIG. 93B is another isometric view of the pivot housing in FIG. 93A;

FIG. 93C is a top view of the pivot housing in FIG. 93A having a section line 93D-93D;

FIG. 93D is a cross-sectional side view of the pivot housing in FIG. 93C, taken along the section line 93D-93D in FIG. 93C;

FIG. 94A is an isometric view of a connector according to another embodiment of the present disclosure;

FIG. 94B is another isometric view of the connector in FIG. 94A;

FIG. 95A is an isometric view of a rotation knob according to another embodiment of the present disclosure;

FIG. 95B is a side view of the rotation knob in FIG. 95A having a section line 95C-95C;

FIG. 95C is a cross-sectional side view of the rotation knob in FIG. 95B, taken along the section line 95C-95C in FIG. 95B;

FIG. 96A is a top view of the surgical instrument shown in FIG. 85 having a section line 96B-96B;

FIG. 96B is a cross-sectional side view of the surgical instrument shown in FIG. 96A, taken along the section line 96B-96B in FIG. 96A;

FIG. 97 is an enlarged view of the encircled area in FIG. 96B.

DETAILED DESCRIPTION

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Figure 1:
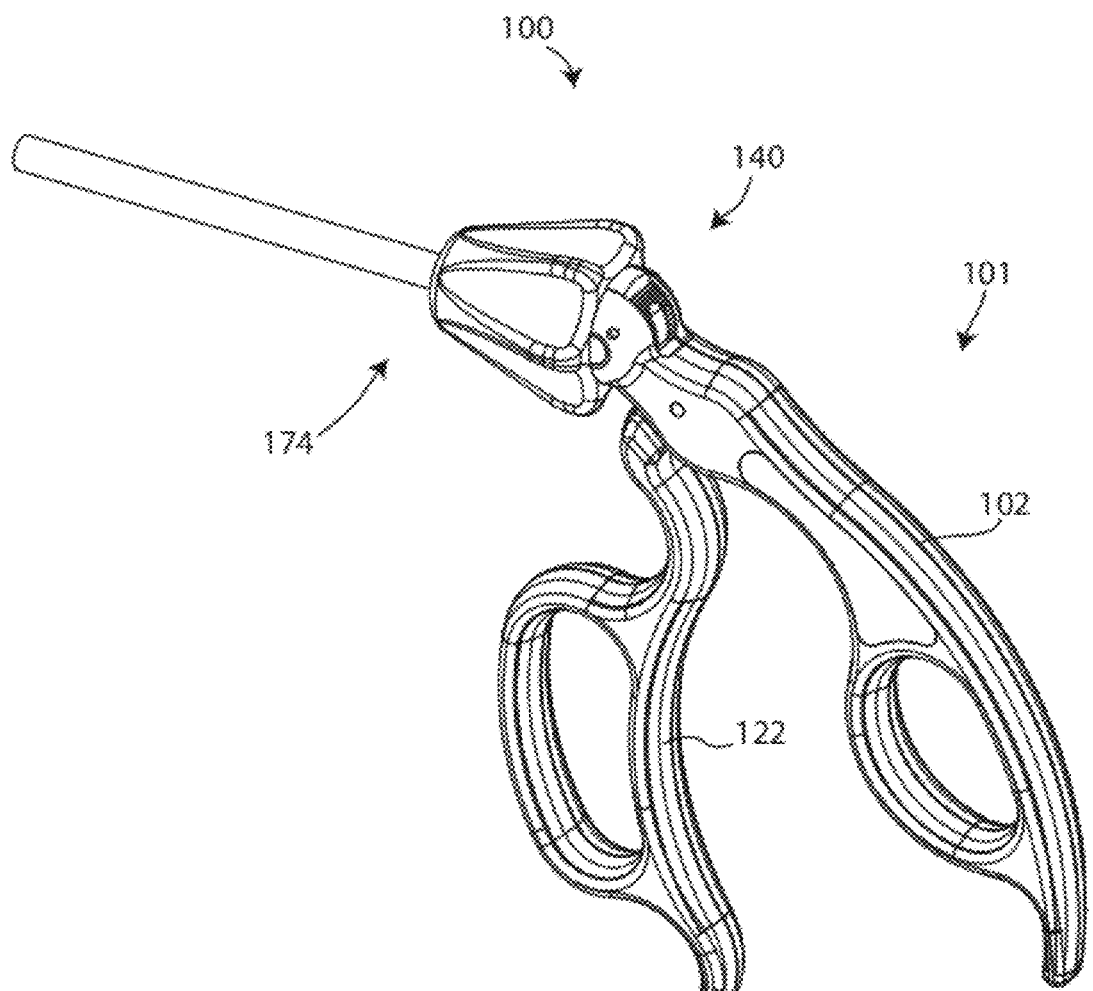
FIG. 1 is an isometric view of a surgical instrument with an adjustable handle section according to one embodiment of the present disclosure.

In FIGS. 1-15, a surgical instrument 100 in accordance with one embodiment of the present disclosure is illustrated. FIG. 1 shows an isometric view of a surgical instrument 100 having a working shaft section 174 at its distal end, a handle section 101 at its proximal end, and a pivot section 140 intermediate the working shaft section 174 and the handle section 101. The handle section 101 may include a first handle 102 and a second handle 122, as will be discussed in more detail below.

Figure 2:
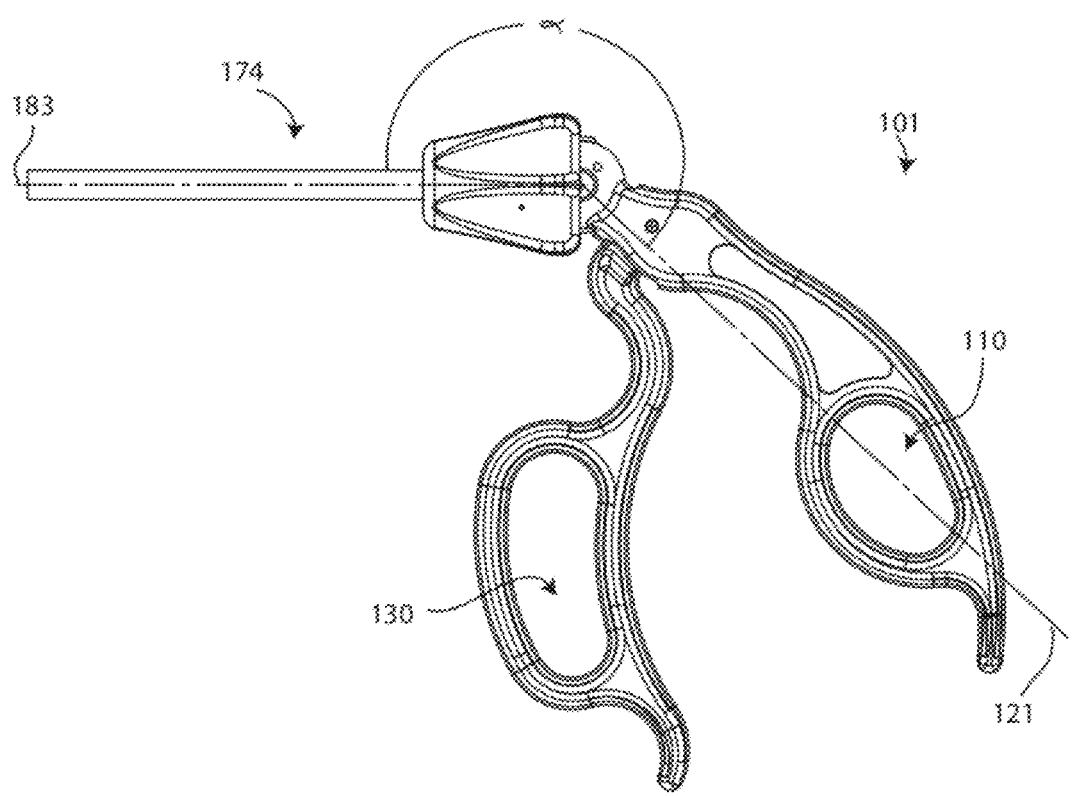
FIG. 2 is a side view of the surgical instrument of FIG. 1 with the handles of the surgical instrument in a "drop-down" position.

FIG. 2 shows a side view of the surgical instrument 100 of FIG. 1 with the handle section 101 adjusted in a "drop-down" position relative to a longitudinal axis 183 of the working shaft section 174. The surgeon can use this handle orientation for high precision activities with his or her fingers in the finger loops 110, 130 to give the surgeon more precise control over an end effector (not shown) disposed at the distal end of the working shaft 182. It is to be understood, that the surgical instruments disclosed herein can be used with any end effector, including, but not limited to: grasping jaws, dissectors, suture passers, staplers, tissue cutters, as well as any other end effector known in the art. Moreover, in some embodiments of the present disclosure, adjusting the angular position of the handle section 101 relative to the working shaft section 174 will not affect the end effector. For example, if the end effector is grasping jaws, then adjusting the angular position of the handle section 101 relative to the working shaft section 174 will not cause the grasping jaws to open, close, rotate or otherwise move in any substantial manner. Moreover, the mechanical advantage of the grasping jaws would remain substantially constant as the handle section 101 pivots. The range of motion of the jaws, as well as the range of forces that can be applied to the jaws by the surgeon, would also remain substantially constant as the handle section 101 pivots. In other words, these embodiments allow for the ergonomic adjustment of the handle section 101 to improve the surgeon's comfort without interfering with the normal operation of the end effector. In other embodiments, adjusting the angular position of the handle section 101 relative to the working shaft section 174 will not "substantially" affect the end effector. In other words, the end effector will substantially remain in the same functional state as the handle section 101 pivots, or will not deviate from the same functional state in an unsatisfactory manner, as the handle section 101 pivots.

Figure 3:
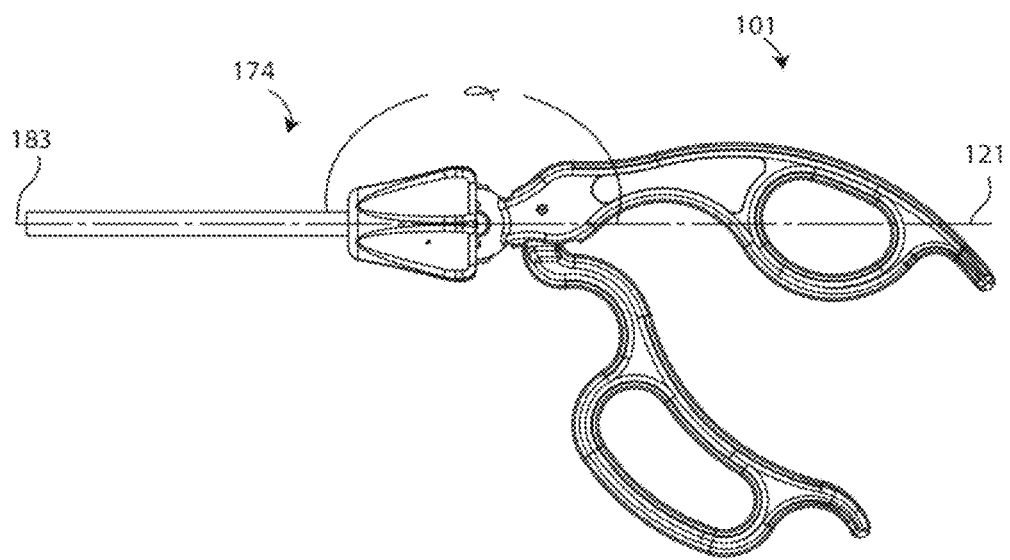
FIG. 3 is a side view of the surgical instrument of FIG. 1 with the handles of the surgical instrument in an "in-line" position.

FIG. 3 shows a side view of the surgical instrument 100 of FIG. 1 with the handle section 101 adjusted in an "in-line" position relative to the longitudinal axis 183 of the working shaft section 174. This handle orientation is similar to traditional "in-line" laparoscopic instruments such as needle holders. In some procedures, the "in-line" orientation may combine the best of both the "drop-down" and "in-line" configurations where the finger loops are still available for use in high precision tasks, such as grasping and positioning a needle, while also allowing the surgeon to grasp the handles in other ergonomic ways to perform different tasks that do not require as much precision, such as manipulating the needle inside of the patient.

Figure 4:
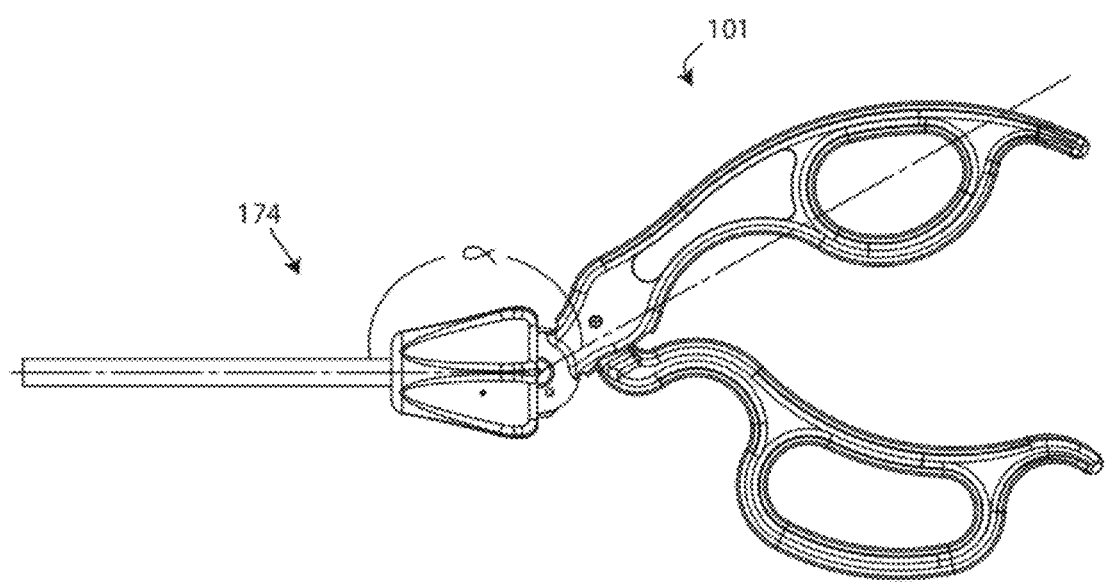
FIG. 4 is a side view of the surgical instrument of FIG. 1 with the handles of the surgical instrument in an "up-angled" position.

FIG. 4 shows a side view of the surgical instrument 100 of FIG. 1 with the handle section 101 adjusted in an "angled-up" position relative to the working shaft section 174. This handle position orientation may provide the surgeon an ergonomically viable interface with the instrument 100 in the face of awkward approach angles to the patient, as dictated by the variable and unpredictable requirements of surgery.

FIGS. 2-4 illustrate a reference system for measuring an angle α formed between the working shaft section 174 and the handle section 101. The reference system includes the longitudinal axis 183 corresponding to the working shaft section 174, a handle section axis 121 corresponding to the handle section 101, and an angle α defining the angular relationship between the longitudinal axis 183 and the handle section axis 121. Referring to FIG. 3, the handle section axis 121 may be defined when the handle section 101 is positioned in the "in-line" position. For example, when the handle section 101 is in the "in-line" position, the handle section axis 121 may be parallel to, or in-line with, the longitudinal axis 183. In some embodiments of the present disclosure, when the handle section axis 121 is parallel with the longitudinal axis 183, then the angle α corresponds to 0°, as seen in FIG. 3. If the handle section 101 is raised above the "in-line" position into an "angled-up" position, then the angle α is positive, as shown in FIG. 4. If the handle section 101 is lowered from the "in-line" position into a "drop-down" position, then the angle α is negative, as illustrated in FIG. 2. However, it is to be understood that other reference systems or ways of measuring a can be used herein without departing from the spirit or scope of the present disclosure.

In some embodiments, the handle section 101 may have a limited pivot range with respect to the working shaft section 174 that is defined by an angle $\alpha_{max}$ and an angle $\alpha_{min}$. In these embodiments, the handle section 101 can pivot upward until the handle section 101 reaches $\alpha_{max}$, at which point the handle section 101 is prevented from pivoting upward any further. Likewise, the handle section 101 can pivot downward until the handle section 101 reaches $\alpha_{min}$, at which point the handle section is prevented from pivoting downward any further. Thus, the pivot range of the handle section 101 may be limited to angles which lie between $\alpha_{max}$ and $\alpha_{min}$. In certain embodiments, the handle section 101 can be selectively positioned and maintained in an infinite number of angled positions within the pivot range defined by the maximum angle $\alpha_{max}$ and the minimum angle $\alpha_{min}$. In other embodiments, the handle section 101 can be selectively positioned and maintained in multiple discrete angled positions within the pivot range between $\alpha_{max}$ and $\alpha_{min}$. In yet other embodiments, the handle section 101 can be selectively positioned and maintained in three discrete angled positions within the pivot range between $\alpha_{max}$ and $\alpha_{min}$. In a particular embodiment, the handle section 101 can be selectively positioned and maintained in three discrete angled positions corresponding to about −35°, 0°, and 35°.

In some embodiments, the pivoting range of the handle section 101 may not be limited between a maximum angle $\alpha_{max}$ and/or a minimum angle $\alpha_{min}$. For example, some embodiments may have a maximum angle $\alpha_{max}$ that is any number between 0° and 180° and/or a minimum angle $\alpha_{min}$ that is any number between 0° and −180°. In one particular embodiment, the maximum angle can be any number between 0° and 90° and the minimum angle can be any number between 0° and −90°. In a preferred embodiment, the maximum angle is about 35° and the minimum angle is about −35°.

In a method of use, a practitioner may unlock the pivot section 140, select an angle position, rotate the handle section 101 relative to the working shaft section 175, until the desired angle position is reached, and relock the pivot section 140.

Figure 5:
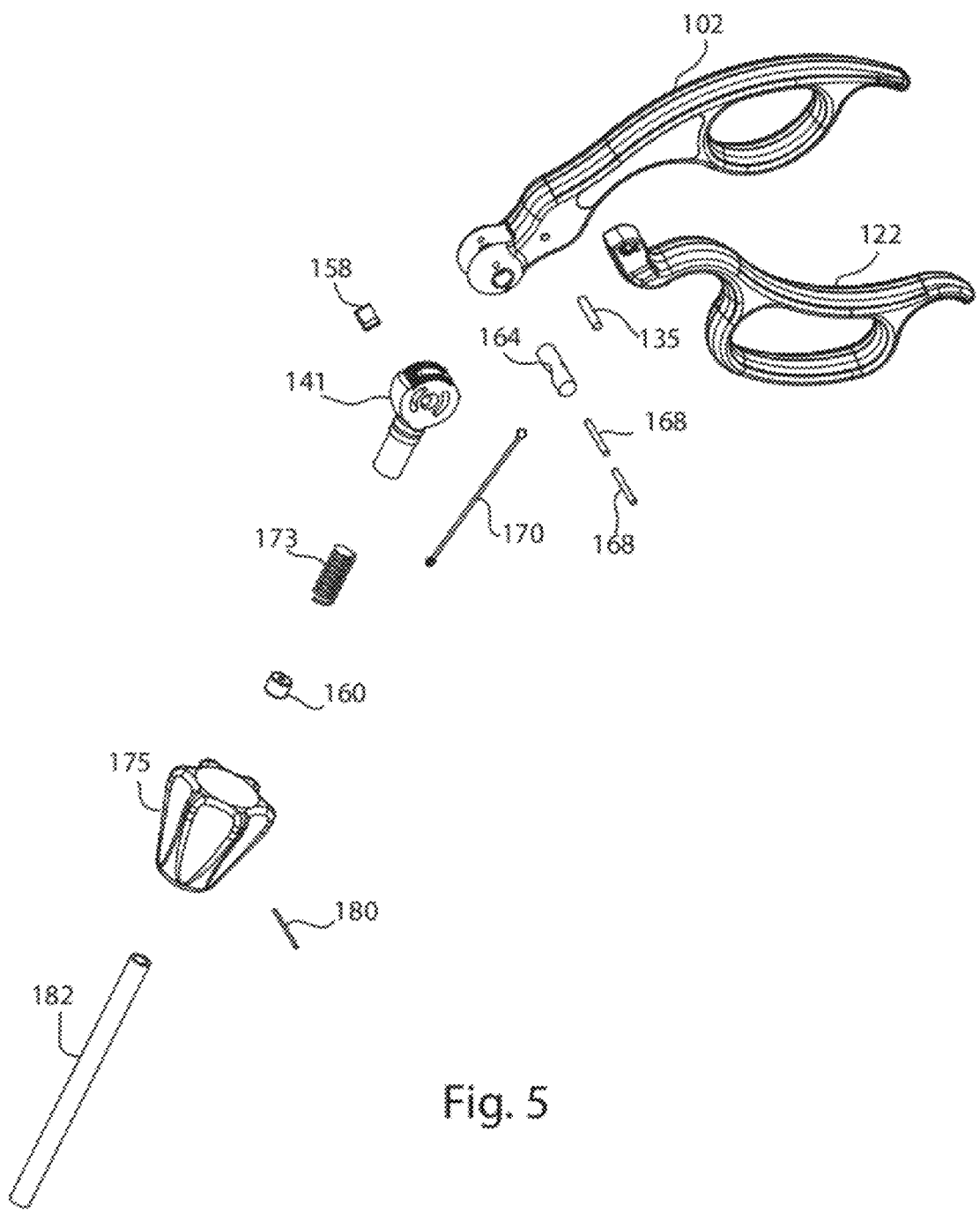
FIG. 5 is an exploded view of the surgical instrument of FIG. 1.

FIG. 5 shows an exploded view of the surgical instrument 100 with its various components. FIGS. 6A-13C illustrate the individual components of FIG. 5 in greater detail. A detailed description of the structure and features for each individual component will be given in a generally proximal to distal direction with reference to FIGS. 6A-13C. A detailed description of how each of the individual components interrelate with one another will then be given, along with the functional relationships between each component. Methods of using the surgical instrument 100 will also be given to illustrate how a surgeon can utilize the surgical instrument 100 to achieve greater ergonomic postures during surgery.

Figure 6A:
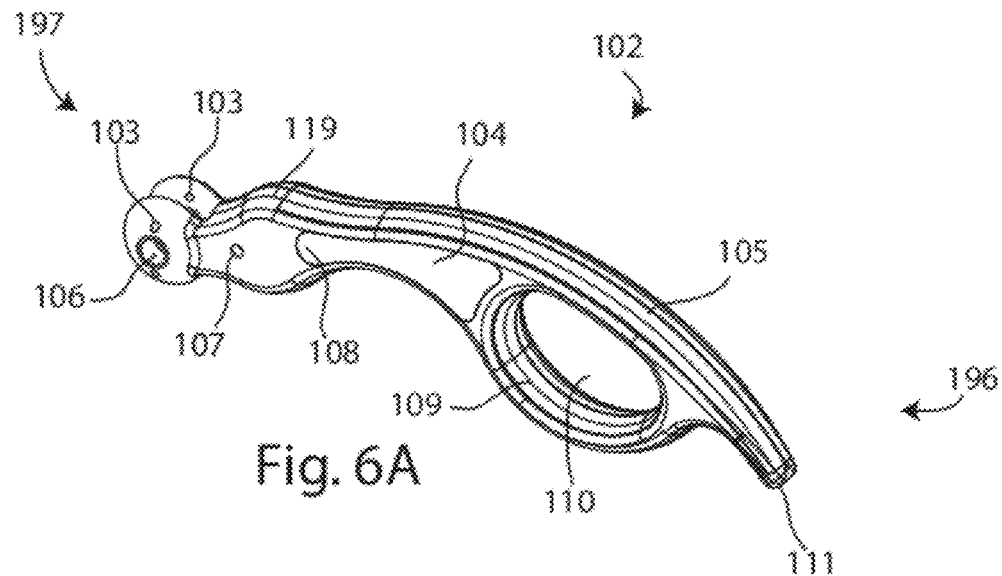
FIG. 6A is an isometric view of a first handle according to one embodiment of the present disclosure.
Figure 6B:
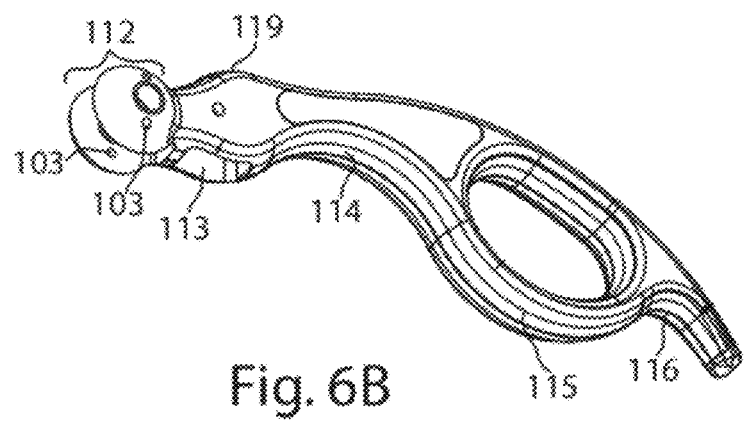
FIG. 6B is another isometric view of the first handle of FIG. 6A.
Figure 6C:
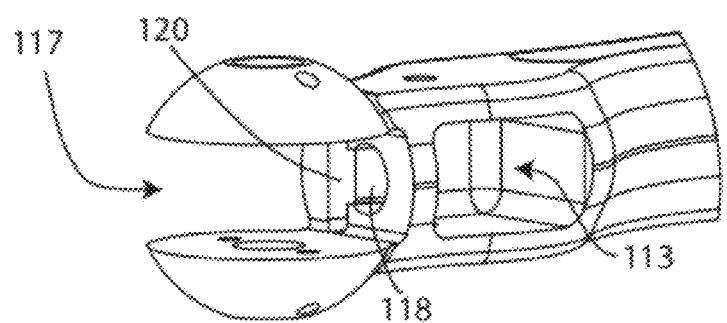
FIG. 6C is an enlarged isometric view of the distal end of the first handle of FIGS. 6A and 6B.

FIGS. 6A-6C show various isometric views of a first handle 102, according to one embodiment of the present disclosure. The first handle 102 has a proximal end 196 and a distal end 197. The first handle 102 can have a top surface 105, a bottom surface 115, and two side surfaces 104. The top surface 105 can have a spatulate leaf shape and/or curve downward in the distal to proximal direction to better conform to the surgeon's palm. In some embodiments, the top surface 105 can have a radius of curvature, or substantially lie along a radius of curvature. In some embodiments, the radius of curvature can be between about 2 and 4 inches. In other embodiments, the radius of curvature can be between about 2.5 inches and 3.5 inches. In a particular embodiment, the radius of curvature is about 2.9 inches.

The top surface 105 of the first handle 102 may have a convex or rounded shape in the lateral direction between the two side surfaces 104 of the first handle 102. The top surface 105 is preferably shaped to be substantially wide enough between the two side surfaces 104 to provide adequate comfort to the surgeon's palm by providing sufficient surface contact area between the top surface 105 and the surgeon's palm to reduce or eliminate "hot spots" from forming on the surgeon's palm. The top surface 105 can have a maximum width and a minimum width in the lateral direction between the two side surfaces. In some embodiments, the minimum width of the top surface is located closer to the distal end of the first handle and the maximum width of the top surface is located closer to the proximal end of the first handle. In some embodiments the minimum width is between about 0.25 inches and about 0.75 inches. In a particular embodiment, the minimum width is about 0.5 inches. In some embodiments, the maximum width is between about 0.5 inches and about 1.25 inches. In one embodiment, the maximum width is about 0.88 inches. The location of the minimum width of the top surface can be chosen to correspond to the area of the top surface 105 that the surgeon's thumb traverses when the surgeon switches between a "finger loop" grip style and a "palm" grip style. Having the minimum width of the top surface in this area of the top surface 105 can allow the surgeon to more easily switch between the "finger loop" grip style and the "palm" grip style because the smaller width makes it easier for the surgeon's thumb to traverse this area of the handle.

The top surface 105 may include a raised surface portion 119 to provide extra support for the surgeon's fingers or thumb in various different gripping styles. Moreover, the side surfaces 104 may include a thumb or finger rest area 108 formed on or into the side surfaces 104 to provide extra support for the surgeon's thumb when engaged along the side surface 104. The first handle 102 may have one or more finger loop holes 110 to receive one or more fingers during procedures requiring greater precision. The finger loop hole contact surface 109 may be convex in shape and wide enough to avoid or eliminate any "hot spots" from occurring on the surgeon's fingers during extended hours of operation. The first handle 102 can have a projection portion 111 at the proximal end of the first handle 102. The projection portion 111 may provide greater surface area to interact with the surgeon's palm against the top surface 105, and also provide a concave-shaped projection recess portion 116 to interact with the surgeons fingers on the opposite side. In some embodiments, the projection portion 111 can include an electrical connector to receive external input. The first handle 102 can also have a bottom surface 115 and a bottom surface recess area 114 having a concave shape configured to interact with one or more of the surgeon's fingers as needed.

Any or all of the surfaces of the first handle 102 may include a comfort material (not shown) attached to one or more of the surfaces of the first handle 102, such as a soft rubber, polymer, or silicone. The comfort material may be applied to the first handle 102 after manufacture, or the comfort material may be integrally formed or molded to the first handle 102 during manufacture by any suitable manufacturing processes including, but not limited to, bonding or overmolding.

The distal end of the first handle 102 may include a head portion 112 for receiving a suitably shaped pivot housing 141 into a pivot housing slot 117. The head portion 112 may have stop pin holes 103 formed through both sides of the head portion 112 for receiving stop pins 168, as will be discussed in further detail below. The head portion 112 can have a pivot pin hole 106 formed through the head portion 112 configured to receive a pivot pin 164. The first handle 102 may include a pin hole 107 formed through, or substantially through, the side surfaces 104 of the first handle 102 and configured to receive a pivot pin 135 to pivotably secure a second handle 122. In this embodiment, the surgical instrument 100 includes a dual pivot design with a first pivot connecting the handle section 101 to the working shaft section 174, and a second pivot connecting the second handle 122 to the first handle 102. Moreover, the first and second pivots are not coaxial with each other in this embodiment.

Referring to FIGS. 6B-6C, the first handle 102 may include a receiver slot 113 configured and shaped to receive the head portion 127 of a suitable second handle 122, as will be discussed in further detail below. FIG. 6C illustrates the pivot housing slot 117 configured to receive a suitable pivot housing 141 in greater detail. FIG. 6C also illustrates an actuator aperture 118 formed within the first handle 102 proximal to the head portion 112 and shaped to allow an actuator 170 to be disposed therein.

Figure 7A:
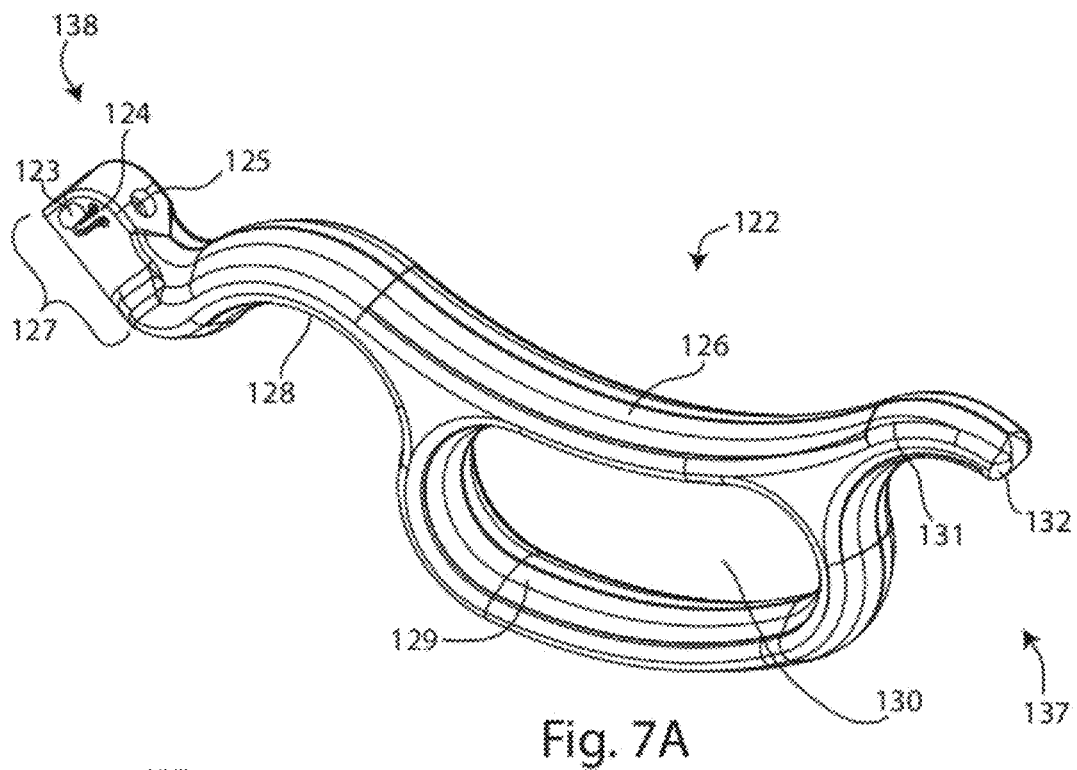
FIG. 7A is an isometric view of a second handle according to one embodiment of the present disclosure.
Figure 7B:
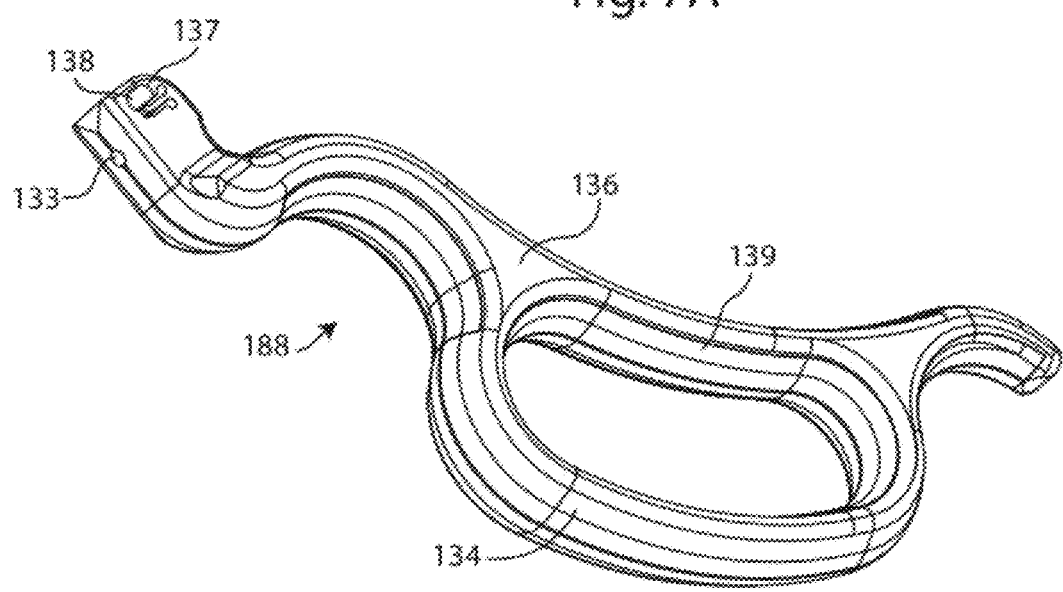
FIG. 7B is an isometric view of the second handle of FIG. 7A.

Referring now to FIGS. 7A-7B, a second handle 122 in accordance with one embodiment of the present disclosure is shown. The second handle 122 can have a proximal end 137 and a distal end 138. The second handle 122 can also have a top surface 126, a bottom surface 134, and two side surfaces 136. Each of the aforementioned surfaces may have a generally rounded or convex shape to increase comfort. The top surface 126 of the second handle 122 may have a slight "S-shaped" curvature formed therein moving in the distal to proximal direction. The distal end of the second handle 122 may include a head portion 127 configured to interact with the receiver slot 113 of the first handle 102, as shown in FIGS. 6A-6C.

The second handle 122 may have one or more finger loop holes 130 configured to receive one or more of the surgeon's fingers during procedures that require greater precision. The inner contact surface 129 of the finger loop hole 130 may have a rounded or convex shape to comfortably engage the fingers of the surgeon.

The second handle 122 may have at least one finger contact surface. Moreover, the at least one finger contact surface can be configured to substantially lie along a radius of curvature. The radius of curvature can be between about 1.5 and 3.5 inches in some embodiments. In other embodiments, the radius of curvature may be between about 2 inches and 3 inches. In a particular embodiment, the radius of curvature is about 2.5 inches.

The second handle 122 can have a finger loop 130 defining a first finger contact surface 139 configured to receive the surgeon's ring finger and middle finger, a projection 132 configured to receive the surgeon's pinky finger, and a recess portion 188 having a third finger contact surface 128 configured to receive the surgeon's index finger. Moreover, one or more of these finger contact surfaces can substantially lie along a radius of curvature. For example, the first and second finger contact surfaces can substantially lie along a radius of curvature of about 2.5 inches and the third finger contact surface can be offset from the radius of the curvature of the first and second finger contact surfaces by about 0.0625 inches.

Any or all of the surfaces of the second handle 122 may include a comfort/grip-enhancing material (not shown) attached to one or more of the surfaces of the second handle 122, such as a soft rubber, polymer, or silicone material. The comfort/grip-enhancing material may be applied to the second handle 122 after manufacture, or alternatively the comfort/grip-enhancing material may be integrally formed or molded to the second handle 122 during manufacture by several manufacturing processes, such as, bonding or overmolding.

Continuing with FIGS. 7A-7B, the head portion 127 of the second handle 122 can have a latch release cavity 123 formed through the head portion 127. The latch release cavity 123 may have an oblong or elongated oval shape configured to receive a second handle pivot pin 135 to allow the second handle pivot pin 135 to move translationally within the latch release cavity 123. The latch release cavity 123 can have a spring detent 124 just below the latch release cavity 123 to help control and bias the translational movement of the second handle pivot pin 135, as will be discussed in greater detail below. The head portion 127 can have an actuator bore 133 formed through the head portion 127 and in communication with an actuator connection recess 125 on the opposite side of the head portion 127.

In other embodiments, the second handle 122 may comprise an alternative control member such as a trigger, a button, a lever, a truncated handle or any other structure suitable for a surgical instrument. In some embodiments, the second handle 122 may be omitted entirely.

Figure 8A:
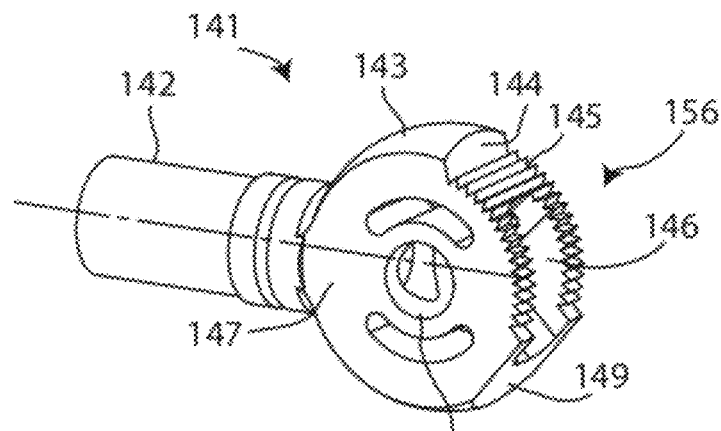
FIG. 8A is an isometric view of a pivot housing according to one embodiment of the present disclosure.
Figure 8B:
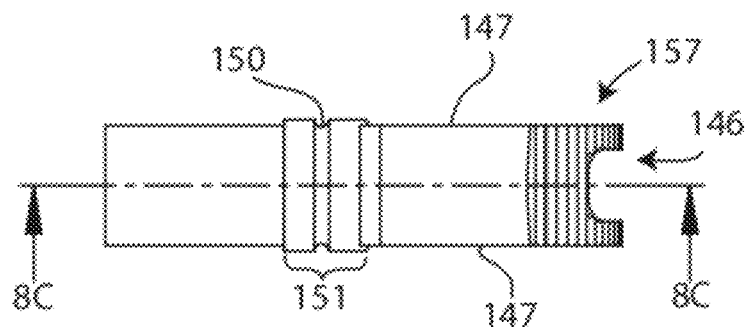
FIG. 8B is a top view of the pivot housing of FIG. 8A having a section line 8C-8C.
Figure 8C:
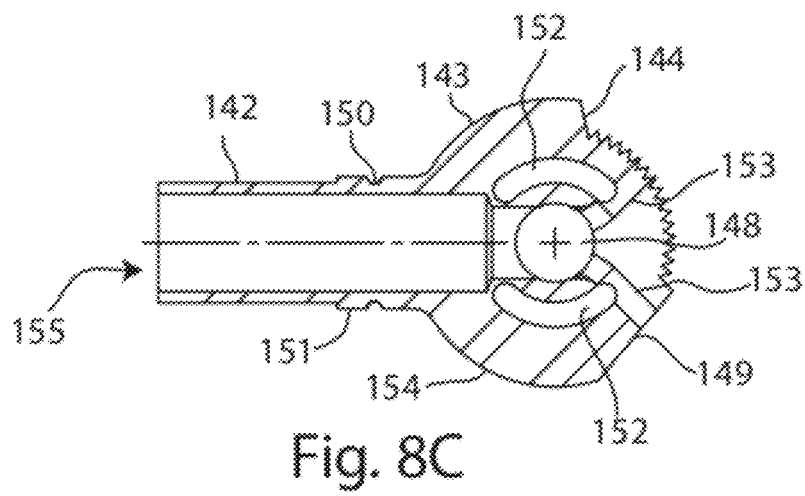
FIG. 8C is a cross-sectional side view of the pivot housing of FIG. 8B, taken along the section line 8C-8C in FIG. 8B.

FIGS. 8A-8C show a pivot housing 141, in accordance with one embodiment of the present disclosure. The pivot housing 141 may include a hollow shaft 142 at its distal end and a pivot head portion 156 at its proximal end. The pivot head portion 156 may have a top surface 143, a bottom surface 154, side surfaces 147, a top angled surface 144, and a bottom angled surface 149. The top surface 143 and the bottom surface 154 may have partially spherical shapes configured to receive a suitable rotation knob 175 and allow the rotation knob 175 to rotate freely about the pivot head portion 156. The pivot head portion 156 may include a pivot pin hole 148 formed through the pivot head portion 156 between the sides 147. Additionally, the pivot head portion 156 may include stop pin slots 152 formed through the pivot head portion 156 having elongated and curved oval shapes. The pivot head portion 156 may also include one or more locking teeth 145 formed in a proximal surface of the pivot head portion 156.

With reference to FIG. 8B, the hollow shaft 142 may have a larger diameter portion 151 wherein the larger diameter portion 151 may include an annular groove 150 formed therein. The annular groove 150 may be shaped and configured to receive a retaining pin 180 to allow the rotation knob 175 to rotate freely about the pivot housing 141, while keeping the rotation knob 175 from moving translationally with respect to the working shaft 182. The hollow shaft 142 can have an inner bore 155 shaped to receive a suitable restoring spring 173. The inner bore 155 may be in communication with the pivot pin hole 148 and a proximal opening 146 in the pivot head portion 156. The proximal opening 146 may open wider moving in the distal to proximal direction with diverging top and bottom surfaces 153.

FIG. 9 shows a locking member 158 in accordance with one embodiment of the present disclosure. The locking member 158 may have a locking surface 163 including one or more locking teeth 159 formed in a surface of the locking member 158 and configured to engage the locking surface 157 of the pivot housing 141, which can also include teeth 145, in some embodiments.

FIG. 10 shows a connector 160 in accordance with one embodiment of the present disclosure. The connector 160 can have a bore 161 formed through the connector 160 and a radially chamfered surface formed in one end of the connector 160.

FIGS. 11A-11C show various views of a pivot pin 164 in accordance with one embodiment of the present disclosure. The pivot pin 164 may have a guide hole 169 formed through the center of the pivot pin 164. The guide hole 169 can restrain the actuator 170 along the centerline of the joint as the handle section 101 pivots relative to the working shaft section 182. The guide hole 169 may have a distal end 166 and a proximal end 167 as shown in FIG. 11C. The distal end 166 of the guide hole 169 can be smaller in diameter than the proximal end 167 of the guide hole 169. The distal end 166 of the guide hole 169 can have a chamfered surface. The proximal end 167 of the guide hole 169 can also have a chamfered surface 165 which may be larger than the chamfered surface of the distal end 166 of the guide hole 169, as shown in FIGS. 11B and 11C.

FIG. 12 shows one embodiment of an actuator 170 that may be used in the present disclosure. The actuator 170 can have a distal connector 171 at its distal end and a proximal connector 172 at its proximal end. The distal connector 171 may have a partially spherical shape and a hollow center, as can be seen in FIG. 12. The proximal connector 172 may have a solid spherical shape. However, it is to be understood that the proximal connector 172 and the distal connector 171 may assume any shape that can provide adequate operation of the actuator 170 according to the present disclosure. The actuator 170 may be formed of a flexible material to allow the actuator 170 to bend along its length when the handle section 101 pivots relative to the working shaft section 174. The actuator 170 can preferably be formed of a material that substantially resists tension forces that are applied to the actuator 170 between the distal connector 171 and proximal connector 172. In one embodiment the actuator 170 may be an elongated flexible member or a cable. In other embodiments, the actuator 170 may be made of a rigid or semi-rigid segmented linkage that can be restrained to the centerline of the joint. For example, the actuator 170 may be two rigid portions connected by a flexible portion disposed between the two rigid portions.

FIGS. 13A-13C show one embodiment of a rotation knob 175 in accordance with the present disclosure. The rotation knob 175 can have an outer surface that is larger in diameter at its proximal end 178 and smaller in diameter at its distal end 177. The outer surface of the rotation knob 175 can be sized and shaped to engage with a surgeon's finger or thumb to facilitate rotation of the rotation knob 175. For example, the rotation knob 175 can have one or more ribs 181 and one or more depressions 176 formed in the outer surface of the rotation knob 175. The spacing of the ribs 181 and the size and depth of the depressions 176 are preferably sized to fit the width and shape of the average surgeon's fingers and/or thumb. However, it is to be understood that the size and shape of the depressions 176, as well as the number and spacing of the ribs 181, may be varied in any fashion or tailored in any way so as to fit any size finger or thumb. The rotation knob 175 is preferably located close enough to the handle section 101 to allow the surgeon to rotate the rotation knob 175 with one hand. For example, the surgeon may grasp the handle section 101 with one hand and use the thumb or index finger of the same hand to rotate the rotation knob 175. With reference to FIG. 13C, the rotation knob 175 may have an inner chamber 179 formed within the rotation knob 175 and shaped to receive a suitable pivot housing 141, as shown in FIG. 5 and FIGS. 8A-8C.

Referring back to FIG. 5, a working shaft 182 may be engaged with the rotation knob 175 such that rotating the rotation knob 175 will rotate the working shaft 182 and orient an end effector (not shown) disposed at the distal end of the working shaft 182. In other embodiments, the working shaft 182 may not be fixedly attached to the rotation knob 175. For example, the rotation knob 175 may be fixedly attached to a working rod (not shown) which may run through the working shaft 182 with the working rod connected to the end effector. In this embodiment, rotating the rotation knob 175 will rotate the working rod disposed within the working shaft 182 in order to rotate and Orient the end effector. Furthermore, rotation of the end effector may be prevented, under certain circumstances, by means that are known in the art. For example, rotation of the end effector may be prevented while tensile and/or compression loads are transmitted through the working shaft section 174. Moreover, any of the surgical instruments disclosed herein may also include ratcheting mechanisms to lock the end effector in one or more positions. For example, if the end effector is a set of jaws, actuating the ratcheting mechanism may lock the jaws or keep the jaws from opening wider. The ratcheting mechanism may provide discrete "locked" positions, or alternatively, the ratcheting mechanism may provide an infinite number of "locked" positions, as will be discussed in greater detail below.

Continuing with FIG. 5, a retaining pin 180 may be inserted through an aperture formed in the side of the rotation knob 175. The retaining pin 180 may project, at least partially, into the inside of the inner chamber 179 of the rotation knob 175 and engage an annular groove 150 formed within the larger diameter portion 151 of the hollow shaft 142 of the pivot housing 141. In this configuration, the retaining pin 180 will not permit the rotation knob 175 to move translationally with respect to the longitudinal axis 183 of the working shaft 182, yet the retaining pin 180 will allow the rotation knob 175 to rotate freely about the longitudinal axis of the working shaft 182.

FIG. 5 shows a restoring spring 173 that can be used in some embodiments of the present disclosure to keep the actuator 170 under constant tension. The actuator 170 may be threaded through the bore 161 of the connector 160 such that the distal connector 171 of the actuator 170 engages the chamfered surface 162 of the connector 160 when the actuator 170 is pulled in the proximal direction by the surgeon. The actuator 170 can be threaded through the restoring spring 173, the inner bore 155 of the pivot housing 141, the guide hole 169 of the pivot pin 164 disposed within the pivot pin hole 148 of the pivot housing 141, and through the actuator bore 133 of the second handle 122 such that the proximal connector 172 of the actuator 170 can be disposed within the actuator connection recess 125 of the second handle 122. The restoring spring 173 may be disposed within the inner bore 155 of the hollow shaft 142 of the pivot housing 141. The restoring spring 173 can exert a force on the proximal end of the connector 160 to move the connector 160 in the distal direction and keep the actuator 170 under constant tension. Accordingly, if the second handle 122 is "sprung," then the second handle 122 has a natural or normal position to which it returns when the second handle 122 is at rest. A "sprung"

second handle 122 may be useful when the instrument 100 is used in a "palm" grip style. In this configuration, the "sprung" handle provides a natural resistance to the surgeon's hand that allows the surgeon to retain the handle section 101 with the surgeon's palm independent of the finger loops. However, it will be noted that other embodiments can have second handles 122 that are "unsprung." In this configuration, the second handle 122 may be at rest in any position when the second handle 122 is not acted upon by the surgeon.

The pivot head portion 156 of the pivot housing 141 may be inserted into the pivot housing slot 117 of the first handle 102 such that the pivot pin hole 148 of the pivot housing 141 and the pivot pin hole 106 of the first handle 102 are in alignment. A pivot pin 164 may then be inserted through the pivot pin hole 106 of the first handle 102 and into the pivot pin hole 148 of the pivot housing 141. The guide hole 169 of the pivot pin 164 may be oriented such that the distal end 166 of the guide hole 169 faces toward the working shaft 182 and the proximal end 167 of the guide hole 169 faces the handle section 101. Stop pins 168 may also be inserted through the stop pin holes 103 of the first handle 102 and into the stop pin slots 152 of the pivot housing 141.

Continuing with FIG. 5, the head portion 127 of the second handle 122 may be inserted into the second handle receiver slot 113 of the first handle 102 and secured to the first handle 102 by a pivot pin 135 inserted through the pin hole 107 of the first handle 102 and through the latch release cavity 123 of the second handle 122. The force of the spring detent 124 combined with the constant tension of the actuator 170 will keep the pivot pin 135 in the proximal end of the latch release cavity 123 when the second handle 122 is at rest (see FIG. 15). Furthermore, a locking member 158 can be inserted into the cavity 120 of the first handle 102 (see FIG. 6C) with the locking teeth 159 of the locking member 158 facing distally so as to engage the locking teeth 145 formed in the surface of the pivot housing 141. The proximal end of the locking member 158 may be attached to a surface of the head portion 127 of the second handle 122 disposed within the second handle receiver slot 113 of the first handle 102. The locking member 158 may be fixedly or rigidly engaged with the head portion 127, or a surface of the head portion 127, of the second handle 122. In other embodiments, there may be a mechanical junction between the second handle 120 and the locking member 158. Alternatively, or in addition to, the locking member 158 may be pivotably connected to the head portion 127 of the second handle 122. The locking member 158 may also be spring biased to aid the engagement or the disengagement of the locking teeth 159 of the locking member 158 with the locking teeth 145 of the pivot housing 141.

Figure 14A:
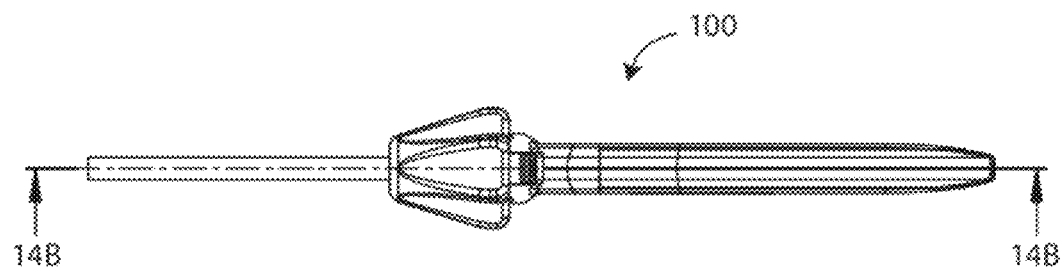
FIG. 14A is a top view of the surgical instrument shown in FIG. 3 having a section line 14B-14B.
Figure 14B:
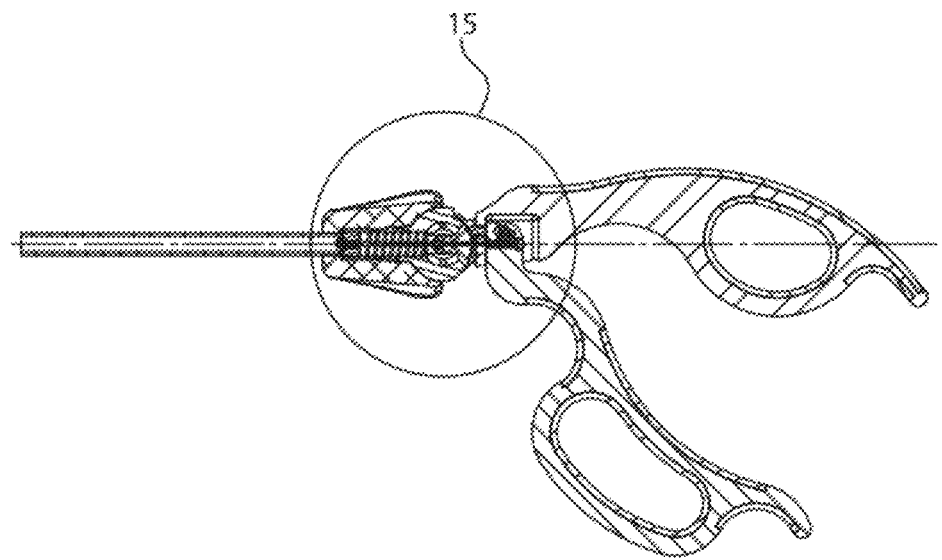
FIG. 14B is a cross-sectional side view of the surgical instrument of FIG. 14A, taken along the section line 14B-14B in FIG. 14A.
Figure 15:
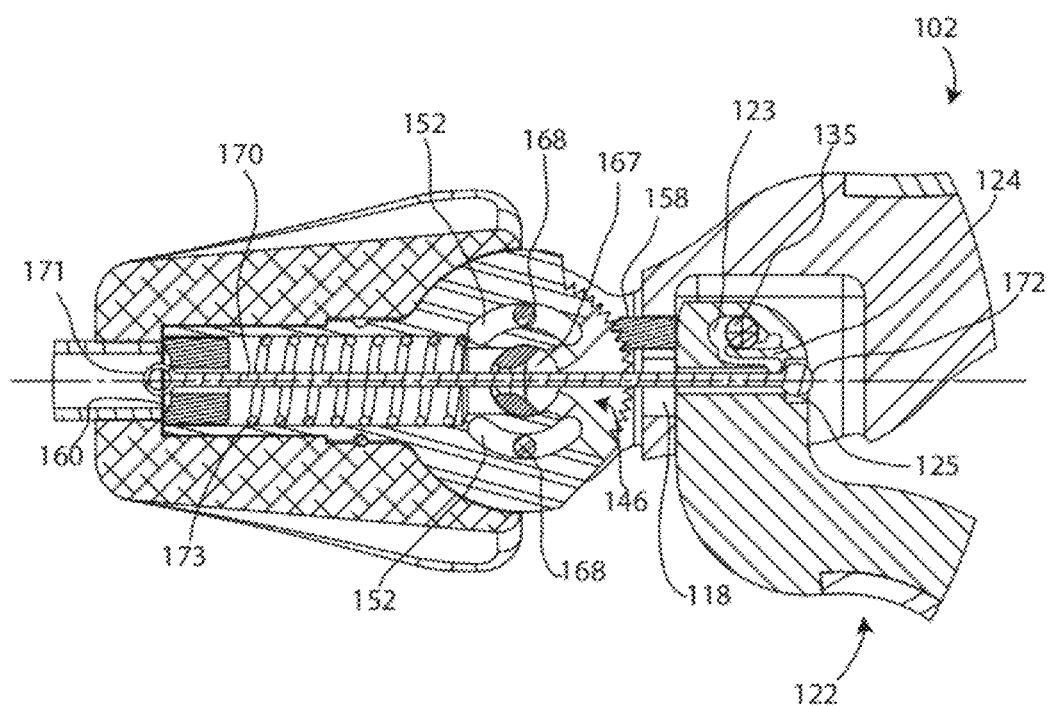
FIG. 15 shows an enlarged view of the encircled area in FIG. 14B.

Referring to FIGS. 14A-15, the operation of the surgical instrument 100 will be explained in more detail along with the functional relationships between the various components of the surgical instrument 100. At rest, the restoring spring 173 pushes distally on the connector 160 to keep the actuator 170 under constant tension. Furthermore, the spring detent 124 biases the second handle pivot pin 135 toward the proximal and of the latch release cavity 123. The locking teeth 159 of the locking member 158 can be engaged with the locking teeth 145 of the pivot housing 141 such that the handle section 101 is not free to pivot with respect to the working shaft section 174.

In a method of use, a practitioner may disengage the locking member 158 to allow the handle section the pivot, pivot the handle section to a desired angle position, and reengage the locking mechanism to prevent the handle section from pivoting.

In operation, a surgeon may grasp the handle section 101 with his or her hand and squeeze the second handle 122 to move the second handle 122 closer to the first handle 102. The second handle will tend to pivot in a counterclockwise direction around the second handle pivot pin 135, pulling the actuator 170 toward the surgeon and engaging an end effector (not shown) connected to the distal connector 171 of the actuator 170. Pulling the actuator 170 in this fashion creates a tensile load down the actuator 170 which may be transferred to an inner shaft (not shown) connected to the distal connector 171 of the actuator 170 to operate the end effector. In other embodiments, the relative locations of the second handle pivot and 135 and an actuator connection recess 125 may be reversed such that compressing the handles together creates a compressive load down the working shaft and/or a linear motion away from the surgeon.

In a method of use, a practitioner may control an end effector by moving the first and second handles relative to each other to cause the actuator 170 to affect the end effector.

As seen in FIG. 15, the size and shape of the guide hole 167 in the pivot pin 164, along with the size and shape of the proximal opening 146 of the pivot housing 141, can allow the actuator 170 to bend upward or downward as the handle section 101 pivots upward or downward. In this embodiment, the actuator 170 defines an actuation path length between the second handle and the proximal end of an actuator target, such as a working rod (not shown), connected to an end effector (not shown). As the handle section 101 pivots relative to the working shaft section 174, the actuation path length remains substantially constant because the actuator 170 is restrained to the centerline of the joint through the pivot pin 164. Thus, pivoting the handle section 101 in either direction will not substantially move or otherwise affect the end effector. Moreover, the actuator 170 can be kept under constant tension by the restoring spring 173, independent of which ever pivot position the handle section 101 assumes.

Embodiments of the present disclosure allow the second handle 122 to control whether or not the handle section 101 can pivot. In these embodiments, the second handle 122 can be positioned in a first position to lock the pivot section 140 and prevent the handle section 101 from pivoting relative to the working shaft section 174. The second handle 122 can also be positioned in a second position to unlock the pivot section 140 and allow the handle section 122 to pivot relative to the working shaft section 174.

In one embodiment, the second handle 122 can control whether or not the handle section 101 can pivot utilizing a system including a pivot pin 135, a latch release cavity 123 formed within the second handle 122, a spring detent 124 and a locking member 158 engaged with the second handle 122. The second handle 122 may be pivotably engaged to the first handle 102 by the pivot pin 135 disposed within the latch release cavity 123 of the second handle 102 threaded through the pin holes 107 formed in the first handle 102. At rest, the second handle 122 is in a first position with the spring detent 124 imposing a bias force upon the pivot pin 135 forcing the head portion 127 of the second handle 122 to move in the distal direction and the pivot pin 135 to move into the proximal end of the latch release cavity 123. The locking member 158 engaged with the second handle 122 may also move in the distal direction along with the head portion 127 of the second handle 122 to allow the pivot section 140 to lock.

To unlock the pivot section 140, the surgeon can apply and maintain a counterclockwise force on the second handle 122 to force the second handle 122 into a second position that will allow the pivot section 140 to unlock and permit the handle section 101 to pivot. With sufficient counterclockwise force on the second handle 122, the biasing force of the spring detent 124 is overcome allowing the head portion 127 of the second handle 122 to move in the proximal direction forcing the pivot pin 135 into the distal end of the latch release cavity 123. The locking member 158 engaged with the second handle 122 may also move in the proximal direction with the head portion 127 of the second handle 122 to allow the pivot section 140 to unlock.

In some embodiments, the pivot housing 141 includes a first locking surface 157 and the locking member 158 includes a second locking surface 163. The first and second locking surfaces can be any size, shape, or texture. The first and second locking surfaces can made from any suitable materials that will allow the first and second locking surfaces to interact with each other to lock the pivot section 140. For example, the first and second locking surfaces may be relatively smooth and made from frictional materials that allow the locking surfaces to frictionally engage with one another at any point and at any angle. For example, the first and second locking surfaces may be smooth and made of rubber, or a rubber-like material, such that when the first and second locking surfaces are pressed together frictional forces keep the pivot section 140 locked. It is to be understood that the term rubber, or rubber-like material, includes any naturally occurring or synthetic material exhibiting frictional properties suitable to substantially lock the pivot section 140. In this manner, the handle section can be selectively positioned and locked in an infinite number of angled positions relative to the longitudinal axis of the working shaft section over a range of angles defined by $\alpha_{max}$ and $\alpha_{min}$.

Some embodiments provide for an infinite number of different angled positions that the handle section 101 can assume in a single plane. In other embodiments, the handle section 101 can be angled in multiple planes with respect to the working shaft section 174. Thus, it is envisioned that a pivot joint section 140 having a multi-axial or poly axial articulation can be utilized. In other embodiments, the handle section 101 can be angled in multiple planes with respect to the working shaft section 174 utilizing a discrete number of different angle positions for one or more of the planes. In yet other embodiments, the handle section 101 can be angled in multiple planes with respect to the working shaft section 174 utilizing an infinite number of different angle positions for one or more of the planes. In each of these embodiments, it is envisioned that a similarly functioning latch component may be utilized to lock the pivot joint section in each of its respective planes of movement.

In other embodiments, the handle section 101 can be selectively positioned in multiple discrete angled positions relative to the longitudinal axis 183 of the working shaft section 174 over a range of angles defined by an angle $\alpha_{max}$ and an angle $\alpha_{min}$. In another embodiment, the handle section 101 can be selectively positioned in three discrete angled positions relative to the longitudinal axis 183 of the working shaft section 174. In a particular embodiment, the handle section 101 can be selectively positioned in 3 discrete angled positions corresponding to about 35°, 0°, and −35°.

In some embodiments, the first locking surface 157 of the pivot housing 141 and the second locking surface 163 of the locking member 158 may comprise one or more locking teeth 145, 159. In this embodiment, the locking teeth 145, 159 may interact with each other to lock the pivot section 140. In order to pivot the handle section 101 with respect to the working shaft section 174, the locking teeth 159 of the locking member 158 may be disengaged from the locking teeth 145 of the pivot housing 141. A surgeon may disengage the locking teeth 159 of the locking member 158 from the locking teeth 145 of the pivot housing 141 by rotating the second handle 122 in a clockwise direction, about the second handle pivot pin 135. Rotating the second handle 122 in the clockwise direction with enough force will overcome the spring bias of the spring detent 124 and force the second handle 122 to move translationally with respect to the pivot pin 135 such that the distal end of the latch release cavity 123 moves proximally toward the pivot pin 135 to receive the pivot pin 135 into the distal end of the latch release cavity 123. At this point, the head portion 127 of the second handle 122 has moved proximally enough to disengage the locking member 158 from the pivot housing 141 allowing the handle section 101 to pivot. The surgeon may continue to apply a clockwise force to the second handle 122 to keep the locking member 158 disengaged while he or she rotates the handle section 101 to the new desired angular position. The surgeon may then stop applying the clockwise rotational force to the second handle 122 and allow the spring bias of the spring detent 124 to force the second handle 122 to move back in the distal direction and allow the proximal end of the latch release cavity 123 to receive the second handle pivot pin 135. Once the second handle 122 moves back in the distal direction, the locking teeth 159 of the locking member 158 can engage the locking teeth 145 of the pivot housing 141, locking the handle section 101 in the desired angular position and preventing the handle section 101 from pivoting with respect to the working shaft section 174.

In some embodiments, the number of different angled positions the handle section 101 can assume can be dependent on the number, size, and shape of the locking teeth 145 of the pivot housing 141 and the locking teeth 159 of the locking member 158. For example, increasing the number of locking teeth 145 on the pivot housing 141 will result in a greater number of discrete angled positions that the handle section 101 can assume. However, increasing the number of locking teeth 145 on the pivot housing 141 may result in smaller locking teeth 145, 159 which may result in teeth that are not mechanically strong enough to the withstand forces applied to the teeth during normal operation of the surgical instrument 100.

In some embodiments, it may be desirable to limit how much the handle section 101 may pivot in relation to the working shaft section 174 of the surgical instrument 100. Stop pins 168 disposed within the stop pin slots 152 of the pivot housing 141 can be used to limit how far the handle section 101 may pivot. Continuing with FIG. 15, as the handle section 101 pivots in the upward direction the stop pins 168 will rotate counterclockwise in their respective stop pin slots 152, about the pivot pin 164. In this embodiment, if the surgeon continues to rotate the handle section 101 in the counterclockwise position, eventually the stop pins will contact the ends of their respective stop pin slots 152 preventing further rotation in the counterclockwise direction. Likewise, if the surgeon continues to rotate the handle section 101 in the clockwise direction, eventually the stop pins 168 will contact the opposite ends of their respective stop pin slots 152 preventing further rotation in the clockwise direction. Alternatively, or in addition thereto, the pivot housing 141 may include a top angled surface 144 and a bottom angled surface 149 which may act as "hard stops" to interact with complementary surfaces of the first handle 102 or the second handle 122 to prevent further rotation in either the clockwise or the counterclockwise direction.

Figure 16:
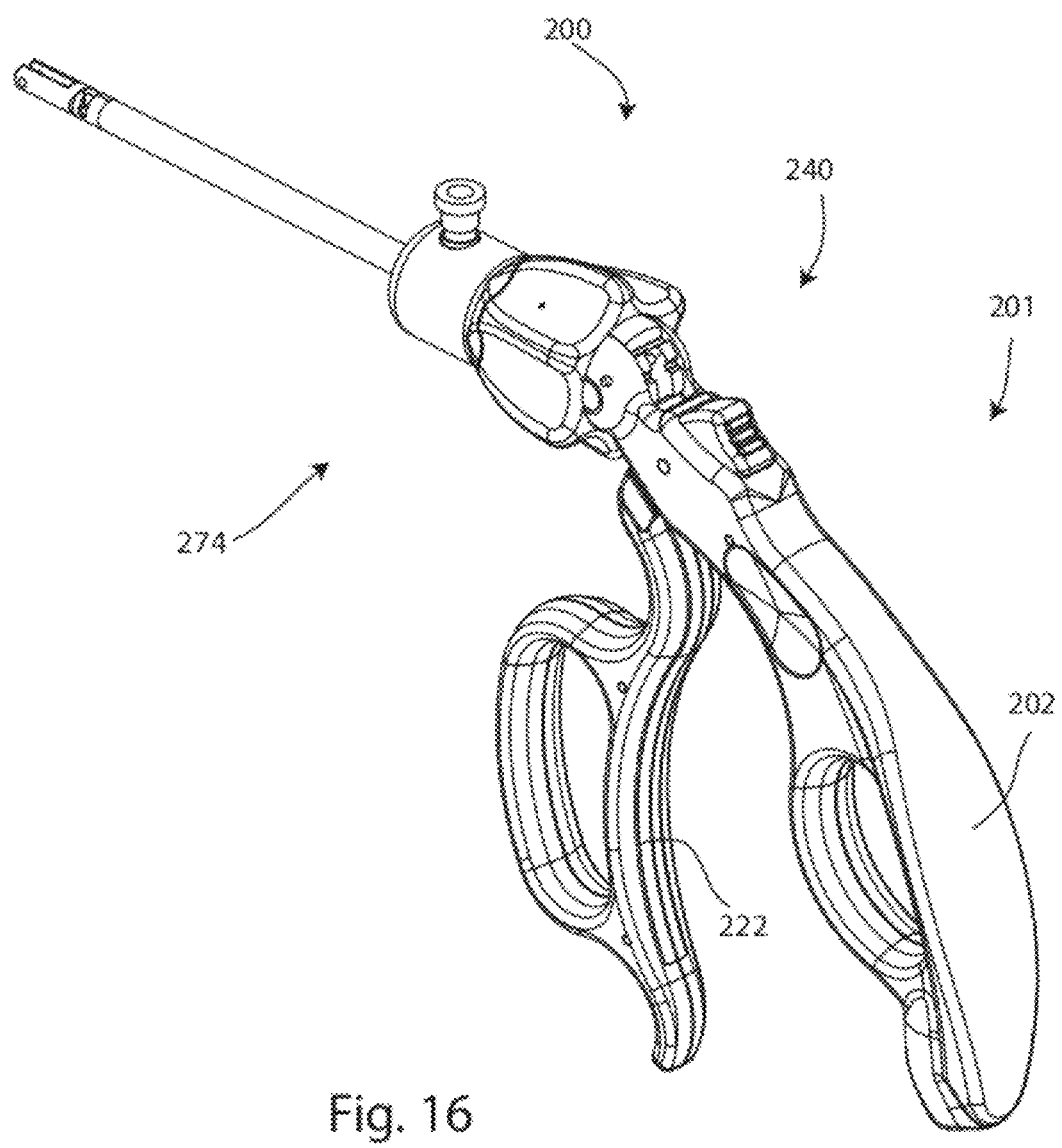
FIG. 16 is an isometric view of a surgical instrument with an adjustable handle section according to another embodiment of the present disclosure.

In FIGS. 16-43, a surgical instrument 200 in accordance with another embodiment of the present disclosure is illustrated. FIG. 16 shows an isometric view of a surgical instrument 200 having a working shaft section 274 at its distal end, a handle section 201 at its proximal end, and a pivot section 240 intermediate the working shaft section 274 and the handle section 201. The handle section 201 may include a first handle 202 and a second handle 222.

Figure 17:
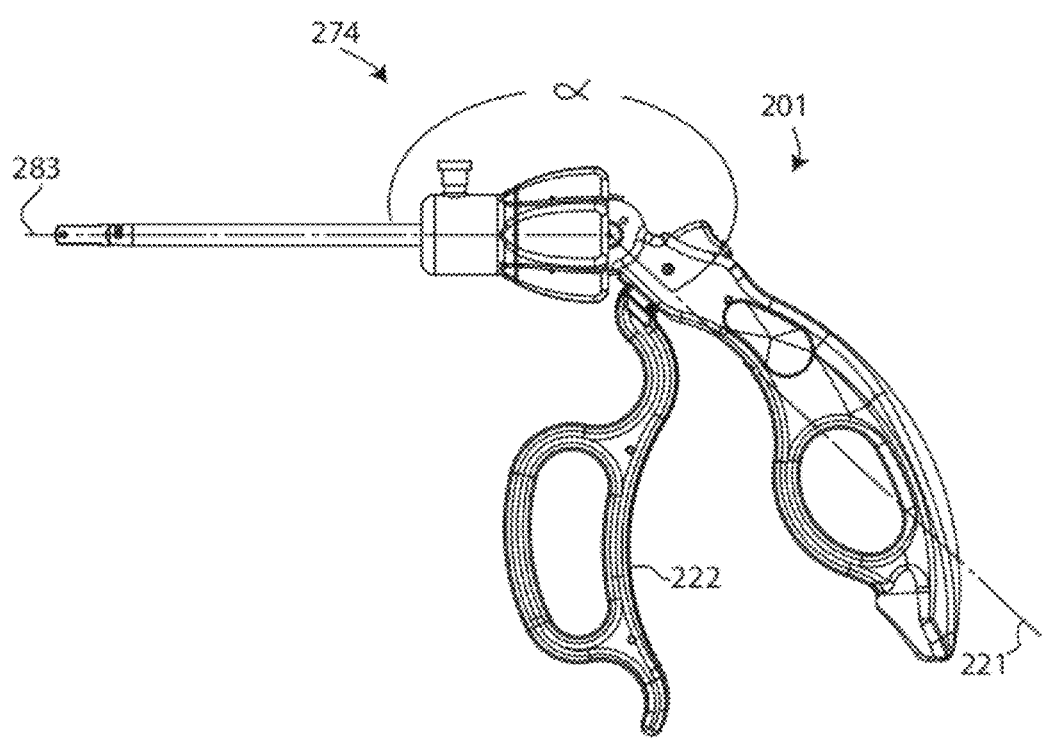
FIG. 17 is a side view of the surgical instrument of FIG. 16 with the handles of the surgical instrument in a "drop-down" position and the second handle in an "at rest" position.

FIG. 17 shows a side view of the surgical instrument 200 of FIG. 16 with the handle section 201 adjusted in a "drop-down" position relative to the longitudinal axis 283 of the working shaft section 274, similar to other embodiments disclosed herein. The surgical instrument of FIG. 16 also shows the second handle 22 in the "at rest" or biased position.

Figure 18:
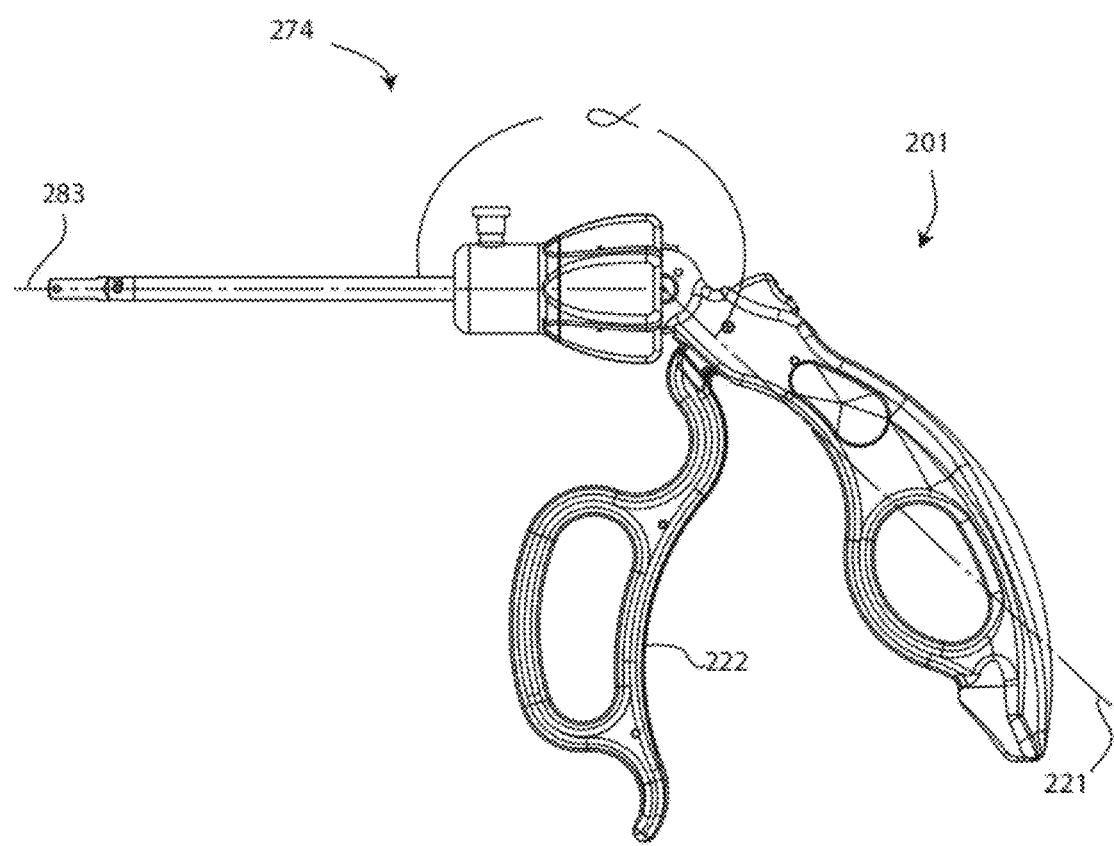
FIG. 18 is a side view of the surgical instrument of FIG. 16 with the handles of the surgical instrument in the "in-line" position and the second handle moved forward.

FIG. 18 shows a side view of the surgical instrument 200 of FIG. 16 with the handle section 201 adjusted in a "drop-down" position relative to the longitudinal axis 283 of the working shaft section 274 and with the second handle 22 in the "forward" or unlocked position.

Figure 19:
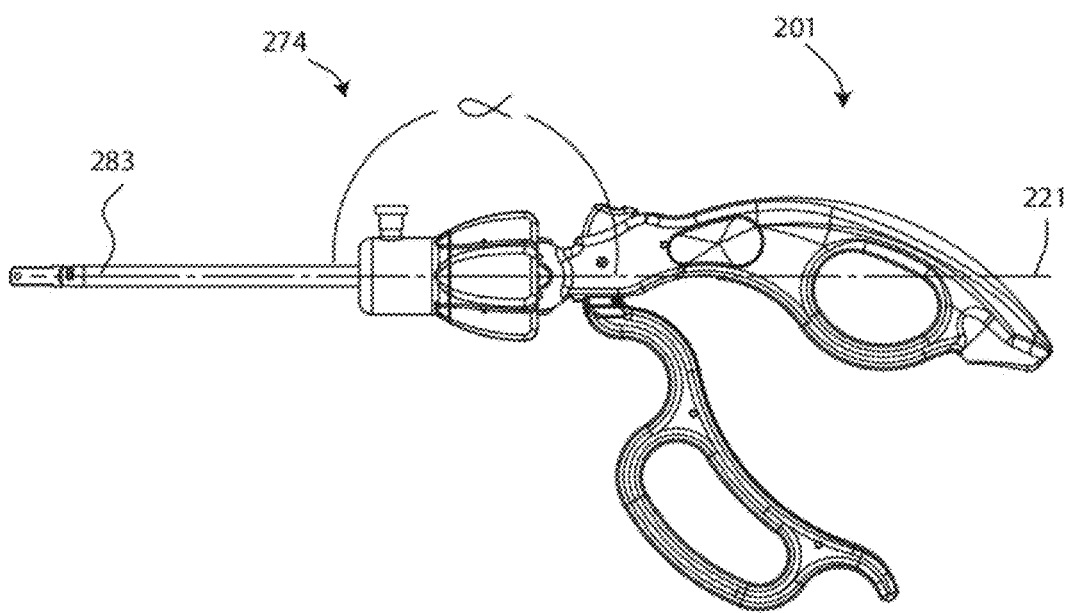
FIG. 19 is a side view of the surgical instrument of FIG. 16 with the handle section of the surgical instrument in the "in-line" position.

FIG. 19 shows a side view of the surgical instrument 200 of FIG. 16 with the handle section 201 adjusted in an "in-line" position relative to the longitudinal axis 283 of the working shaft section 274.

Figure 20:
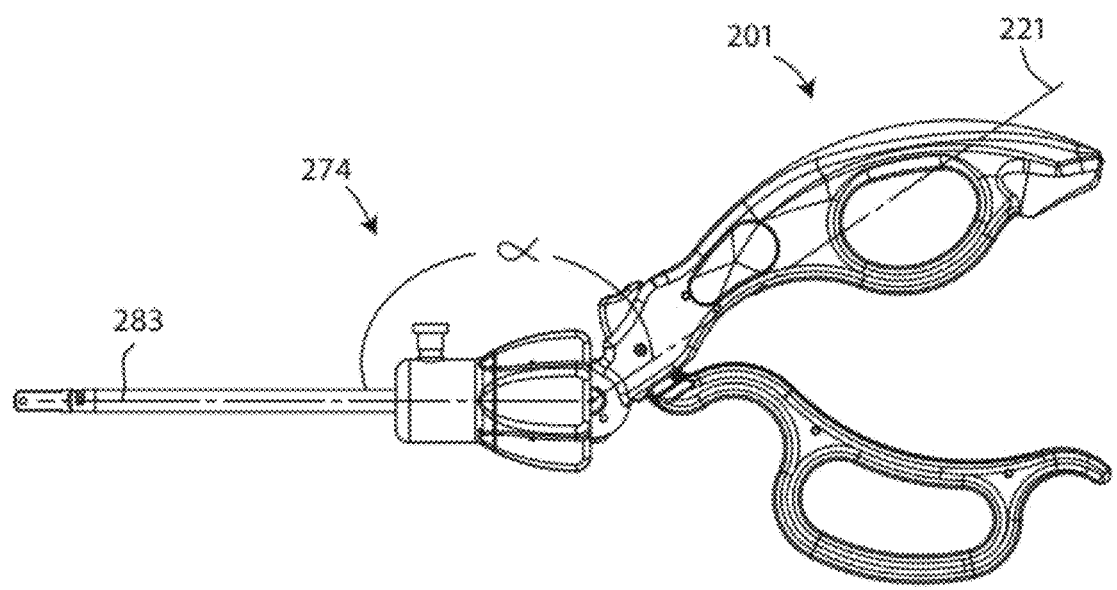
FIG. 20 is a side view of the surgical instrument of FIG. 16 with the handle section of the surgical instrument in the "up-angled" position.

FIG. 20 shows a side view of the surgical instrument 200 of FIG. 16 with the handle section 201 adjusted in an "angled-up" position relative to the working shaft section 274.

Figure 21:
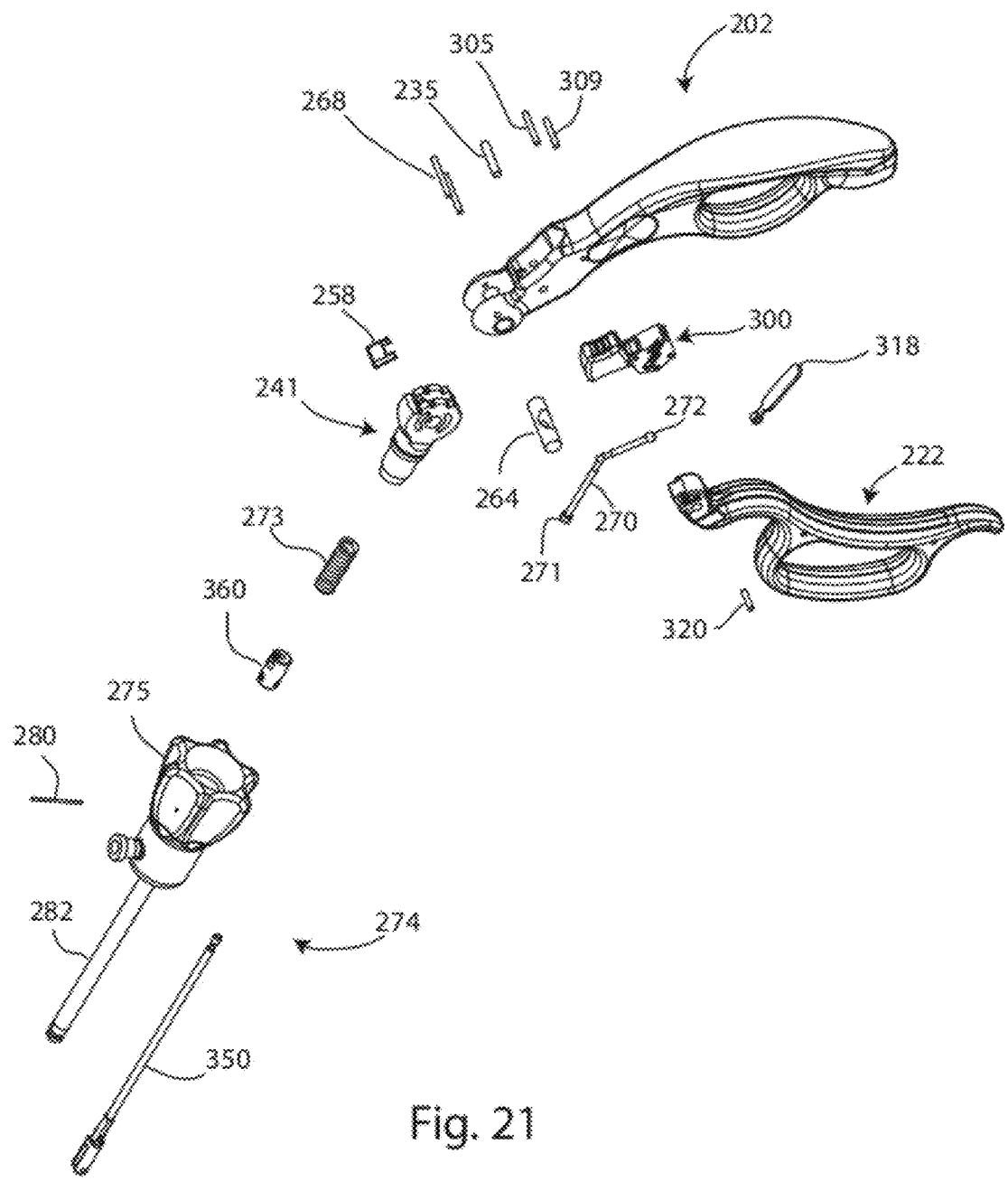
FIG. 21 is an exploded view of the surgical instrument of FIG. 16.

FIG. 21 shows an exploded view of the surgical instrument 200 with its various components. FIGS. 22A-37B illustrate the individual components of FIG. 21 in greater detail. A detailed description of the structure and features for each individual component will be given in a generally proximal to distal direction with reference to FIGS. 22A-37B. A detailed description of how each of the individual components interrelate with one another will then be given, along with the functional relationships between each component. Methods of using the surgical instrument 200 will also be given to illustrate how a surgeon can utilize the surgical instrument 200 to achieve greater ergonomic postures during surgery.

Figure 22A:
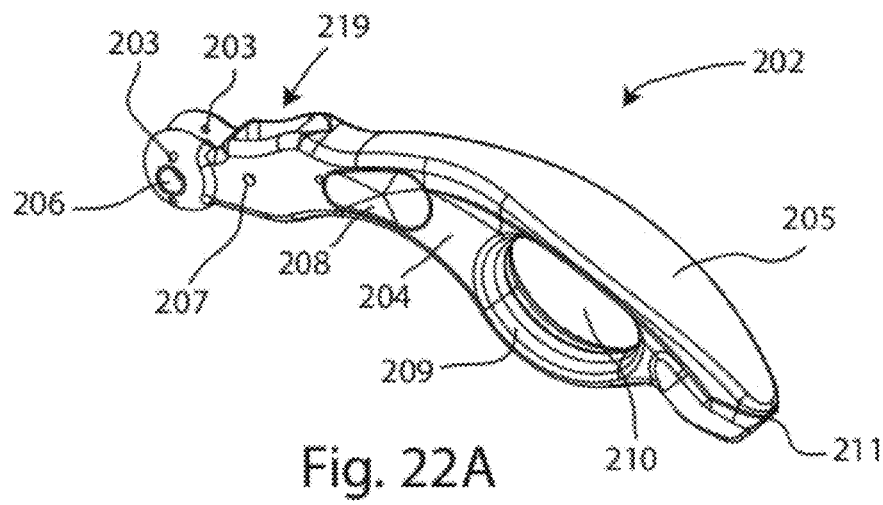
FIG. 22A is an isometric view of a first handle in accordance with another embodiment of the present disclosure.
Figure 22B:
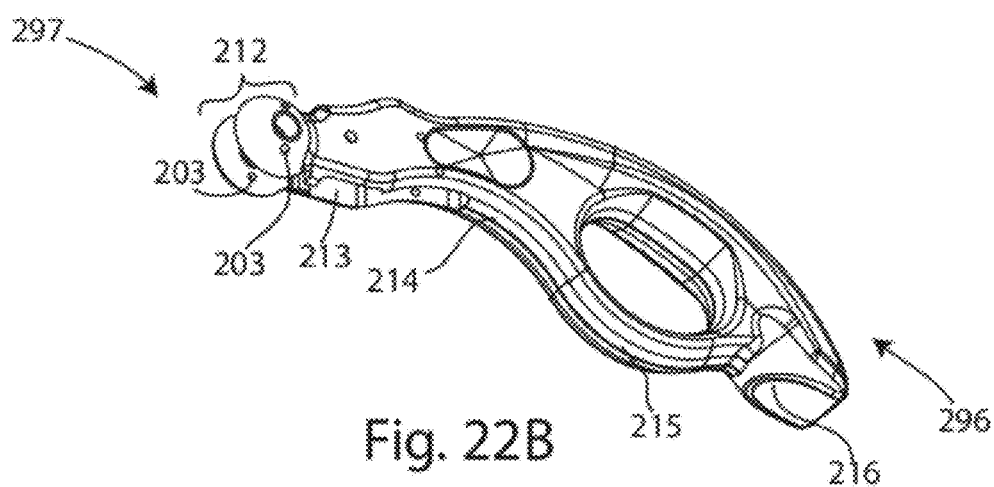
FIG. 22B is another isometric view of the first handle of FIG. 22A.
Figure 22C:
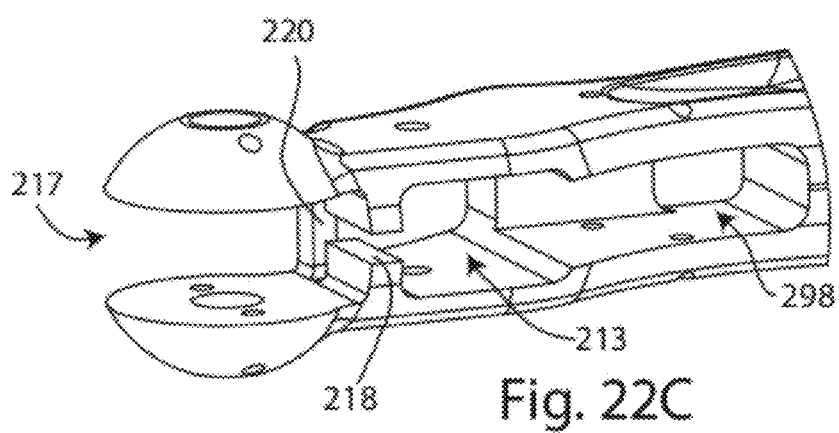
FIG. 22C shows an enlarged isometric view of the distal end of the first handle of FIGS. 22A and 22B.

FIGS. 22A-22C show various isometric views of a first handle 202, according to one embodiment of the present disclosure. The first handle 202 has a proximal end 296 and a distal end 297. The first handle 202 can have a top surface 205, a bottom surface 215, and two side surfaces 204. The top surface 205 can have a spatulate leaf shape and/or curve downward in the distal to proximal direction to better conform to the surgeon's palm. In some embodiments, the top surface 105 can have a radius of curvature, or substantially lie along a radius of curvature. In some embodiments, the radius of curvature can be between about 2 and 4 inches. In other embodiments, the radius of curvature can be between about 2.5 inches and 3.5 inches. In a particular embodiment, the radius of curvature is about 2.9 inches.

The top surface 205 of the first handle 202 may have a convex or rounded shape in the lateral direction between the two side surfaces 204 of the first handle 202. The top surface 205 is preferably shaped to be substantially wide enough between the two side surfaces 204 to provide adequate comfort to the surgeon's palm by providing sufficient surface contact area between the top surface 205 and the surgeon's palm to reduce or eliminate "hot spots" from forming on the surgeon's palm. The top surface 205 can have a maximum width and a minimum width in the lateral direction between the two side surfaces. In some embodiments, the minimum width of the top surface is located closer to the distal end of the first handle and the maximum width of the top surface is located closer to the proximal end of the first handle. In other embodiments the minimum width is between about 0.25 inches and about 0.75 inches. In a particular embodiment, the minimum width is about 0.5 inches. In some embodiments, the maximum width is between about 0.5 inches and about 1.25 inches. In one embodiment, the maximum width is about 0.88 inches. The location of the minimum width of the top surface can be chosen to correspond to the area of the top surface 205 that the surgeon's thumb traverses when the surgeon switches between a "finger loop" grip style and a "palm" grip style. Having the minimum width of the top surface in this area of the top surface 205 can allow the surgeon to more easily switch between the "finger loop" grip style and the "palm" grip style because the smaller width makes it easier for the surgeon's thumb to traverse this area of the handle.

The top surface 205 may include a button slot 219 configured to receive a portion of a ratcheting mechanism, such as a button. Moreover, the side surfaces 204 may include a thumb or finger rest area 208 formed on or into the side surfaces 204 to provide extra support for the surgeon's thumb when engaged along the side surface 204. The first handle 202 may have one or more finger loop holes 210 to receive one or more fingers during procedures requiring greater precision. The finger loop hole contact surface 209 may be convex in shape and wide enough to avoid or eliminate any "hot spots" from occurring on the surgeon's fingers during extended hours of operation. The first handle 202 can have a projection portion 211 at the proximal end 296 of the first handle 202. The projection portion 211 may provide greater surface area to interact with the surgeon's palm against the top surface 205. In one embodiment, the projection portion 211 can include an electrical connector to receive external input. The first handle 202 can also have a bottom surface 215 and a bottom surface recess area 214 having a concave shape configured to interact with one or more of the surgeon's fingers as needed.

Any or all of the surfaces of the first handle 202 may include a comfort material (not shown) attached to one or more of the surfaces of the first handle 202, such as a soft rubber, polymer, or silicone. The comfort material may be applied to the first handle 202 after manufacture, or the comfort material may be integrally formed or molded to the first handle 202 during manufacture by any suitable manufacturing processes including, but not limited to, bonding or overmolding.

The distal end 297 of the first handle 202 may include a head portion 212 for receiving a suitably shaped pivot housing 241 into the pivot housing slot 217. The head portion 212 may have stop pin holes 203 formed through both sides of the head portion 212 for receiving stop pins 268, as will be discussed in further detail below. The head portion 212 can have a pivot pin hole 206 formed through the head portion 212 configured to receive a pivot pin 264. The first handle 202 may include a pin hole 207 formed through, or substantially through, the side surfaces 204 of the first handle 202 and configured to receive a pivot pin 235 to pivotably secure a second handle 222. In this embodiment, the surgical instrument 200 includes a dual pivot design with a first pivot connecting the handle section 201 to the working shaft section 274, and a second pivot connecting the second handle 222 to the first handle 202. Moreover, the first and second pivots are not coaxial with each other in this embodiment.

Referring to FIGS. 22B-22C, the first handle 202 may include a receiver slot 213 configured and shaped to receive the head portion 227 of a suitable second handle 222, as will be discussed in further detail below. FIG. 6C illustrates a pivot housing slot 217 configured to receive a suitable pivot housing 241, in greater detail. FIG. 6C also illustrates an actuator aperture 218 formed within the first handle 202 proximal to the head portion 212 and shaped to allow an actuator 270 to be disposed therethrough. The first handle 202 may also have a ratchet slot 298 formed therein and configured to receive a suitable ratcheting mechanism, as will be discussed in greater detail below.

Referring now to FIGS. 23A-23D, a second handle 222 in accordance with one embodiment of the present disclosure is shown. The second handle 222 can have a proximal end 237 and a distal end 238. The second handle 222 can also have a top surface 226, a bottom surface 234, and two side surfaces 236. Each of the aforementioned surfaces may have a generally rounded or convex shape to increase comfort. The top surface 226 of the second handle 222 may have a slight "S-shaped" curvature formed therein moving in the distal to proximal direction. The distal end 238 of the second handle 222 may include a head portion 227 configured to interact with the receiver slot 213 of the first handle 202, as shown in FIGS. 22A-22C. The second handle 222 can have retainer members 286, a ramp pivot hole 284 and a ramp pivot slot, which will be discussed in greater detail below.

The second handle 222 may have one or more finger loop holes 230 configured to receive one or more of the surgeon's fingers during procedures that require greater precision. The inner contact surface 229 of the finger loop hole 230 may have a rounded or convex shape to comfortably engage the fingers of the surgeon.

The second handle 222 may have at least one finger contact surface. Moreover, the at least one finger contact surface can be configured to substantially lie along a radius of curvature. The radius of curvature can be between about 1.5 and 3.5 inches in some embodiments. In other embodiments, the radius of curvature may be between about 2 inches and 3 inches. In a particular embodiment, the radius of curvature is about 2.5 inches.

In one embodiment, the second handle 222 can have a finger loop 230 defining a first finger contact surface 239 configured to receive the surgeon's ring finger and middle finger, a projection 232 configured to receive the surgeon's pinky finger, and a recess portion 288 forming a third finger contact surface 228 configured to receive the surgeon's index finger. Moreover, one or more of these finger contact surfaces can substantially lie along a radius of curvature. For example, the first and second finger contact surfaces can substantially lie along a radius of curvature of about 2.5 inches and the third finger contact surface can be offset from the radius of the curvature of the first and second finger contact surfaces by about 0.0625 inches.

Any or all of the surfaces of the second handle 222 may include a comfort/grip-enhancing material (not shown) attached to one or more of the surfaces of the second handle 222, such as a soft rubber, polymer, or silicone material. The comfort/grip-enhancing material may be applied to the second handle 222 after manufacture, or alternatively the comfort/grip-enhancing material may be integrally formed or molded to the second handle 222 during manufacture by several manufacturing processes, such as, bonding or overmolding.

Figure 23A:
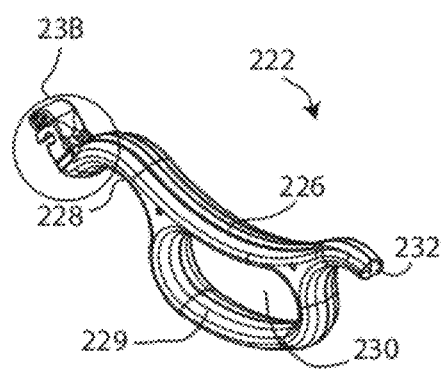
FIG. 23A is an isometric view of a second handle in accordance with another embodiment of the present disclosure.
Figure 23B:
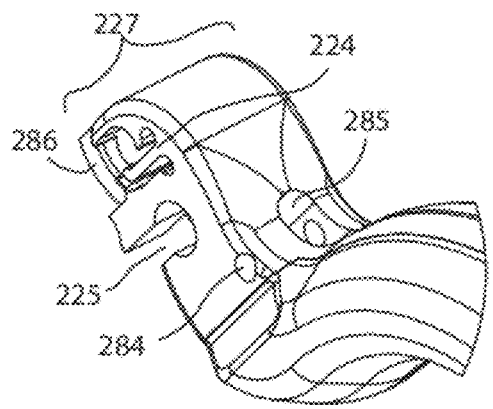
FIG. 23B shows an enlarged view of the encircled area in FIG. 23A.
Figure 23C:
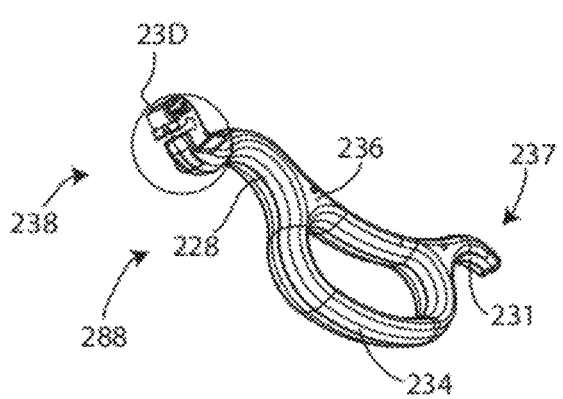
FIG. 23C is another isometric view of the second handle of FIG. 23A.
Figure 23D:
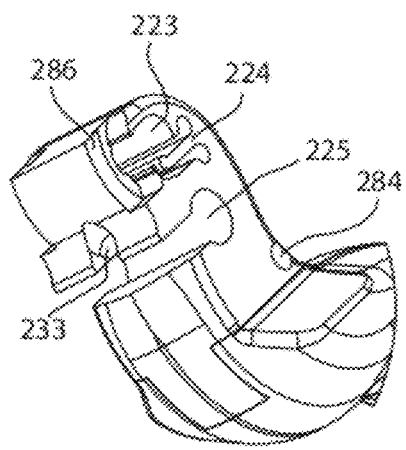
FIG. 23D shows an enlarged view of the encircled area in FIG. 23C.

Continuing with FIGS. 23A-23B, the head portion 227 of the second handle 222 can have a latch release cavity 223 formed through the head portion 227. The latch release cavity 223 may have an oblong or elongated oval shape configured to receive a pivot pin 235 to allow the pivot pin 235 to move translationally within the latch release cavity 223. The latch release cavity 223 can have a spring detent 224 just below the latch release cavity 223 to help control and bias the translational movement of the pivot pin 235, as will be discussed in greater detail below. The head portion 227 can have an actuator bore 233 formed through the head portion 227 and in communication with an actuator connection recess 225.

Figure 24:
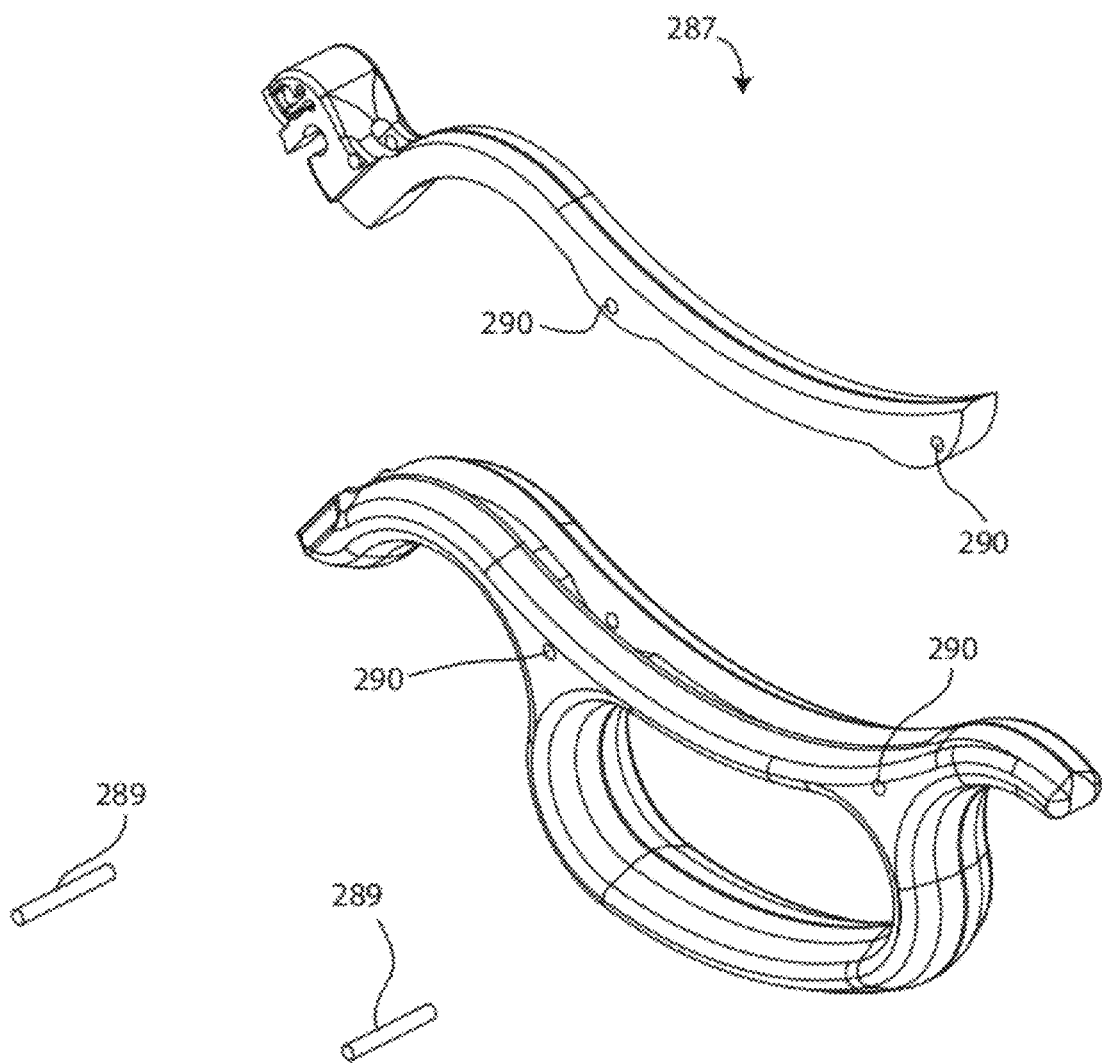
FIG. 24 is an exploded isometric view of a multi-component second handle in accordance with another embodiment of the present disclosure.

FIG. 24 shows one embodiment of a multi-component second handle 222 having a removable top portion 287 which may be attached to the second handle 222 with pins 289 threaded through pin holes 290. In other embodiments, the second handle 222 may comprise an alternative control member such as a trigger, a button, a lever, a truncated handle or any other structure suitable for a surgical instrument. In some embodiments, the second handle 222 may be omitted entirely.

Figure 25A:
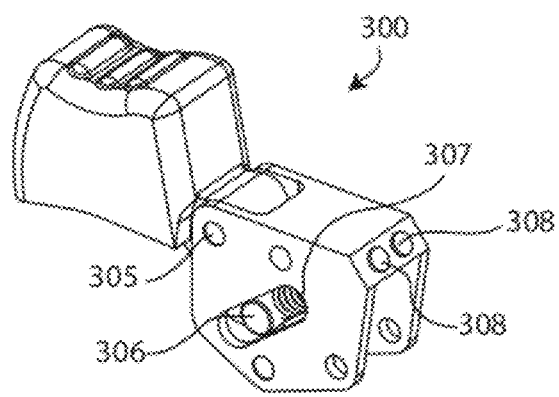
FIG. 25A is an isometric view of a ratcheting mechanism in accordance with one embodiment of the present disclosure.

FIGS. 25A-26C show one embodiment of a ratcheting mechanism 300 in accordance with one embodiment of the present disclosure. FIG. 25A shows an isometric view of an assembled ratcheting mechanism 300. FIG. 25B shows an exploded view of the ratcheting mechanism 300 of FIG. 25A. The ratcheting mechanism 300 may include a release member 301 pivotably connected to a ratchet body 310. The release member 301 may include a button 302 and a wedge release member 303 with the release member 301 configured to be pivotably connected to the ratchet body 310 using a suitable pivot pin 305 threaded through the pin holes 311 of the ratchet body 310 and through the pin hole 304 of the release member 301. The ratchet mechanism 300 can include a wedge member 306 biased toward one end of the ratcheting mechanism 300. The wedge member 306 can be disposed within the ratchet body 310 through the wedge member slots 312. Biasing members 307 can be disposed within the ratchet body 310 and held in place by guide members 308 threaded through the guide member slots 314. The biasing members 307 can be one or more springs which can impart a substantially constant bias force on the wedge member 306. The ratcheting mechanism 300 can also include a second ramp support pin 309.

Figure 26A:
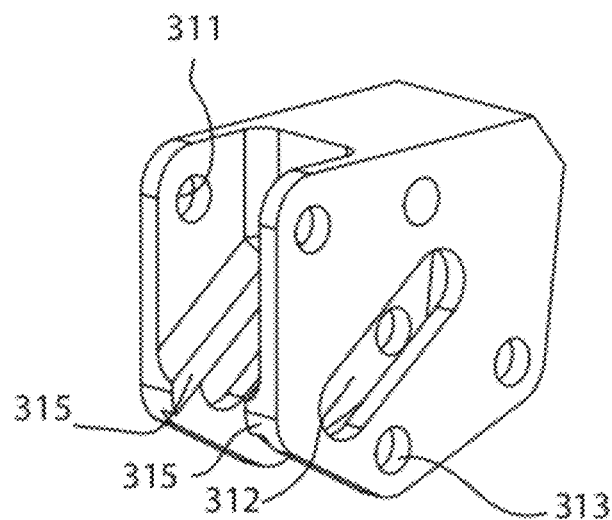
FIG. 26A is an isometric view of the ratchet body shown in FIGS. 25A and 25B.
Figure 26B:
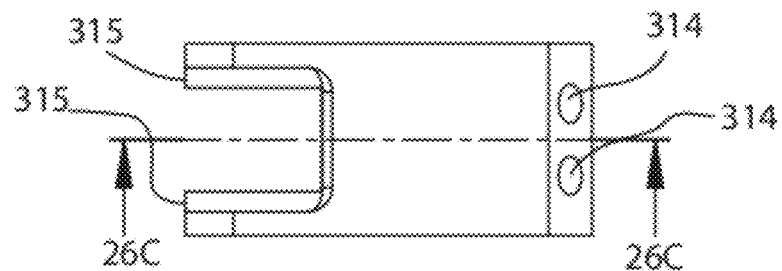
FIG. 26B is a top view of the ratchet body of FIG. 26A.
Figure 26C:
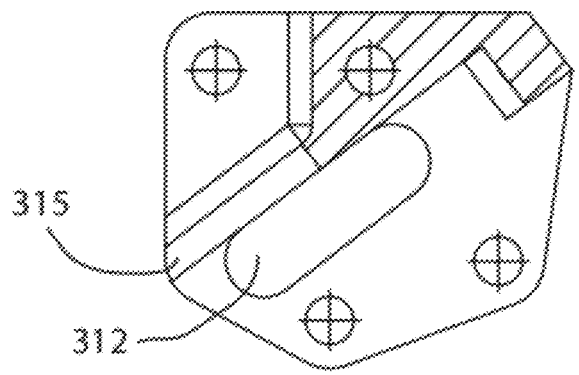
FIG. 26C is a side view of the ratchet body of FIG. 26A.
Figure 28:
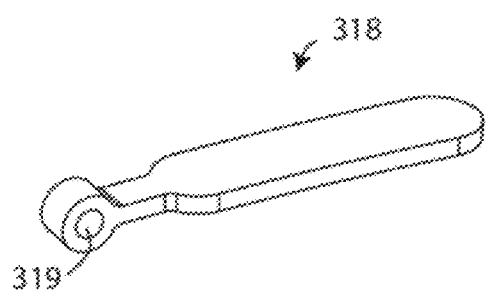
FIG. 28 is an isometric view of a ramp according to one embodiment of ratcheting mechanism.

FIGS. 26A-26C show the ratchet body 310 in greater detail. The ratchet body 310 can have one or more first ramps 315 configured to interact with the wedge member 306 from above. FIG. 28 shows a second ramp 318 which may also interact with the wedge member 306 from below. The second ramp 318 can be pivotably mounted to the second handle 222 using the pivot pin hole 319 formed in the end of the second ramp 318 and a pivot pin 320 threaded through the pivot pin hole 319 of the second ramp 318 and through the pivot holes 284 formed in the second handle 222, as shown in FIG. 23B. The second ramp 318 may project outward from the ramp pivot slot 285 formed in the second handle 222.

Figure 25B:
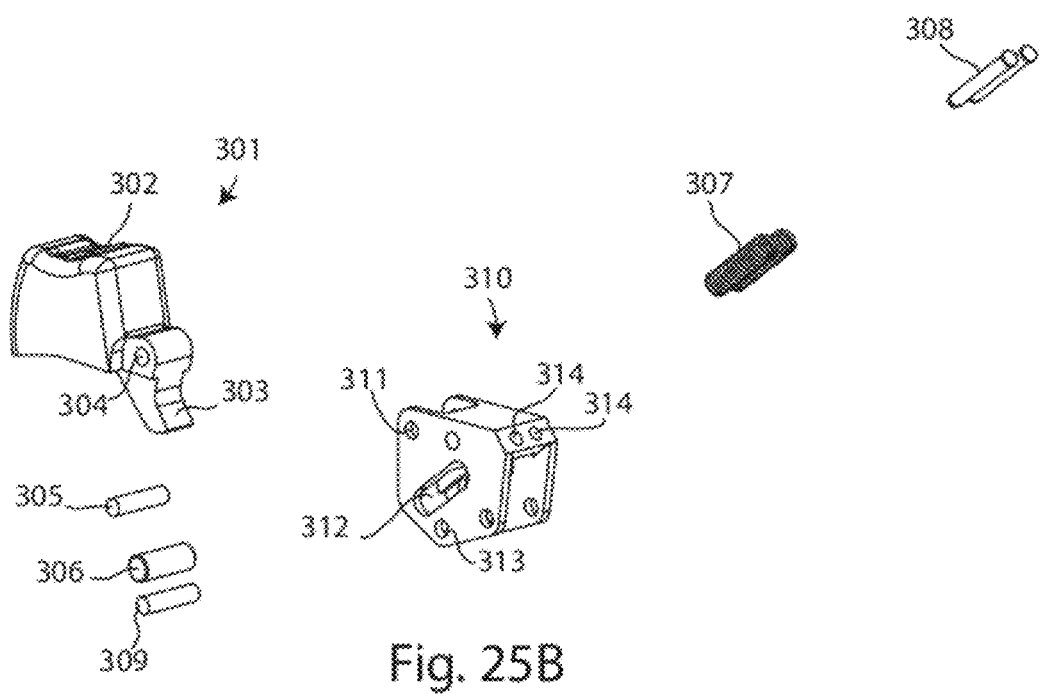
FIG. 25B is an exploded view of the ratcheting mechanism of FIG. 25A.
Figure 41:
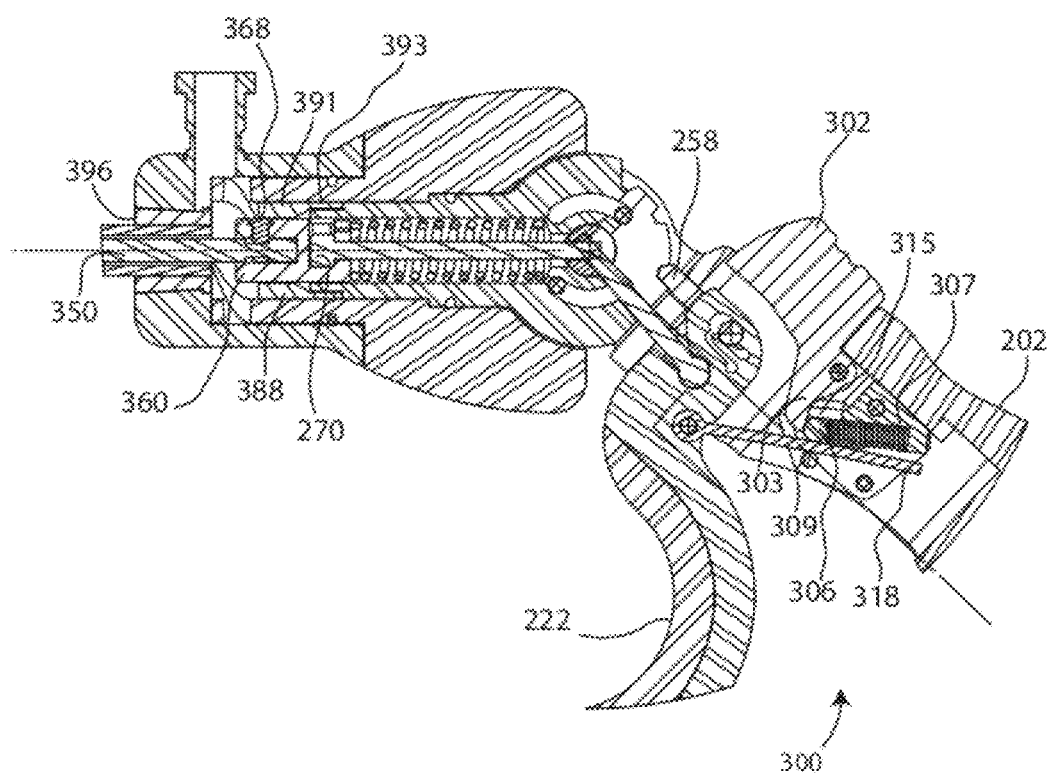
FIG. 41 is an enlarged view of the encircled area shown in FIG. 40B.
Figure 42A:
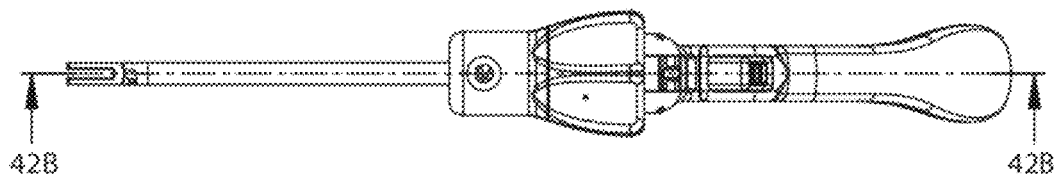
FIG. 42A is a top view of the surgical instrument of FIG. 18 with the handle section in the "drop-down" position and with the second handle in a "forward" position having a section line 42B-42B.
Figure 42B:
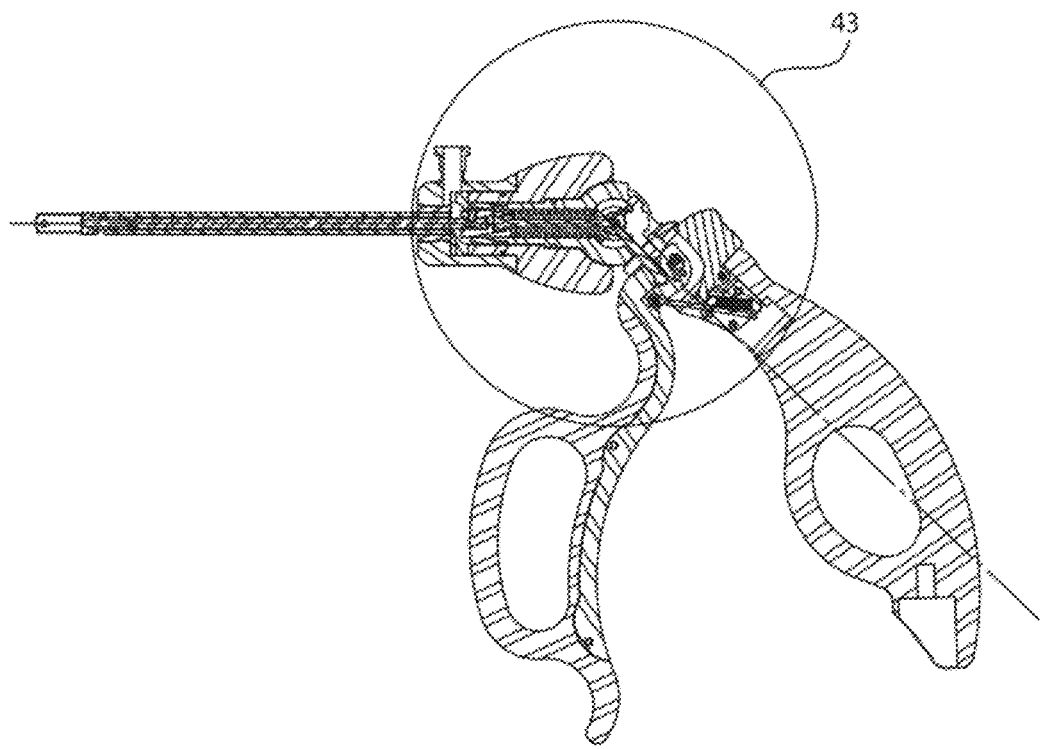
FIG. 42B is a cross-sectional side view of the surgical instrument of FIG. 42A, taken along the section line 42B-42B in FIG. 42A.
Figure 43:
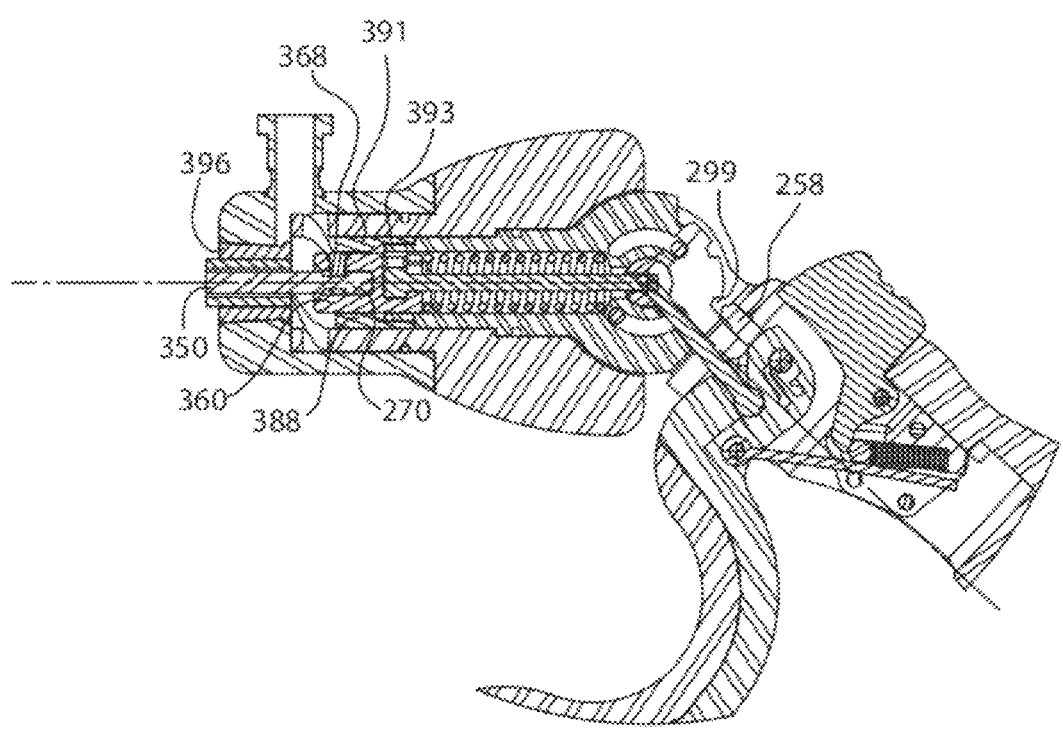
FIG. 43 is an enlarged view of the encircled area shown in FIG. 42B.

FIG. 41 shows a cross-sectional side view of the surgical instrument 200 with the ratcheting mechanism 300 installed in the surgical instrument 200. The ratcheting mechanism 300 can be attached to the first handle 202 with a pivot pin 305 and the second ramp support pin 309, as can be seen in FIG. 21 and FIG. 25B. FIG. 41 shows how the second ramp 318 can be pivotably attached to the second handle 222. The second ramp can project into the ratcheting mechanism 300 and between the second ramp support pin 309 and the wedge member 306. The second ramp 318 and the first ramp 315 can be angled with respect to each other such that the surfaces of the second ramp 318 and the first ramp 315 converge closer to each other moving in the distal direction and diverge away from each other moving in the proximal direction. A wedge member 306 disposed between the first ramp 315 and the second ramp 318 can be sized and shaped to interact with the first and second ramps as they angle toward each other in the distal direction and away from each other in the proximal direction. For example, the width of the wedge member 306 can be less than the distance between the surfaces of the second ramp 318 and the first ramp 315 in the proximal direction and greater than the distance between the surfaces of the second ramp 318 in the first ramp 315 in the distal direction. Accordingly, two zones are formed between the first ramp 315 and a second ramp 318, a free zone in the proximal direction, and an interference zone in the distal direction. One or more biasing members 307 can also be used to impart a biasing force upon the wedge member 306, forcing the wedge member in the distal direction and into the interference zone. In one embodiment, the one or more biasing members 307 can be one or more springs configured to impart a substantially constant force upon the wedge member 306.

In operation, applying a pivot force to the second handle 222, to pivot the second handle 222 toward the first handle 202, will cause the second ramp 318 to move in the proximal direction which will also cause the wedge member 306 to move or rotate in the proximal direction. The wedge member 306 enters the free zone allowing the second ramp 318 to continue moving in the proximal direction, allowing the second handle 222 to pivot towards the first handle 202. However, if a pivot force is applied to the second handle 222 in the opposite direction, then the second ramp will move in the distal direction causing the wedge member 306 to rotate or move in the distal direction, forcing the wedge member 306 into the interference zone where the width of the wedge member 306 is greater than the distance between the two ramps. The second ramp 318 will become "pinched" between the wedge member and the second ramp support pin 309, preventing the second handle 222 from pivoting away from the first handle 202. In this manner, the ratcheting mechanism 300 allows the first handle 202 and the second handle 222 to pivot towards each other, while preventing the first handle 202 and the second handle 222 from pivoting away from each other. In this manner, the ratcheting mechanism 300 allows for an infinite number of positional relationships to be selected and maintained between the first handle 202 and the second handle 222.

The ratcheting mechanism 300 can be disabled, or released, with a suitable release member 301 that can force the wedge member 306 toward the free zone. The button 302 of the release member 301 can be depressed causing the wedge release member 303 to move in the proximal direction forcing the wedge member 306 into the free zone. As the wedge member 306 enters the free zone, the second ramp 318 is no longer "pinched" between the wedge member 306 and the second ramp support pin 309. The second ramp is now free to move in the distal direction, along with the second handle 222 which is attached to the second ramp 318.

Figure 27:
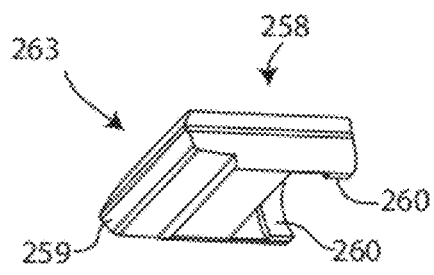
FIG. 27 is an isometric view of a locking member in accordance with one embodiment of the present disclosure.

FIG. 27 shows a locking member 258 in accordance with one embodiment of the present disclosure. The locking member 258 may have a locking surface 263 including one or more locking teeth 259 formed in a surface of the locking member 258 and configured to engage the locking surface 257 of a suitable pivot housing 241, which can also include one or more teeth 245, and or one or more locking member receiver slots 299. The locking member 258 can also have projections 260 configured to interact with retainer members 286 formed on the head portion 227 of the second handle 222 to keep the locking member 258 engaged with the second handle 222.

FIGS. 29A-29D show one embodiment of a connector 360 in accordance the present disclosure, and will be discussed in greater detail below.

Figure 30A:
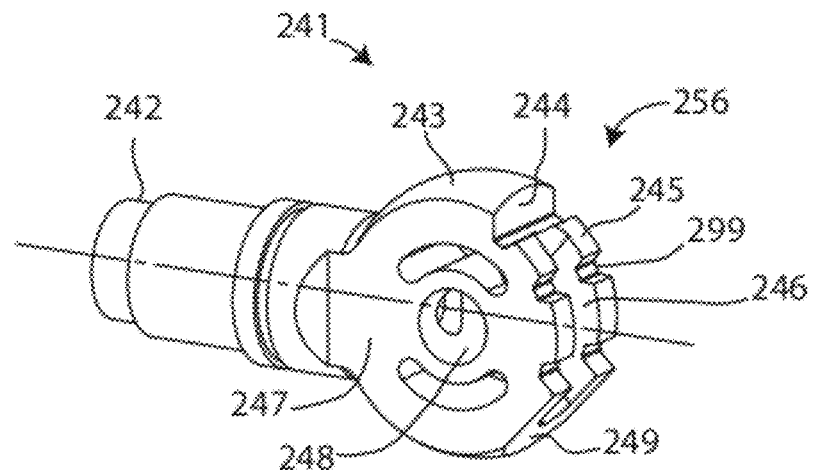
FIG. 30A is an isometric view of a pivot housing in accordance with one embodiment of the present disclosure.
Figure 30:
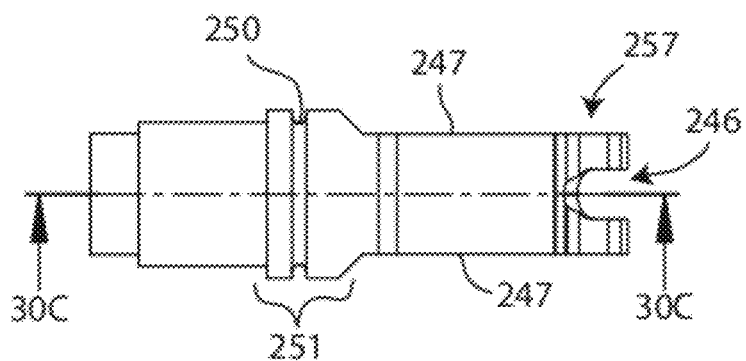
FIG. 30B is a top view of the pivot housing a FIG. 30A having a section line 30C.
FIG. 30C is a cross-sectional side view of the pivot housing of FIG. 30B, taken along the section line 30C-30C in FIG. 30B.
Figure 30C:
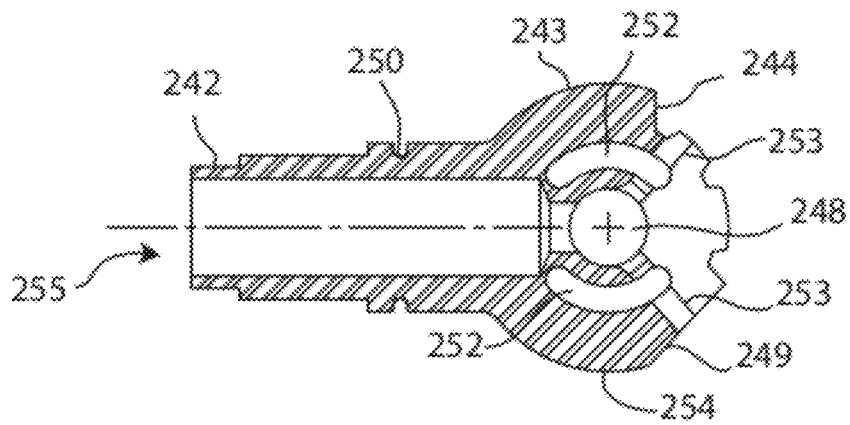

FIGS. 30A-30C show a pivot housing 241, in accordance with one embodiment of the present disclosure. The pivot housing 241 may include a hollow shaft 242 at its distal end and a pivot head portion 256 at its proximal end. The pivot head portion 256 may have a top surface 243, a bottom surface 254, side surfaces 247, a top angled surface 244, and a bottom angled surface 249. The top surface 243 and the bottom surface 254 may have partially spherical shapes configured to receive a suitable rotation knob 275 to allow the rotation knob 275 to rotate freely about the pivot head portion 256. The pivot head portion 256 may include a pivot pin hole 248 formed through the pivot head portion 256 between the sides 247. Additionally, the pivot head portion 256 may include stop pin slots 252 formed through the pivot head portion 256 having elongated and curved oval shapes. The pivot head portion 256 may also include one or more locking teeth 245, and/or one or more locking member receiver slots 299, formed in a surface of the pivot head portion 256.

With reference to FIG. 30B, the hollow shaft 242 may have a larger diameter portion 251 wherein the larger diameter portion 251 may include an annular groove 250 formed therein. The annular groove 250 may be shaped and configured to receive a retaining pin 280 to allow the rotation knob 275 to rotate freely about the pivot housing 241, while keeping the rotation knob 275 from moving translationally with respect to the working shaft 282. The hollow shaft 242 can have an inner bore 255 shaped to receive a suitable restoring spring 273. The inner bore 255 may be in communication with the pivot pin hole 248 and a proximal opening 246 in the pivot head portion 256. The proximal opening 246 may open wider moving in the distal to proximal direction with diverging top and bottom surfaces 253.

Figure 31A:
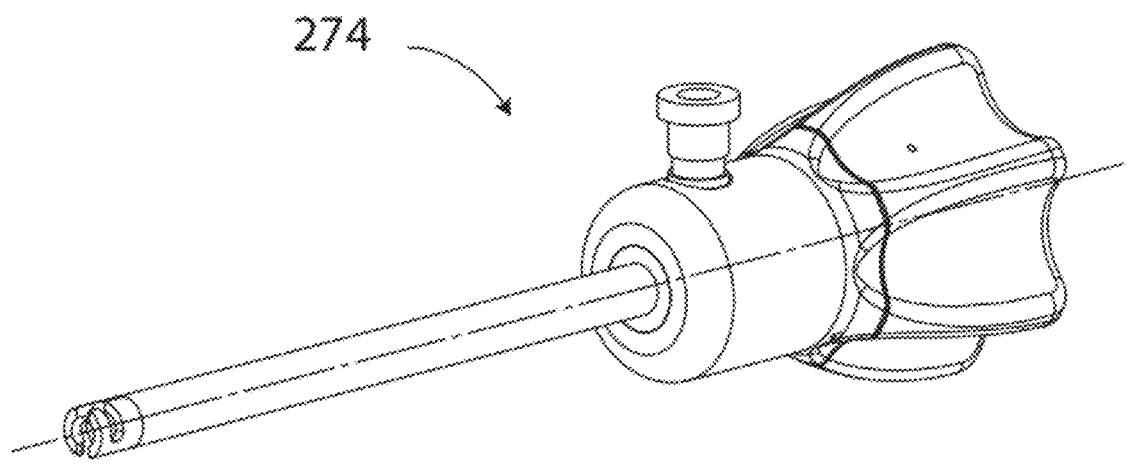
FIG. 31A is an isometric view of a working shaft section in accordance with one embodiment of the present disclosure.
Figure 31B:
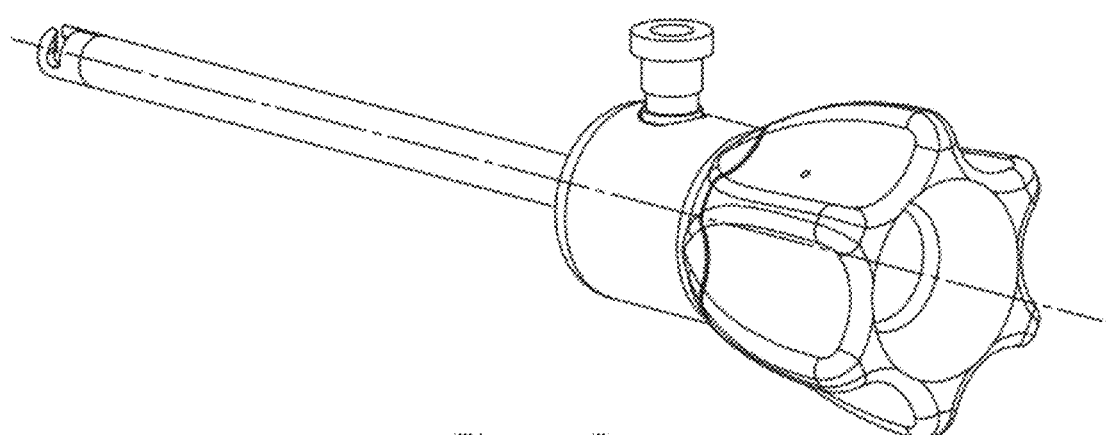
FIG. 31B is another isometric view of the working shaft section of FIG. 31A.
Figure 32:
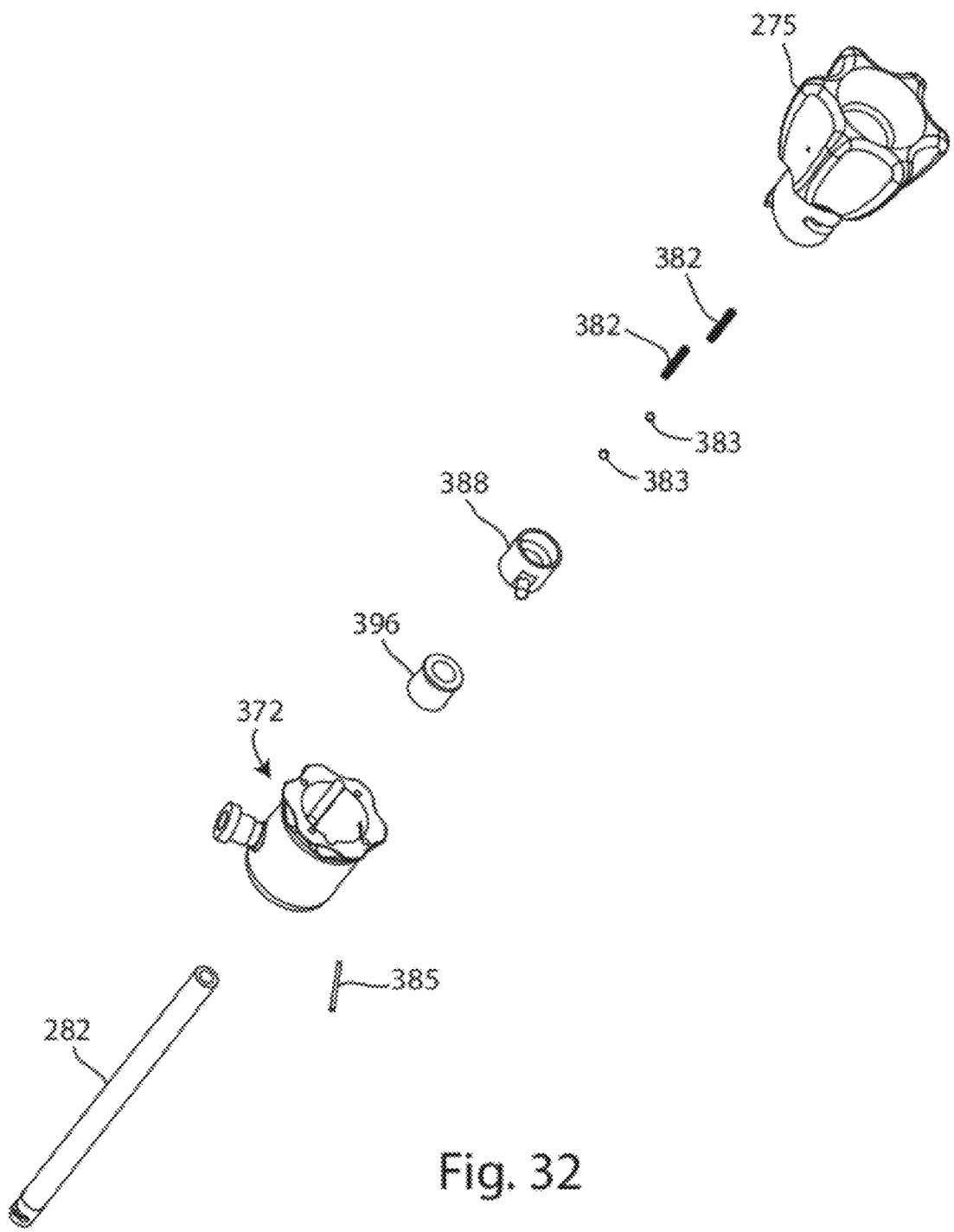
FIG. 32 is an exploded view of the working shaft section of FIGS. 31A and 31B.

FIG. 31A-31B show two isometric views of one embodiment of a working shaft section 274. FIG. 32 shows an exploded view of the working shaft section 274 of FIGS. 31A-31B.

FIG. 33 shows one embodiment of a rotation knob 275 in accordance with the present disclosure. The rotation knob 275 can have an outer surface that is larger in diameter at its proximal end 278 and smaller in diameter at its distal end 277. The distal end 277 of the rotation knob 275 can form a translation guide 397 with one or more channels 384 formed in the translation guide 397. The rotation knob 275 can have an annular groove 380 formed in a surface of the translation guide 397 and configured to interact with a suitable retaining pin 385. The rotation knob 275 can also have one or more longitudinal apertures formed therein and configured to receive springs 382 and spheres 383 therein.

The outer surface of the rotation knob 275 can be sized and shaped to engage with a surgeon's finger or thumb to facilitate rotation of the rotation knob 275. For example, the rotation knob 275 can have one or more ribs 281 and one or more depressions 276 formed in the outer surface of the rotation knob 275. The spacing of the ribs 281 and the size and depth of the depressions 276 are preferably sized to fit the width and shape of the average surgeon's fingers and/or thumb. However, it is to be understood that the size and shape of the depressions 276, as well as the number and spacing of the ribs 281, may be varied in any fashion or tailored in any way so as to fit any size finger or thumb. The rotation knob 275 is preferably located close enough to the handle section 201 to allow the surgeon to rotate the rotation knob 275 with one hand. For example, the surgeon may grasp the handle section 201 with one hand and use the thumb or index finger of the same hand to rotate the rotation knob 275.

FIG. 34 shows one embodiment of a control member 388 that can be used in the present disclosure. The control member can have a proximal end 389 and a distal end 390. The control member 388 can have a hollow body forming an inner surface with a smaller diameter portion 391 located toward the distal end 390 and a larger diameter portion (not shown) located toward the proximal end 389 of the control member 388. A chamfered surface 392 can be intermediate the smaller diameter portion 391 and the larger diameter portion. The control member 388 may have one or more translation members 394 engaged with a surface of the control member 388. FIG. 35 shows an isometric view of a working shaft collet 396 which can be used to frictionally engage a working shaft 282.

Figure 36A:
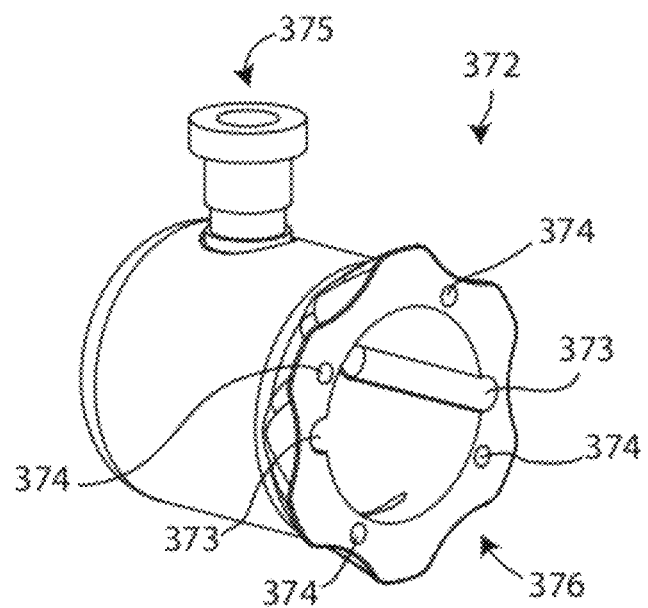
FIG. 36A is an isometric view of a second hollow body according to one embodiment of the present disclosure.
Figure 36B:
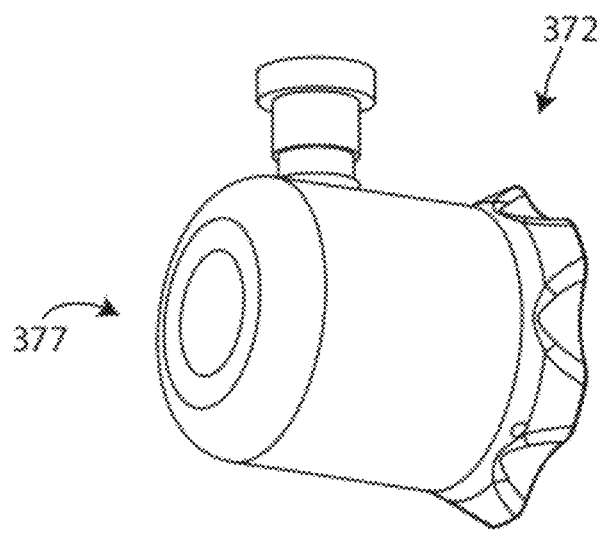
FIG. 36B is another isometric view of the second hollow body of FIG. 36A.

FIGS. 36A-36B show isometric views of a hollow body 372 according to one embodiment of the present disclosure.

The hollow body 372 can form an inner chamber and have one or more channels 373 formed in the surface of the inner chamber and configured to interact with the one or more translation members 394 of the control member 388. The proximal end 376 of the hollow body 372 can have a surface with one or more depressions 374 formed therein and configured to interact with spheres 383 inserted into the longitudinal apertures 381 of the rotation knob 275. The hollow body 372 may also have a port 375 connected to a surface of the hollow body 372. The port 375 can be in communication with the inner chamber of the hollow body 372. The port can be used as an aid in the cleaning process. For example, pressurized water can be forced into the port to help clean the inside of the hollow body 372.

Figure 37A:
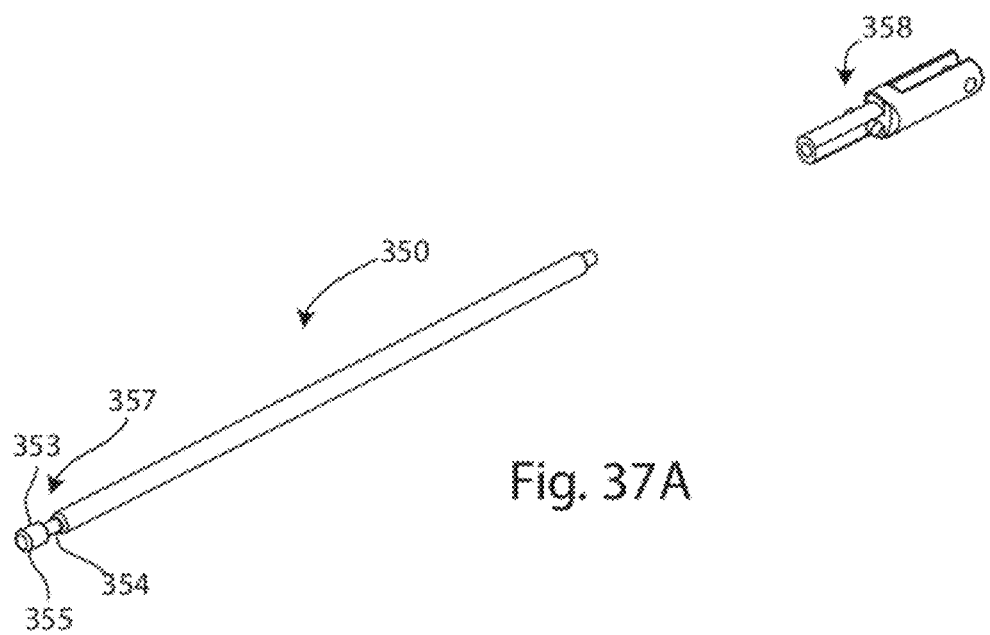
FIG. 37A is an isometric view of a working rod according to one embodiment of the present disclosure.
Figure 37B:
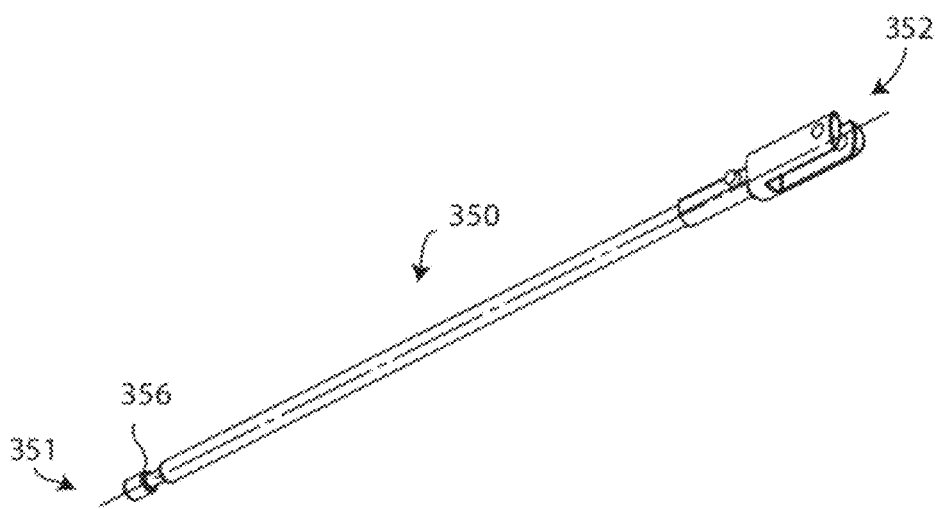
FIG. 37B is another isometric view of the working rod of FIG. 37A.
Figure 38A:
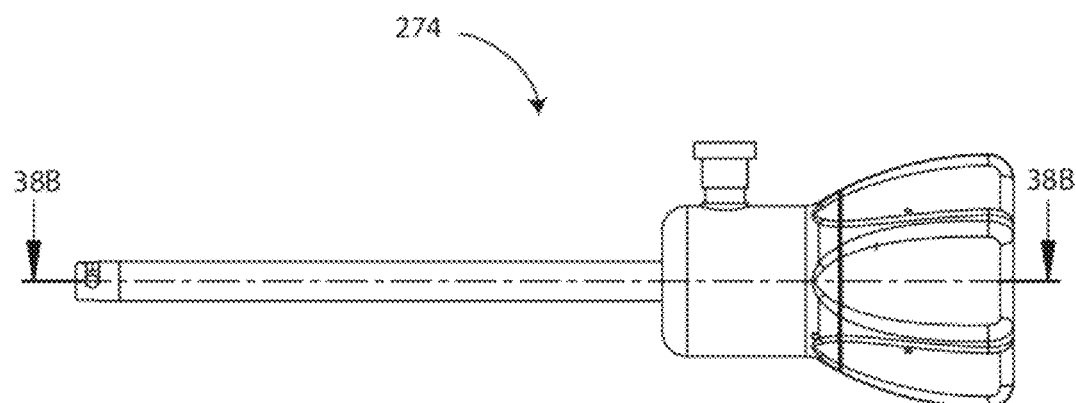
FIG. 38A is a side view of the working shaft section of FIG. 31A having a section line 38B-38B.
Figure 38B:
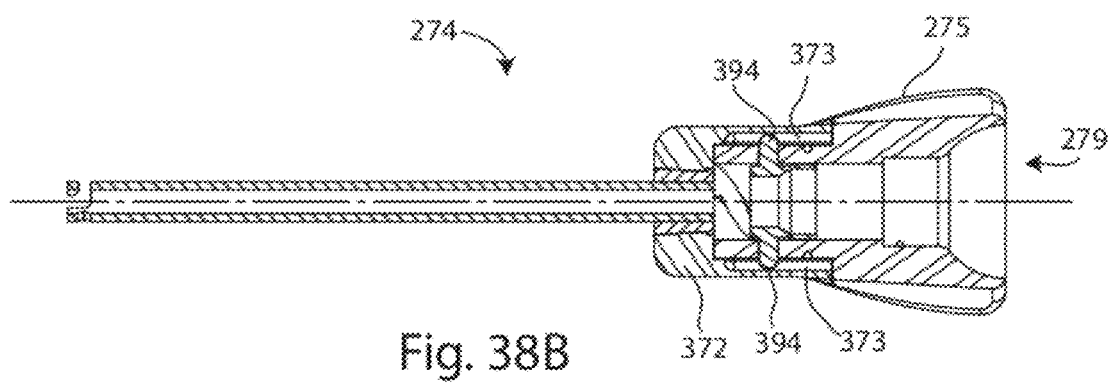
FIG. 38B is a cross-sectional side view of the working shaft section in FIG. 38A, taken along the section line 38B-38B in FIG. 38A.
Figure 39A:
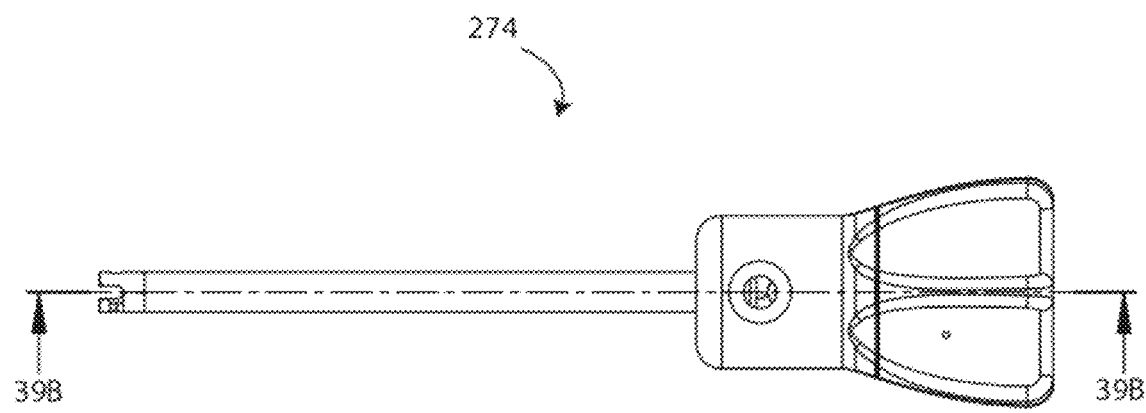
FIG. 39A is a side view of the working shaft section of FIG. 31A having a section line 39B-39B.
Figure 39B:
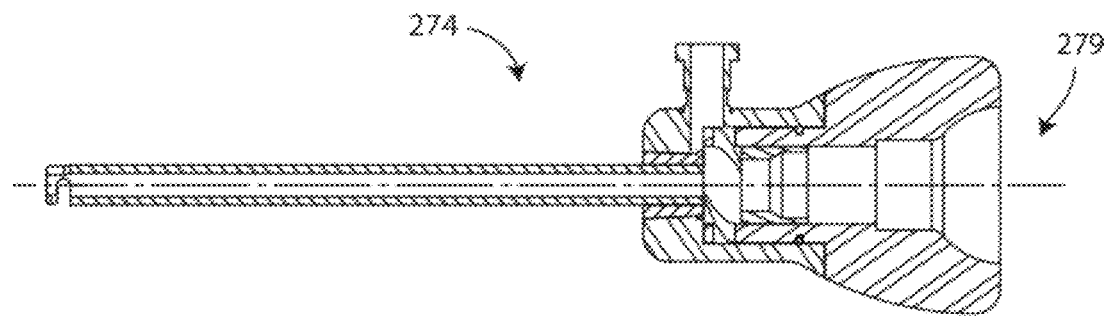
FIG. 39B is a cross-sectional side view of the working shaft section and FIG. 39A, taken along the section line 39B-39B in FIG. 39A.
Figure 40A:
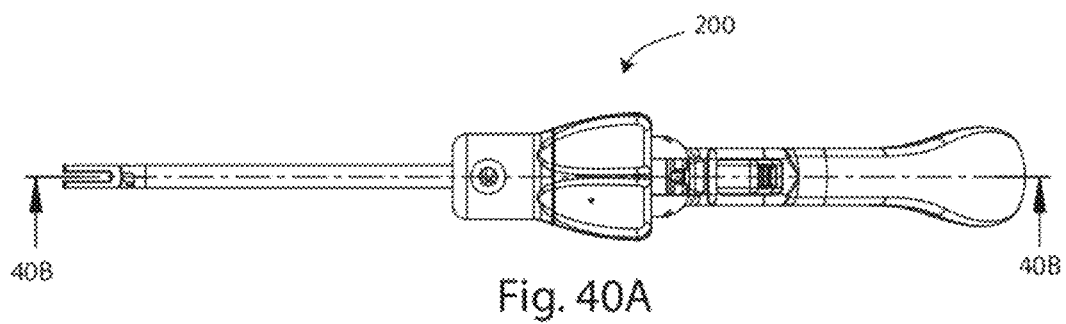
FIG. 40A is a top view of the surgical instrument of FIG. 17 with the handle section in the "drop-down" position and with the second handle in the "at rest" position having a section line 40B-40B.
Figure 40B:
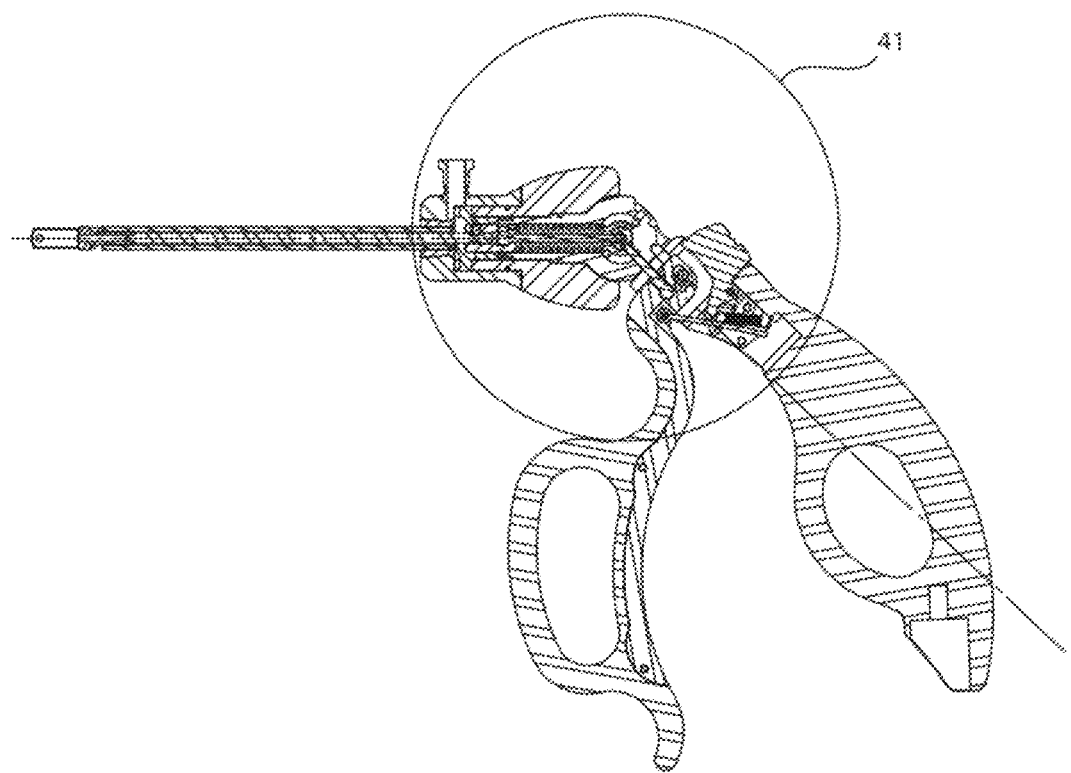
FIG. 40B is a cross-sectional side view of the surgical instrument in FIG. 40A, taken along the section line 40B-40B in FIG. 40A.

FIGS. 37A and 37B show isometric views of a working rod 350 that may be used with embodiments disclosed herein. The working rod 350 has a proximal end 351 and a distal end 352. The distal end 352 of the working rod 350 can be configured to attach a suitable end piece 358 for a given end effector (not shown). The proximal end 351 of the working rod 350 can have a connector portion 357 configured to interact with a suitable connector 360 as shown in FIGS. 29A-29D. The connector portion 357 can have a larger diameter portion 353, a smaller diameter portion 354, a first chamfered surface 355, and a second chamfered surface 356. The second chamfered surface 356 can be intermediate the smaller diameter portion 354 and the larger diameter portion 353. The first chamfered surface 355 can be proximal the larger diameter portion 353. In some embodiments, the first chamfered surface 355 can be replaced with a partially spherical shaped end piece proximal the larger diameter portion 353.

Figure 29A:
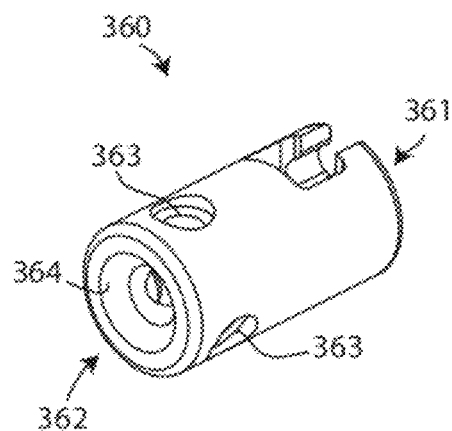
FIG. 29A is an isometric view of a connector according to one embodiment of the present disclosure.
Figure 29B:
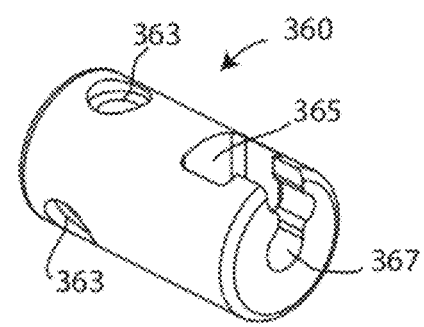
FIG. 29B is another isometric view of the connector of FIG. 29A.
Figure 29C:
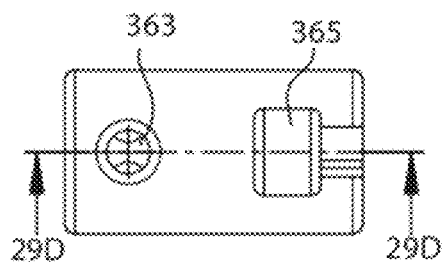
FIG. 29C is a top view of the connector of FIG. 29A having a section line 29D-29D.
Figure 29D:
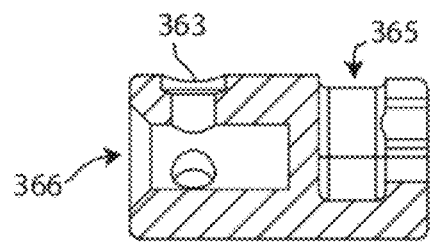
FIG. 29D is a cross-sectional side view of the connector of FIG. 29C, taken along the section line 29D-29D in FIG. 29C.

A system for coupling a working rod 350 to the surgical instrument 200 will now be explained with reference to FIGS. 29A-29D and FIGS. 31A-43. FIGS. 29A-29D illustrate one embodiment of a connector 360 which may be used with the surgical instruments disclosed herein. The connector 360 can have a proximal end 361 and a distal end 362. The proximal end of the connector 360 can have a chamber 365 configured to receive the distal end of a suitable actuator 270. The proximal end 361 of the connector 360 can also have a channel 367 configured to receive a portion of the distal end of the actuator 270. The channel 367 can have an offset shape to help thread and retain the distal end of the actuator 270 into the chamber 365. The distal end of the connector 362 can have one or more apertures 363 configured to receive one or more retaining members (not shown). FIG. 29D shows a cross-sectional view of the connector 360, taken along the section line 29D-29D in FIG. 29C. FIG. 29D shows the inner chamber 366 formed in the connector 360 and configured to receive the proximal end 351 of a suitable working rod 350.

FIG. 41 shows a cross-sectional side view of a surgical instrument 200 with a connector 360 disposed therein and engaged with a working rod 350 and the distal end of an actuator 270. A control member 388 at least partially encloses the connector 360. In FIG. 41, the smaller diameter portion 391 of the control member 388 is above the at least one retaining member 368 forcing the retaining member 368 to project into the smaller diameter portion 354 of the working rod 350 and locking the working rod 350 to the connector 360. However, the control member 388 may be moved in the distal direction such that the larger diameter portion 393 is above the at least one retaining member 368. With the control member 388 in this position, the working rod 350 can be pulled out of the inner chamber 366 of the connector 360 because the retaining member 368 can move up into the space formed by the larger diameter portion 393.

FIG. 32-39B illustrate a system for translating the control member 388 between a first zone where the at least one retaining member is maintained in the locking position, and a second zone where the at least one retaining member can move to an unlocked position. The control member 388 can be disposed within the translation guide 397 with the translation members 394 of the control member threaded into the channels 384 of the translation guide 397. The translation members 394 can also be inserted into the channels 373 formed within the hollow body 372. FIG. 38B shows the translation members 394 of the control member 388 disposed within the channels 373 of the hollow body 372. Rotating the hollow body 372 clockwise with respect to the rotation knob 275 will translate the control member 388 in the distal direction, allowing the working rod 350 to be unlocked from the connector 360. Rotating the hollow body 372 counterclockwise with respect to the rotation knob 275 will translate the control member 388 in the proximal direction, locking the working rod 350 to the connector 360. The one or more channels 384 in the translation member 397 can have a pitch that allows for sufficient translation of the control member 388, in either direction, using a quarter turn rotation of the hollow body 372 with respect to the rotation knob 275. The spheres 383 and depressions 374 can interact with each other to produce tactile feedback to help the user know when the quarter turn of the hollow body 372 has been reached in either direction.

A retaining pin (not shown) may be inserted through an aperture 379 formed in the side of the rotation knob 275, as seen in FIG. 33. The retaining pin may project, at least partially, into the inside of the inner chamber of the rotation knob 275 and engage an annular groove 250 formed within the larger diameter portion 251 of the hollow shaft 242 of the pivot housing 241. In this configuration, the retaining pin will not permit the rotation knob 275 to move translationally with respect to the longitudinal axis 283 of the working shaft 282, yet the retaining pin will allow the rotation knob 275 to rotate freely about the longitudinal axis of the working shaft 282.

Figure 44:
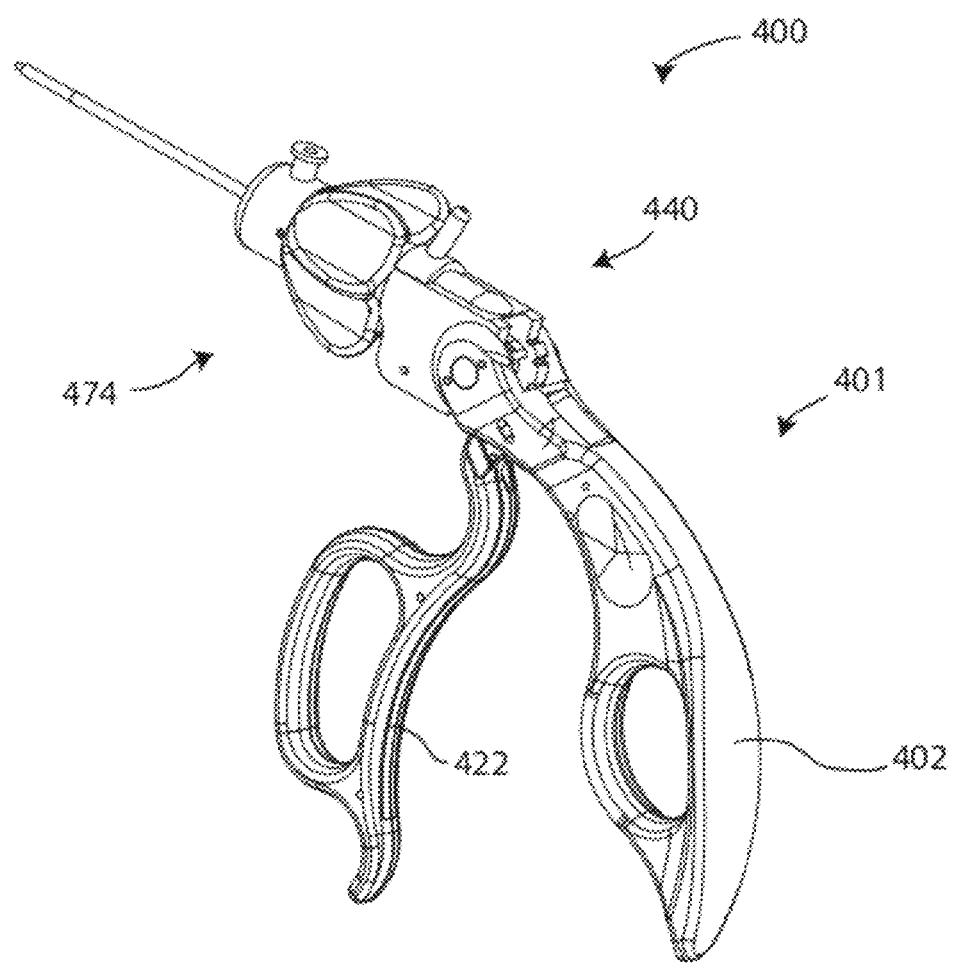
FIG. 44 is an isometric view of a surgical instrument with an adjustable handle section according to another embodiment of the present disclosure.

In FIGS. 44-59C, a surgical instrument 400 in accordance with another embodiment of the present disclosure is illustrated. FIG. 44 shows an isometric view of a surgical instrument 400 having a working shaft section 474 at its distal end, a handle section 401 at its proximal end, and a pivot section 440 intermediate the working shaft section 474 and the handle section 401. The handle section 401 may include a first handle 402 and a second handle 422.

Figure 45:
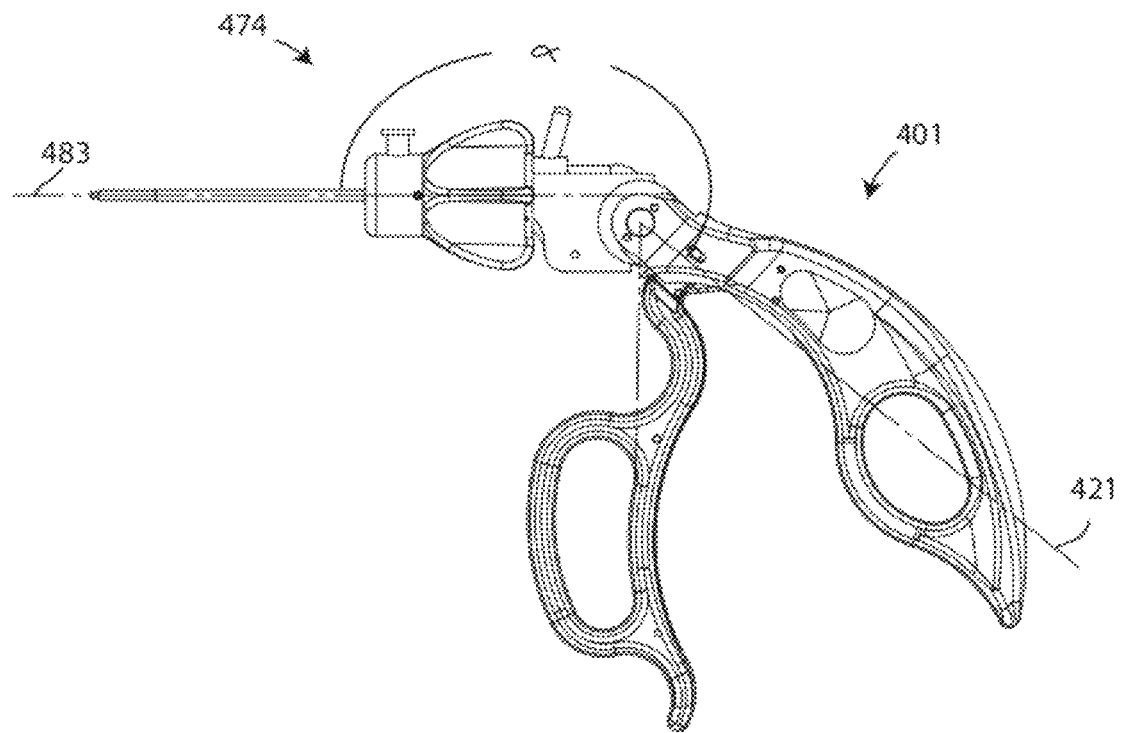
FIG. 45 is a side view of the surgical instrument of FIG. 44 with the handles of the surgical instrument in a "drop-down" position.
Figure 46:
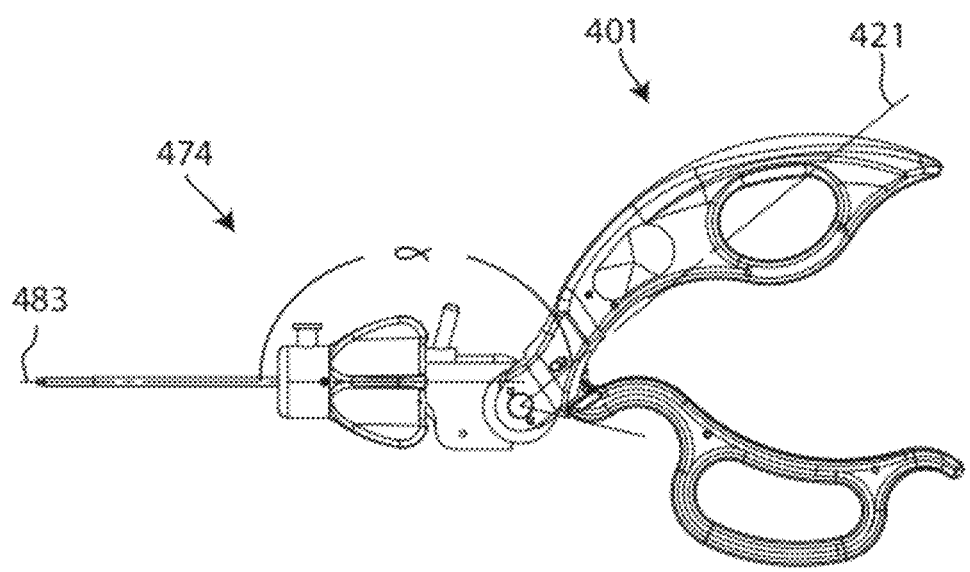
FIG. 46 is a side view of the surgical instrument of FIG. 44 with the handle section of the surgical instrument in an "up-angled" position.

FIG. 45 shows a side view of the surgical instrument 400 of FIG. 44 with the handle section 401 adjusted in a "dropdown" position relative to the longitudinal axis 483 of the working shaft section 474, similar to other embodiments disclosed herein. FIG. 46 shows a side view of the surgical instrument 400 of FIG. 44 with the handle section 401 adjusted in an "angled-up" position relative to the working shaft section 474.

FIGS. 47-50B show various exploded views of the surgical instrument 400 for each subsection of the surgical instrument 400. FIGS. 51A-56C illustrate the individual components of FIGS. 47-50B in greater detail. A detailed description of the structure and features for each individual component will be given in a generally proximal to distal direction with reference to FIGS. 51A-56C. A detailed description of how each of the individual components interrelate with one another will then be given, along with the functional relationships between each component. Methods of using the surgical instrument 400 will also be given to illustrate how a surgeon can utilize the surgical instrument 400 to achieve greater ergonomic postures during surgery.

FIGS. 51A-51C show various isometric views of a first handle 402, according to one embodiment of the present disclosure. The first handle 402 has a proximal end 496 and a distal end 497. The first handle 402 can have a top surface 405, a bottom surface 415, and two side surfaces 404. The top surface 405 can have a spatulate shape and/or curve downward in the distal to proximal direction to better conform to the surgeon's palm. In some embodiments, the top surface 405 can have a radius of curvature, or substantially lie along a radius of curvature. In some embodiments, the radius of curvature can be between about 2 and 4 inches. In other embodiments, the radius of curvature can be between about 2.5 inches and 3.5 inches. In a particular embodiment, the radius of curvature is about 2.9 inches.

The top surface 405 of the first handle 402 may have a convex or rounded shape in the lateral direction between the two side surfaces 404 of the first handle 402. The top surface 405 is preferably shaped to be substantially wide enough between the two side surfaces 404 to provide adequate comfort to the surgeon's palm by providing sufficient surface contact area between the top surface 405 and the surgeon's palm to reduce or eliminate "hot spots" from forming on the surgeon's palm. The top surface 405 can have a maximum width and a minimum width in the lateral direction between the two side surfaces. In some embodiments, the minimum width of the top surface is located closer to the distal end of the first handle and the maximum width of the top surface is located closer to the proximal end of the first handle. In other embodiments the minimum width is between about 0.25 inches and about 0.75 inches. In a particular embodiment, the minimum width is about 0.5 inches. In some embodiments, the maximum width is between about 0.5 inches and about 1.25 inches. In one embodiment, the maximum width is about 0.88 inches. The location of the minimum width of the top surface can be chosen to correspond to the area of the top surface 405 that the surgeon's thumb traverses when the surgeon switches between a "finger loop" grip style and a "palm" grip style. Having the minimum width of the top surface in this area of the top surface 405 can allow the surgeon to more easily switch between the "finger loop" grip style and the "palm" grip style because the smaller width makes it easier for the surgeon's thumb to traverse this area of the handle.

The top surface 405 may include a button slot 419 configured to receive a portion of a ratcheting mechanism, such as a button. Moreover, the side surfaces 404 may include a thumb or finger rest area 408 formed on or into the side surfaces 404 to provide extra support for the surgeon's thumb when engaged along the side surface 404. The first handle 402 may have one or more finger loop holes 410 to receive one or more fingers during procedures requiring greater precision. The finger loop hole contact surface 409 may be convex in shape and wide enough to avoid or eliminate any "hot spots" from occurring on the surgeon's fingers during extended hours of operation. The first handle 402 can have a projection portion 411 at the proximal end 496 of the first handle 402. The projection portion 411 may provide greater surface area to interact with the surgeon's palm against the top surface 405. In one embodiment, the projection portion 411 can include an electrical connector to receive external input. The first handle 402 can also have a bottom surface recess area 414 having a concave shape configured to interact with one or more of the surgeon's fingers as needed.

Any or all of the surfaces of the first handle 402 may include a comfort material (not shown) attached to one or more of the surfaces of the first handle 402, such as a soft rubber, polymer, or silicone. The comfort material may be applied to the first handle 402 after manufacture, or the comfort material may be integrally formed or molded to the first handle 402 during manufacture by any suitable manufacturing processes including, but not limited to, bonding or over-molding.

The distal end 497 of the first handle 402 may include a head portion 412 for receiving a suitably shaped pivot housing 441 into the pivot housing slot 417. The head portion 412 may have stop pin holes 403 formed through both sides of the head portion 412 for receiving stop pins 468, as will be discussed in further detail below. The head portion 412 can have a pivot pin hole 406 formed through the head portion 412 configured to receive a pivot pin 464. The first handle 402 may include a pin hole 407 formed through, or substantially through, the side surfaces 404 of the first handle 402 and configured to receive a pivot pin 435 to pivotably secure a second handle 422. In this embodiment, the surgical instrument 400 includes a dual pivot design with a first pivot connecting the handle section 401 to the working shaft section 474, and a second pivot connecting the second handle 422 to the first handle 402. Moreover, the first and second pivots are not coaxial with each other in this embodiment.

Referring to FIG. 51C, the first handle 402 may include a receiver slot 413 configured and shaped to receive the head portion 427 of a suitable second handle 422, as will be discussed in further detail below. FIG. 51C also illustrates the pivot housing slot 417 configured to receive a suitable pivot housing 441, in greater detail. FIG. 51C also illustrates an actuator aperture 418 formed within the first handle 402 proximal to the head portion 412 and shaped to allow an actuator 470 to be disposed therethrough. The first handle 402 may also have a ratchet slot 498 formed therein and configured to receive a suitable ratcheting mechanism, as will be discussed in greater detail below.

Figure 52A:
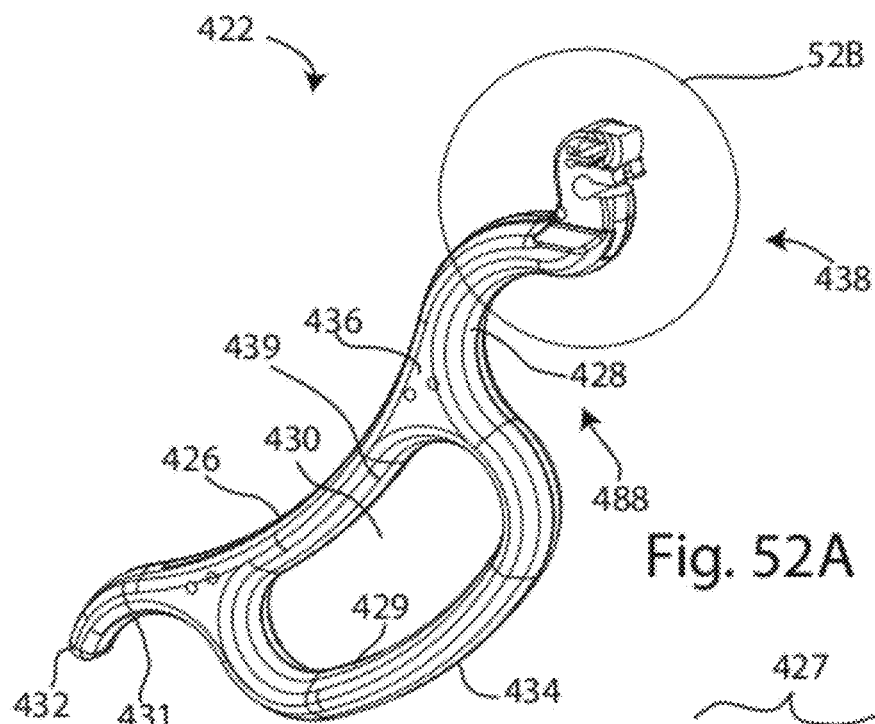
FIG. 52A is an isometric view of a second handle in accordance with another embodiment of the present disclosure.
Figure 52B:
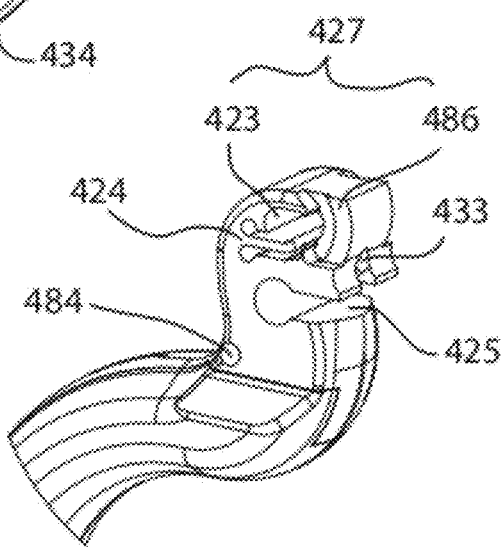
FIG. 52B shows an enlarged view of the encircled area in FIG. 52A.

Referring now to FIGS. 52A-52B, a second handle 422 in accordance with one embodiment of the present disclosure is shown. The second handle 422 can have a proximal end 437 and a distal end 438. The second handle 422 can also have a top surface 426, a bottom surface 434, and two side surfaces 436. Each of the aforementioned surfaces may have a generally rounded or convex shape to increase comfort. The top surface 426 of the second handle 422 may have a slight "S-shaped" curvature formed therein moving in the distal to proximal direction. The distal end 438 of the second handle 422 may include a head portion 427 configured to interact with the receiver slot 413 of the first handle 402, as shown in FIGS. 51A-51C. The second handle 422 can have retainer members 486, a ramp pivot hole 484 and a ramp pivot slot (not shown), which will be discussed in greater detail below.

The second handle 422 may have one or more finger loop holes 430 configured to receive one or more of the surgeon's fingers during procedures that require greater precision. The inner contact surface 429 of the finger loop hole 430 may have a rounded or convex shape to comfortably engage the fingers of the surgeon.

The second handle 422 may have at least one finger contact surface. Moreover, the at least one finger contact surface can be configured to substantially lie along a radius of curvature. The radius of curvature can be between about 1.5 and 3.5 inches in some embodiments. In other embodiments, the radius of curvature may be between about 2 inches and 3 inches. In a particular embodiment, the radius of curvature is about 2.5 inches.

In one embodiment, the second handle 422 can have a finger loop 430 defining a first finger contact surface 439 configured to receive the surgeon's ring finger and middle finger, a projection 432 configured to receive the surgeon's pinky finger, and a recess portion 488 forming a third finger contact surface 428 configured to receive the surgeon's index finger. Moreover, one or more of these finger contact surfaces can substantially lie along a radius of curvature. For example, the first and second finger contact surfaces can substantially lie along a radius of curvature of about 2.5 inches and the third finger contact surface can be offset from the radius of the curvature of the first and second finger contact surfaces by about 0.0625 inches.

Any or all of the surfaces of the second handle 422 may include a comfort/grip-enhancing material (not shown) attached to one or more of the surfaces of the second handle 422, such as a soft rubber, polymer, or silicone material. The comfort/grip-enhancing material may be applied to the second handle 422 after manufacture, or alternatively the comfort/grip-enhancing material may be integrally formed or molded to the second handle 422 during manufacture by several manufacturing processes, such as, bonding or overmolding.

Continuing with FIG. 52B, the head portion 427 of the second handle 422 can have a latch release cavity 423 formed through the head portion 427. The latch release cavity 423 may have an oblong or elongated oval shape configured to receive a pivot pin 435 to allow the pivot pin 435 to move translationally within the latch release cavity 423. The latch release cavity 423 can have a spring detent 424 just below the latch release cavity 423 to help control and bias the translational movement of the pivot pin 435, as will be discussed in greater detail below. The head portion 427 can have an actuator bore 433 formed through the head portion 427 and in communication with an actuator connection recess 425.

Figure 47:
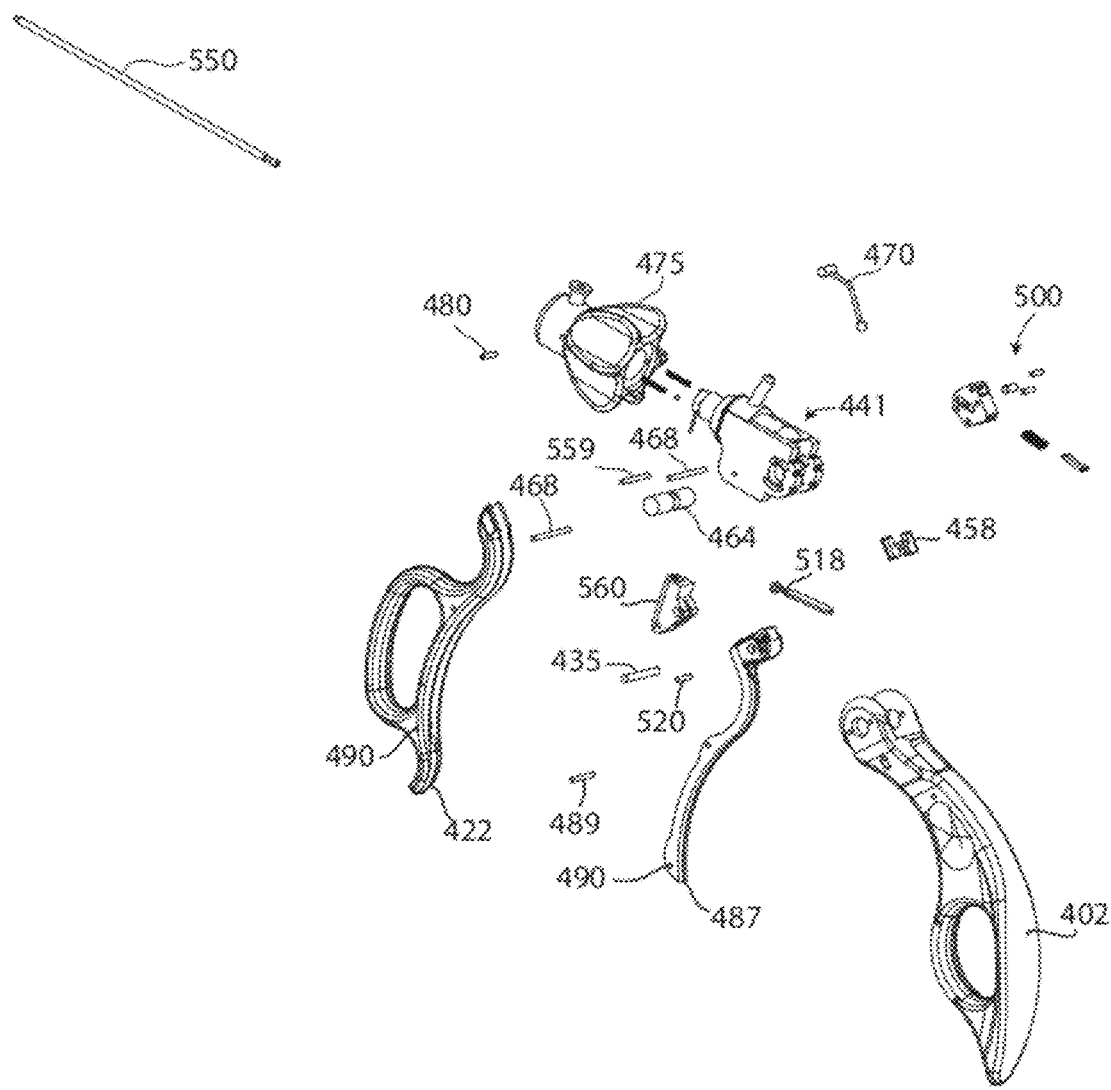
FIG. 47 is an exploded view of the surgical instrument of FIG. 44.
Figure 48A:
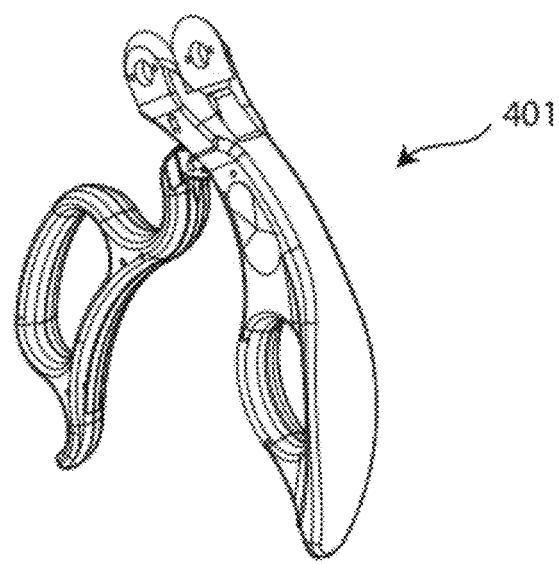
FIG. 48A is an isometric view of the handle section of the surgical instrument of FIG. 44.
Figure 48B:
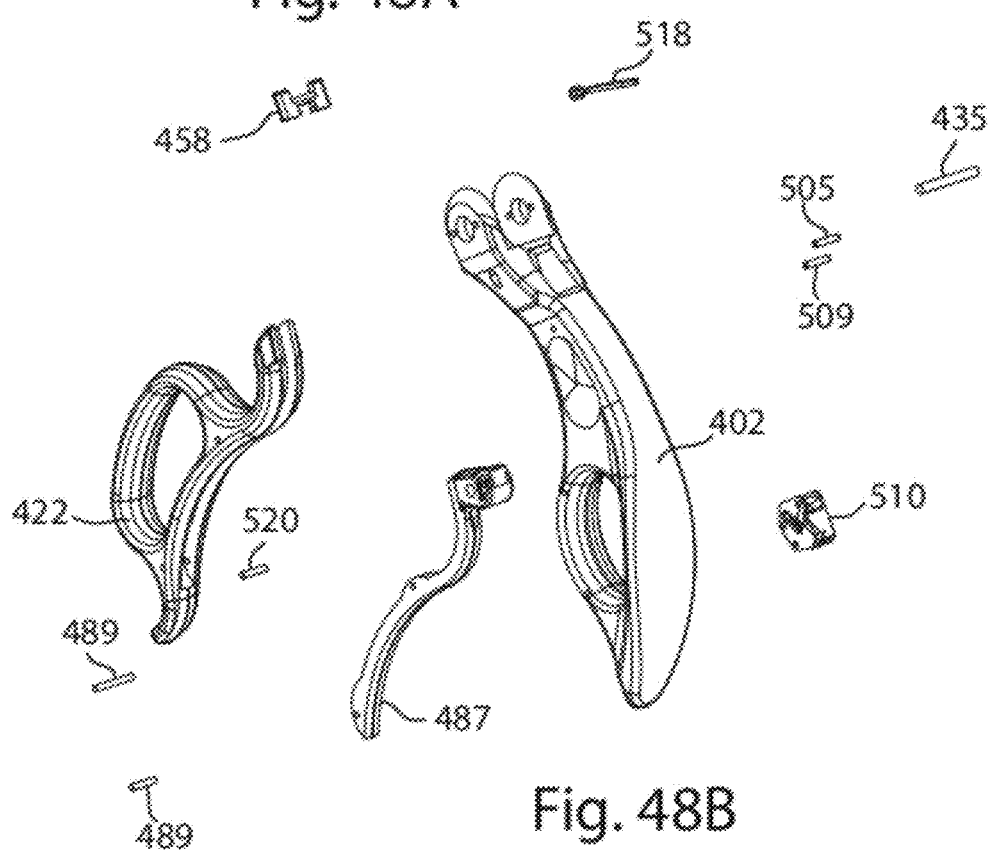
FIG. 48B is an exploded view of the handle section of FIG. 48A.
Figure 49:
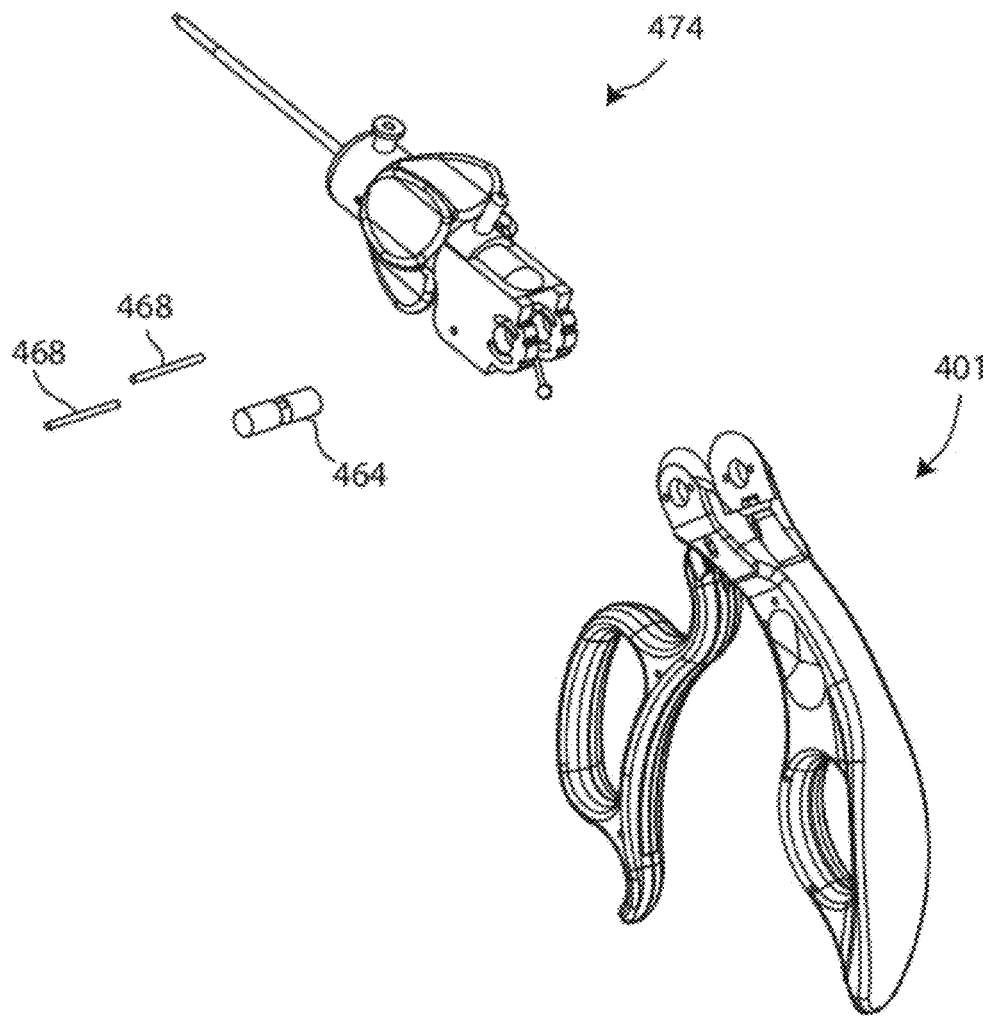
FIG. 49 is an isometric view of the surgical instrument of FIG. 44 with the handle section separated from the working shaft section.
Figure 50A:
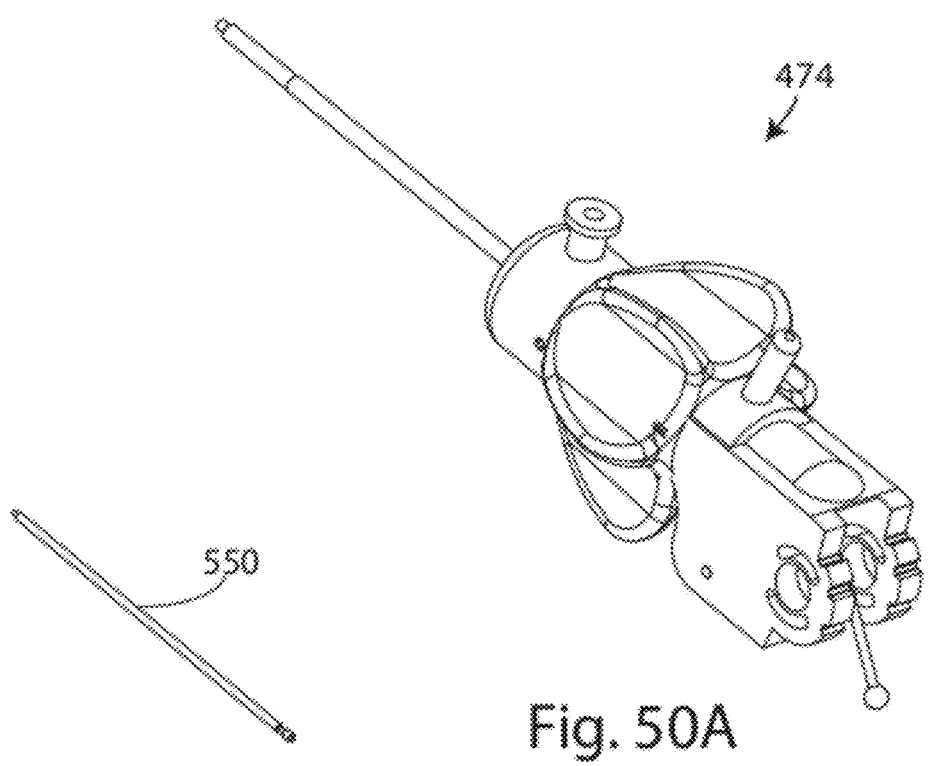
FIG. 50A is an enlarged view of the working shaft section of FIG. 49.
Figure 50B:
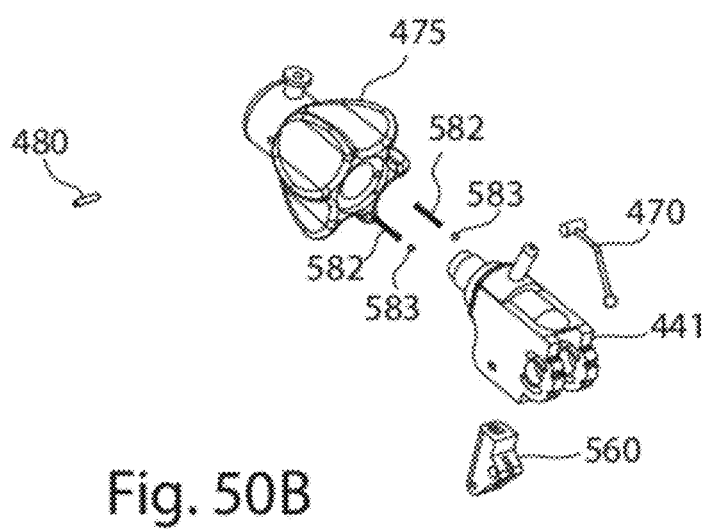
FIG. 50B is an exploded view of the working shaft section of FIG. 50A.

FIG. 47 shows one embodiment of a multi-component second handle 422 having a removable top portion 487 which may be attached to the second handle 422 with one or more pins 489 threaded through pin holes 490. In other embodiments, the second handle 422 may comprise an alternative control member such as a trigger, a button, a lever, a truncated handle or any other structure suitable for a surgical instrument. In some embodiments, the second handle 422 may be omitted entirely.

Figure 53A:
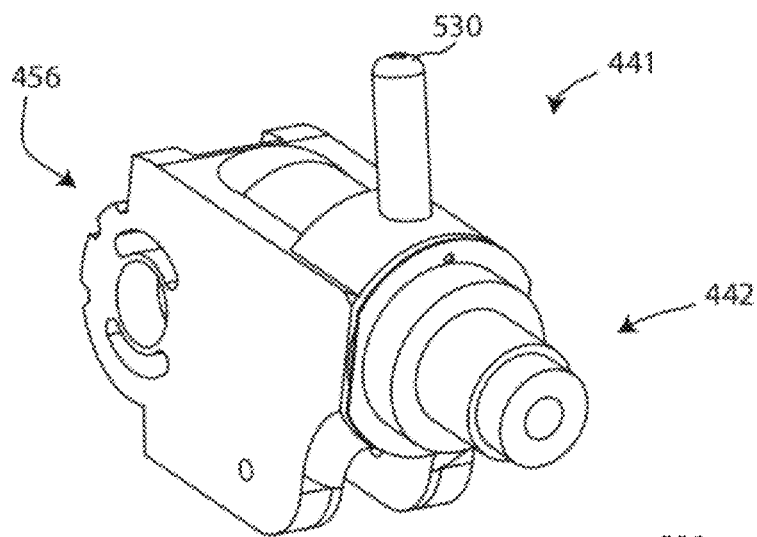
FIG. 53A is an isometric view of the pivot housing in accordance with another embodiment of the present disclosure.
Figure 53B:
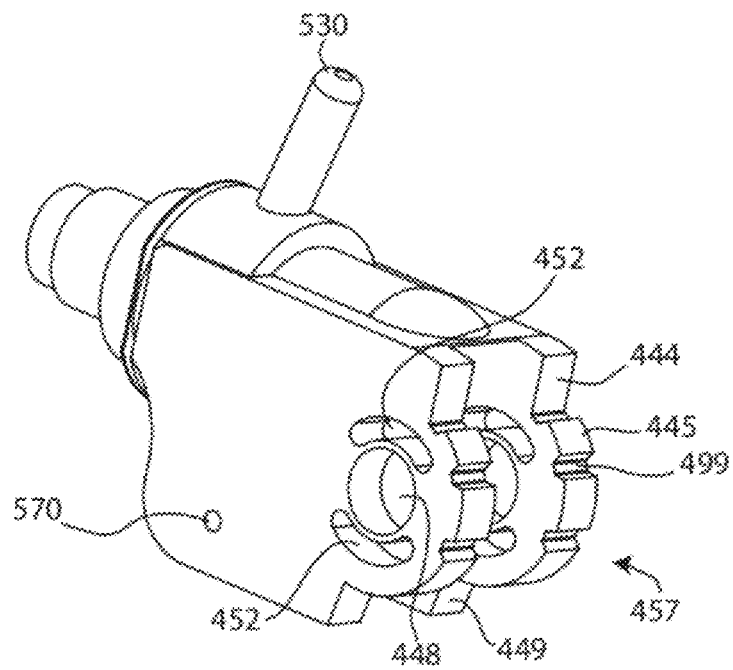
FIG. 53B is another isometric view of the pivot housing of FIG. 53A.

FIGS. 53A-53B show a pivot housing 441, in accordance with one embodiment of the present disclosure. The pivot housing 441 may include a hollow shaft 442 pivot head portion 456. The pivot head portion 456 may have a top angled surface 444 and a bottom angled surface 449. The pivot head portion 456 may include a pivot pin hole 448 formed through the pivot head portion 456. Additionally, the pivot head portion 456 may include stop pin slots 452 formed through the pivot head portion 456 having elongated and curved oval shapes. The pivot head portion 456 may also include one or more locking teeth 445, and/or one or more locking member receiver slots 499, formed in a surface of the pivot head portion 456. The pivot housing 441 can also have a pin hole 570 configured to receive a pivot pin 559 to pivotably connect a suitable connector 560 within the pivot housing 441. In some embodiments, the pivot housing 441 can also have an input port 530 to receive external input, such as electricity or a fluid.

Figure 54A:
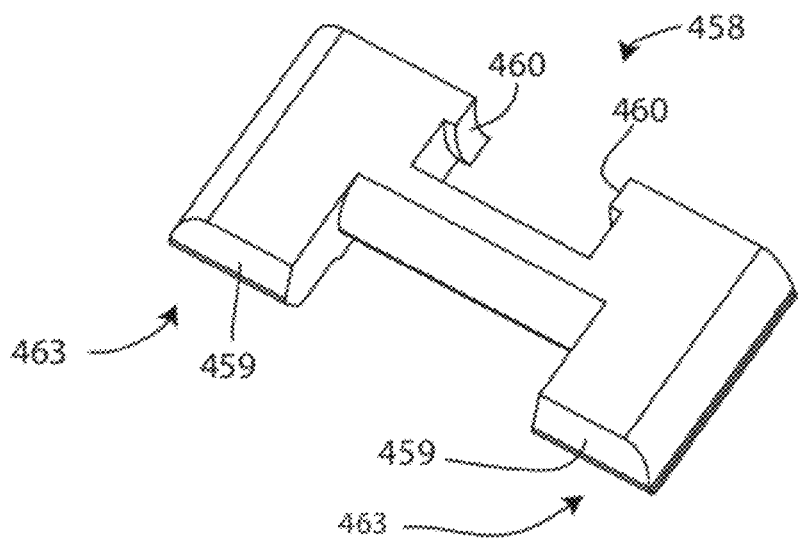
FIG. 54A is an isometric view of a locking member in accordance with another embodiment of the present disclosure.

FIG. 54A shows a locking member 458 in accordance with one embodiment of the present disclosure. The locking member 458 may have one or more locking surfaces 463 including one or more locking teeth 459 formed in a surface of the locking member 458 and configured to engage the locking surface 457 of a suitable pivot housing 441, which can also include one or more teeth 445, and or one or more locking member receiver slots 499. The locking member 458 can also have projections 460 configured to interact with retainer members 486 formed on the head portion 427 of the second handle 422 to keep the locking member 458 engaged with the second handle 422.

Figure 54B:
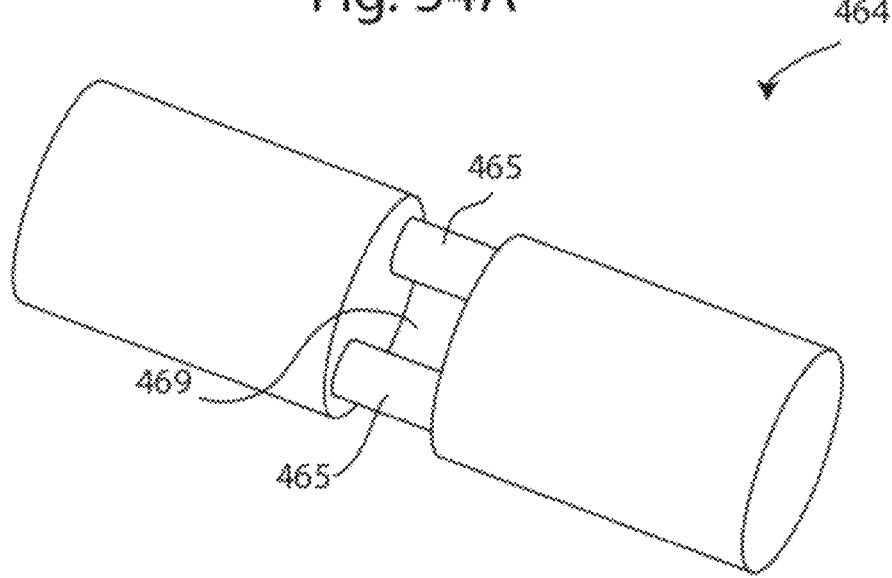
FIG. 54B is an isometric view of the pivot pin in accordance with another embodiment of the present disclosure.

FIG. 54B shows an isometric view of a pivot pin 464 according to another embodiment of the present disclosure. The pivot pin 464 may have a guide hole 469 formed through the center of the pivot pin 464 between one or more connecting members 465. The guide hole 469 can restrain an actuator 470 along the centerline of the joint as the handle section 401 pivots relative to the working shaft section 482.

Figure 55A:
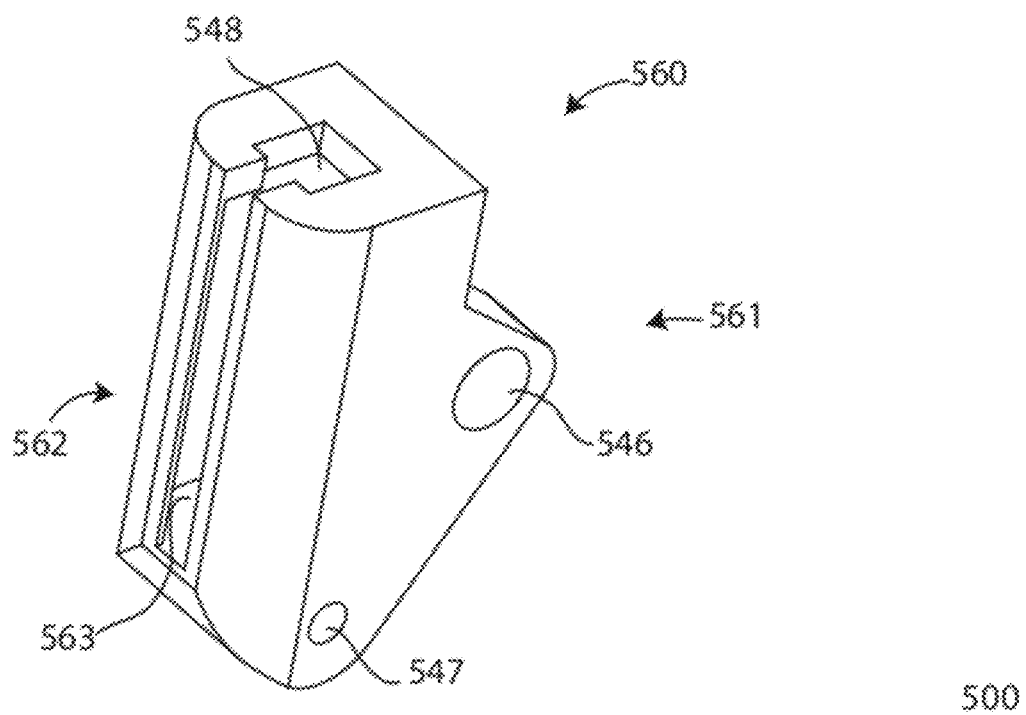
FIG. 55A is an isometric view of a connector in accordance with another embodiment of the present disclosure.
Figure 55B:
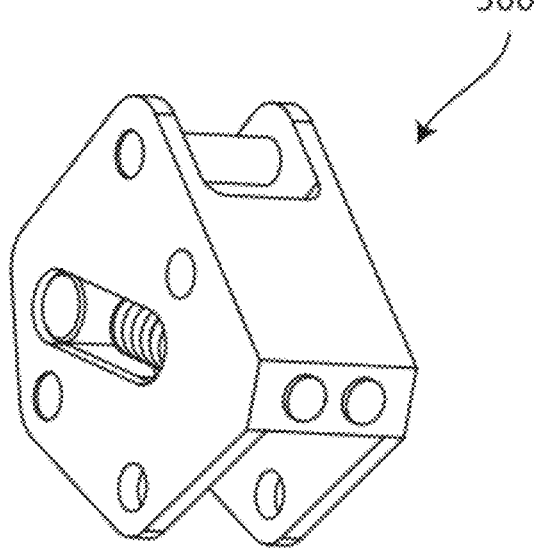
FIG. 55B is an isometric view of the ratchet mechanism in accordance with another embodiment of the present disclosure.
Figures 56A, 56B:
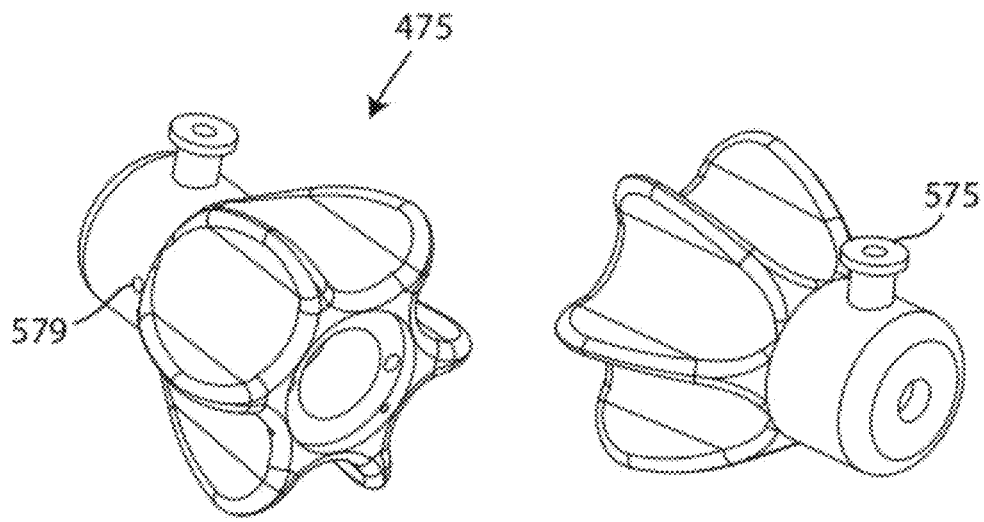
FIG. 56A is an isometric view of a rotation knob according to another embodiment of the present disclosure.
FIG. 56B is another isometric view of the rotation knob of FIG. 56A.
Figures 56C, 56D:
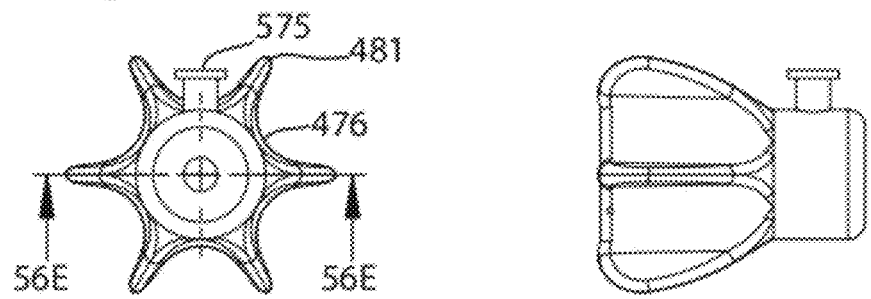
FIG. 56C say front view of the rotation knob of FIG. 56A having a section line 56E-56E.
FIG. 56D is a side view of the rotation knob of FIG. 56A.
Figure 56E:
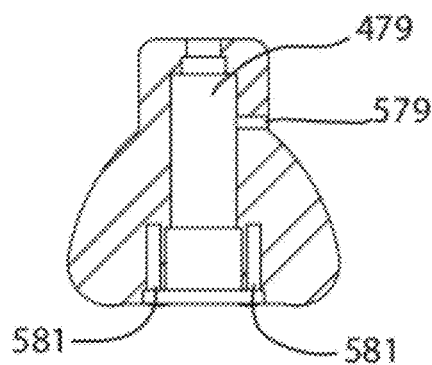
FIG. 56E is a cross-sectional side view of the rotation knob of FIG. 56C, taken along the section line 56E-56E in FIG. 56C.
Figure 57A:
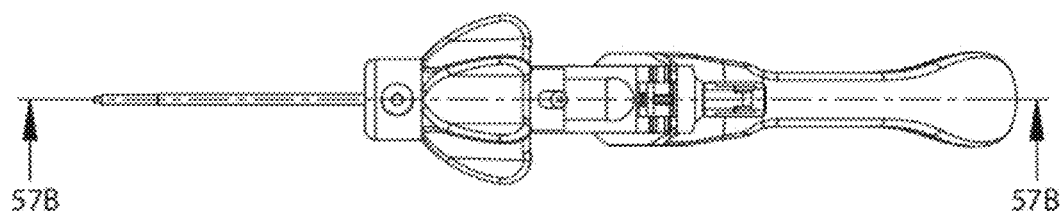
FIG. 57A is a top view of the surgical instrument shown in FIG. 45 with the second handle in the "at rest" position and having a section line 57B.
Figure 57B:
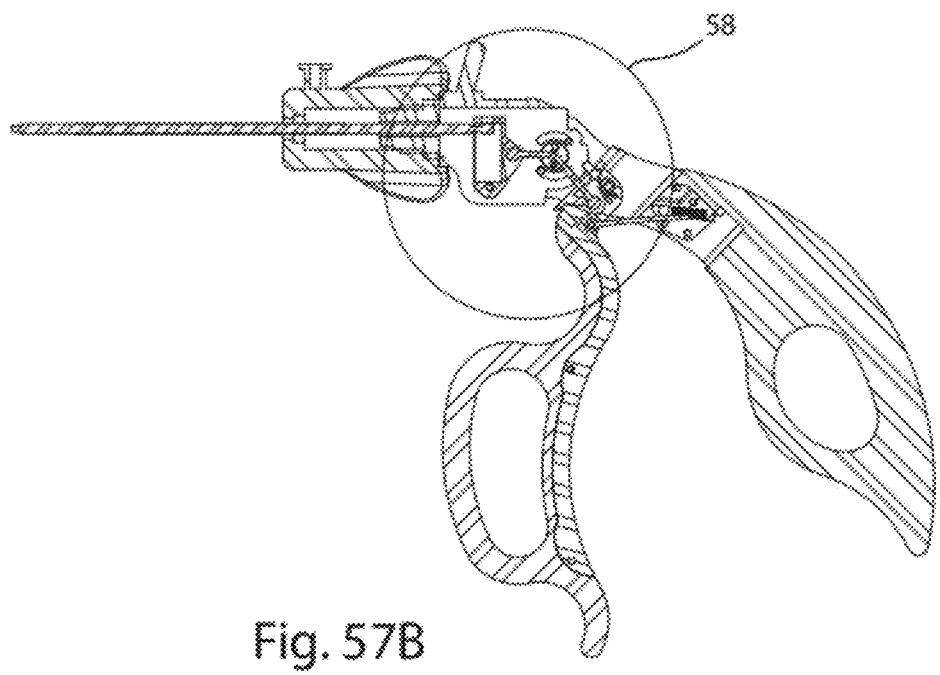
FIG. 57B is a cross-sectional side view of the surgical instrument of FIG. 57A, taken along the section line 57B-57B in FIG. 57A.

FIG. 55A illustrates one embodiment of the connector 560 which may be used with the surgical instruments disclosed herein. The connector 560 can have a proximal end 561 and a distal end 562. The proximal end 561 of the connector 560 can have a pin hole 546 configured to receive a suitable pivot pin (not shown) threaded through the distal end of a suitable actuator 470 to pivotably connect the actuator 470 to the connector 560. The distal end 562 of the connector 560 can have a connection aperture 548 in communication with a longitudinal aperture 563 configured to receive the proximal end 551 of a suitable working rod 550. FIG. 55B shows a portion of a ratcheting mechanism 500, similar to other ratcheting mechanisms discussed herein, which can be used in with surgical instruments disclosed herein.

FIGS. 56A-56E show a rotation knob 475 in accordance with another embodiment of the present disclosure. The rotation knob 475 can have one or more ribs 481 and one or more depressions 476 formed in the outer surface of the rotation knob 475. The rotation knob 475 can also have one or more longitudinal apertures 581 configured to receive springs 582 and spheres 583 therein. The rotation knob 475 may also have a port 575 connected to a surface of the rotation knob 475. The port 575 can be in communication with the inner chamber of the rotation knob 475 and can be used as an aid in the cleaning process. For example, pressurized water can be forced into the port 575 to help clean the inside of the rotation knob 475. The rotation knob 475 can be held in place with a suitable retaining pin 480 disposed within aperture 579, similar to other embodiments disclosed herein.

Figure 58:
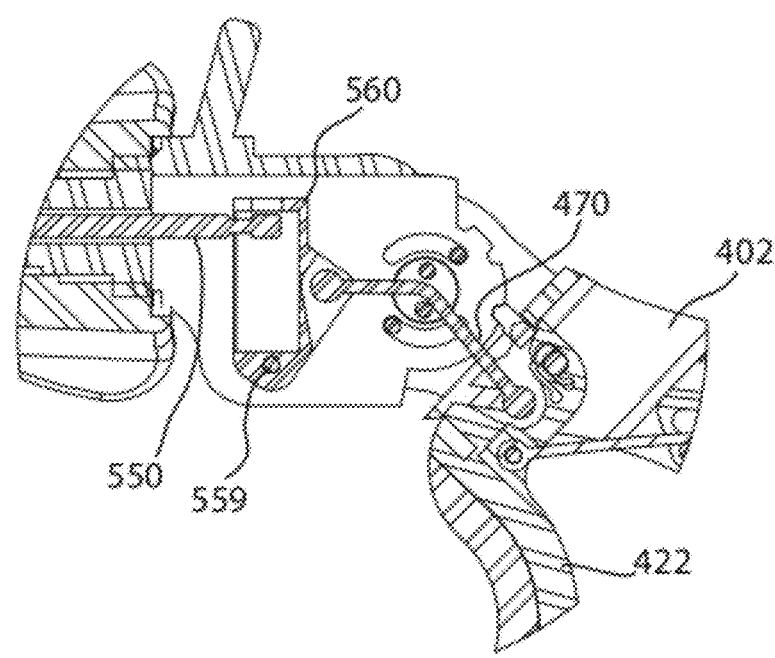
FIG. 58 shows an enlarged view of the encircled area in FIG. 57B.
Figure 59A:
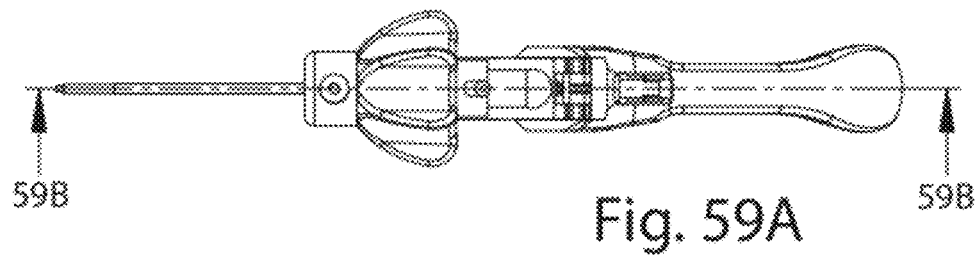
FIG. 59A is a top view of the surgical instrument shown in FIG. 45 with the second handle in the "forward" position and having a section line 59B-59B.
Figure 59B:
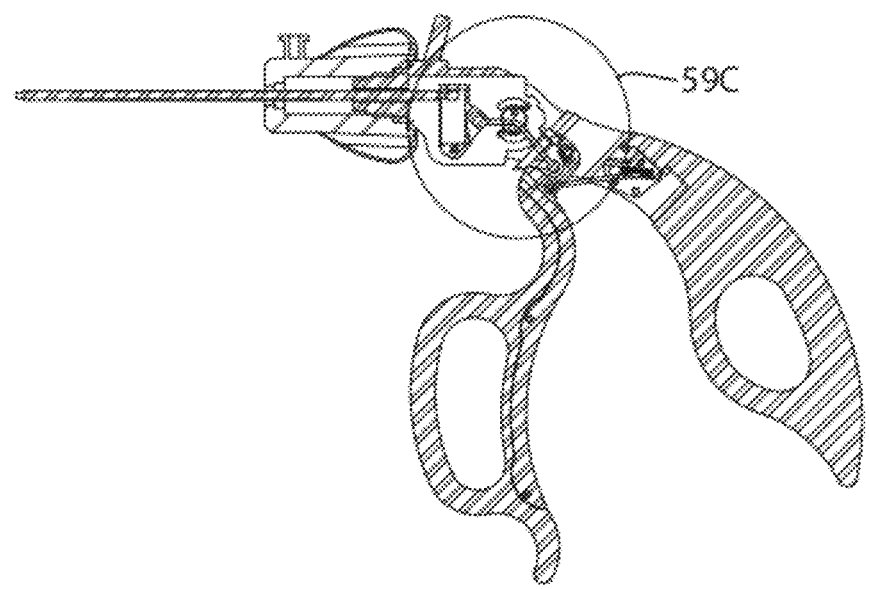
FIG. 59B is a cross-sectional side view of the surgical instrument of FIG. 59A, taken along the section line 59B-59B in FIG. 59A.
Figure 59C:
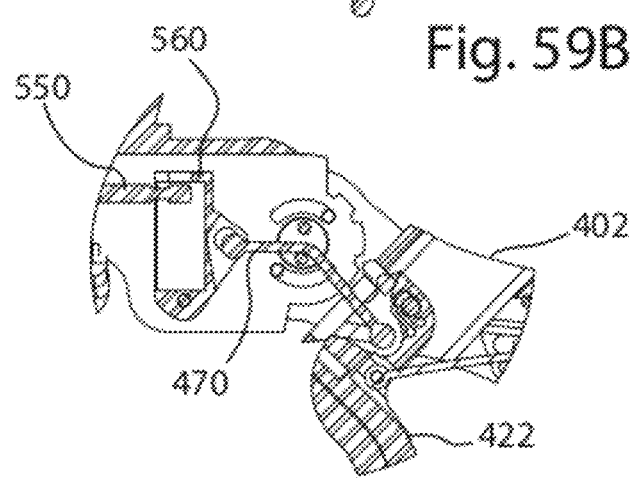
FIG. 59C is an enlarged view of the encircled area in FIG. 59B.

The operation of the actuator 470 and connector 560 between the second handle 422 and the working rod 550 will now be explained with reference to FIGS. 57A-59C. Referring to FIG. 58, the actuator 470 is pivotably connected to the connector 560 with a suitable pivot pin threaded through pin hole 546. Rotating the second handle 422 toward the first handle 402 will pull the actuator 470 in the proximal direction causing the connector 560 to pivot toward the proximal direction pulling the working rod 550 in the proximal direction. The working rod 550 can move translationally within the longitudinal aperture 563 of the connector 560 as the connector pivots back and forth. With a suitable actuator 470 having rigid portions, as disclosed in other embodiments herein, the working rod can also be moved in the distal direction by rotating the second handle 422 away from the first handle 402. The connector 560 can also have an aperture 548 configured to receive the proximal end of a working rod 550 and allow the working rod 550 to be coupled and decoupled from the connector 560.

Figure 60:
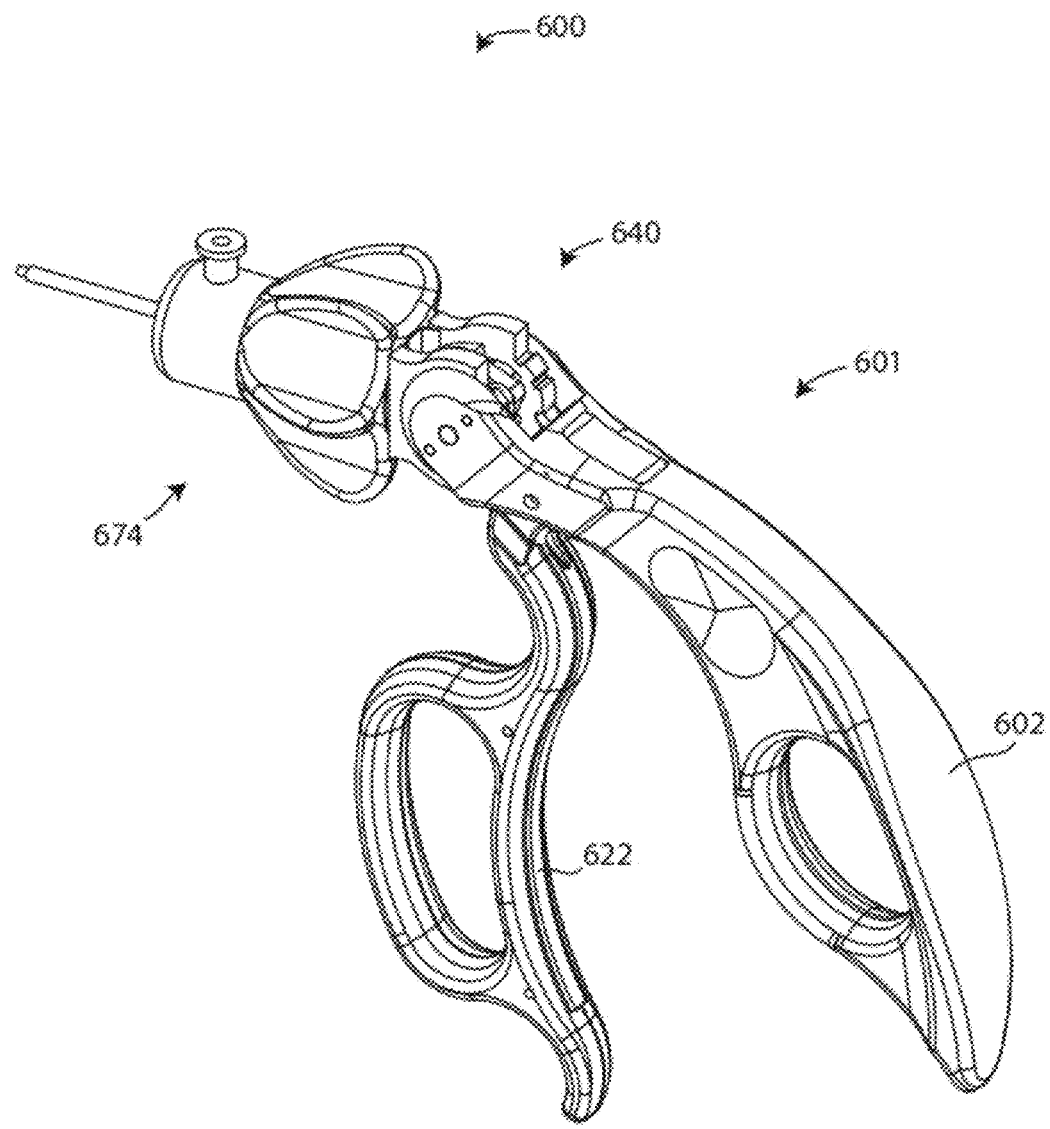
FIG. 60 is an isometric view of a surgical instrument with an adjustable handle section according to another embodiment of the present disclosure.

In FIGS. 60-83, a surgical instrument 600 in accordance with another embodiment of the present disclosure is illustrated. FIG. 60 shows an isometric view of a surgical instrument 600 having a working shaft section 674 at its distal end, a handle section 601 at its proximal end, and a pivot section 640 intermediate the working shaft section 674 and the handle section 601. The handle section 601 may include a first handle 602 and a second handle 622. FIGS. 61-65 show side views of the surgical instrument 600 of FIG. 60 with the handle section

601 and the second handle 622 adjusted in various positions relative to the longitudinal axis 683 of the working shaft section 674, similar to other embodiments disclosed herein.

Figure 66:
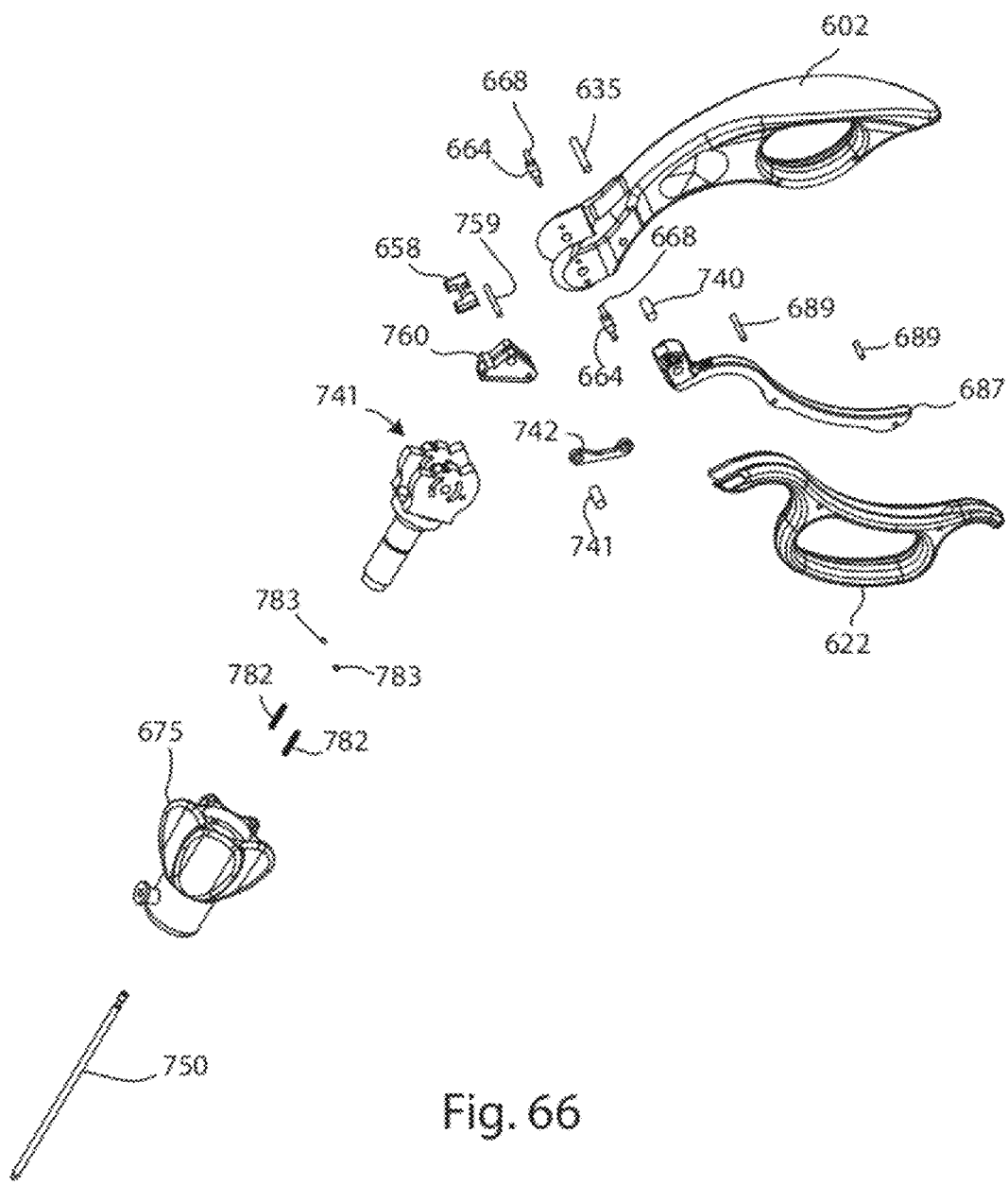
FIG. 66 is an exploded view of the surgical instrument of FIG. 60.

FIG. 66 shows an exploded view of the surgical instrument 600. FIGS. 67A-73E illustrate the individual components of FIG. 66 in greater detail. A detailed description of the structure and features for each individual component will be given in a generally proximal to distal direction with reference to FIGS. 67A-73E. A detailed description of how each of the individual components interrelate with one another will then be given, along with the functional relationships between each component. Methods of using the surgical instrument 600 will also be given to illustrate how a surgeon can utilize the surgical instrument 600 to achieve greater ergonomic postures during surgery.

Figure 67A:
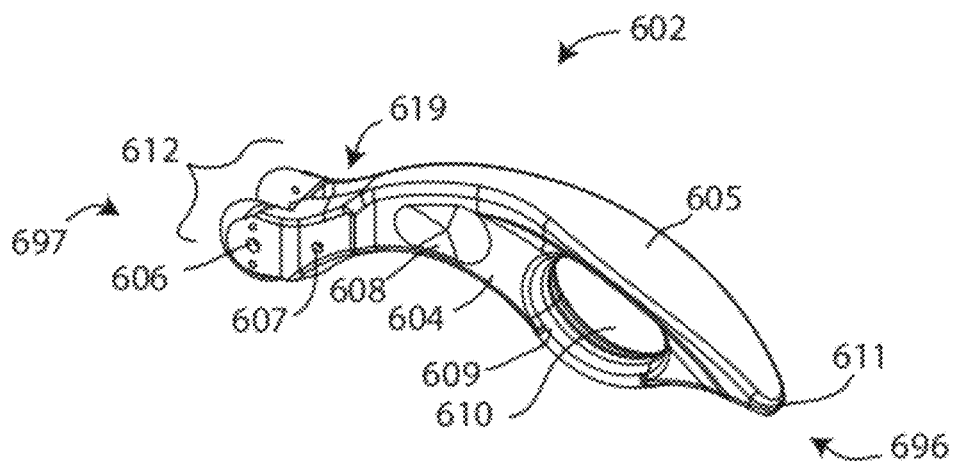
FIG. 67A is an isometric view of a first handle according to another embodiment of the present disclosure.
Figure 67B:
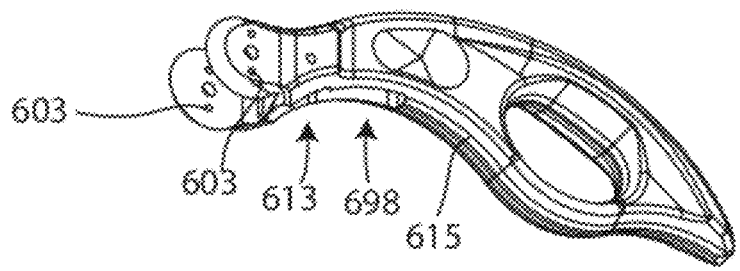
FIG. 67B is another isometric view of the first handle of FIG. 67A.
Figure 67C:
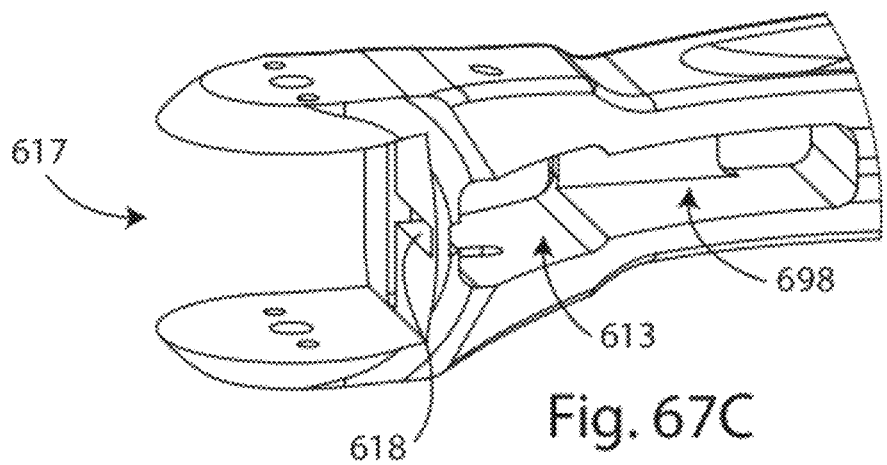
FIG. 67C is an enlarged isometric view of the distal end of the first handle of FIGS. 67A-67B.
Figure 69A:
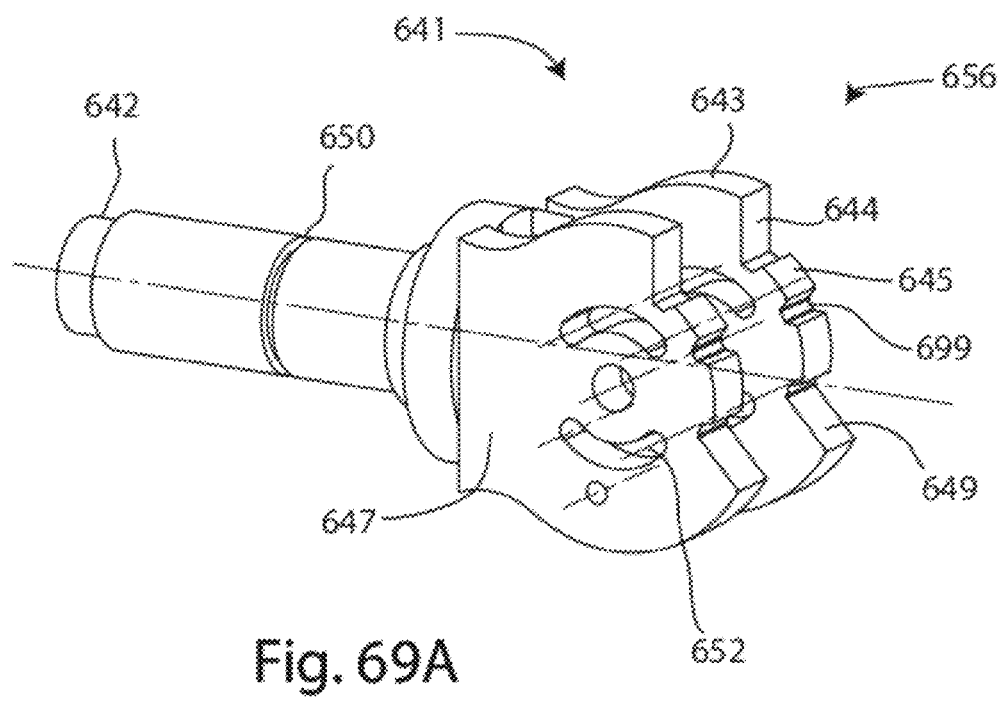
FIG. 69A is an isometric view of a pivot housing according to another embodiment of the present disclosure.
Figure 69B:
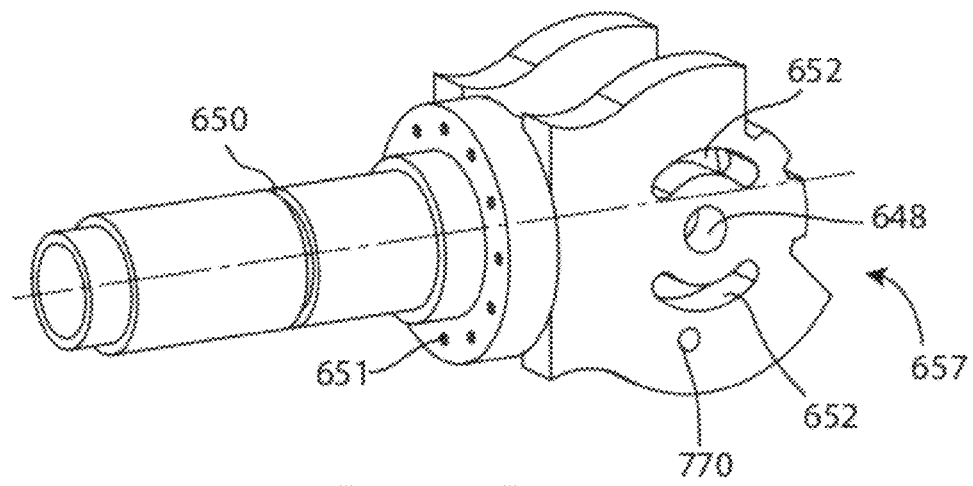
Figure 70A:
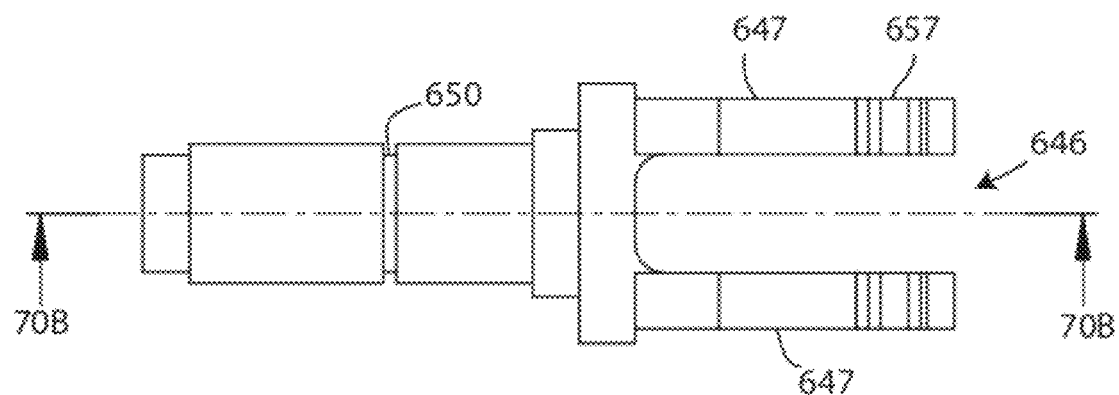
Figure 70B:
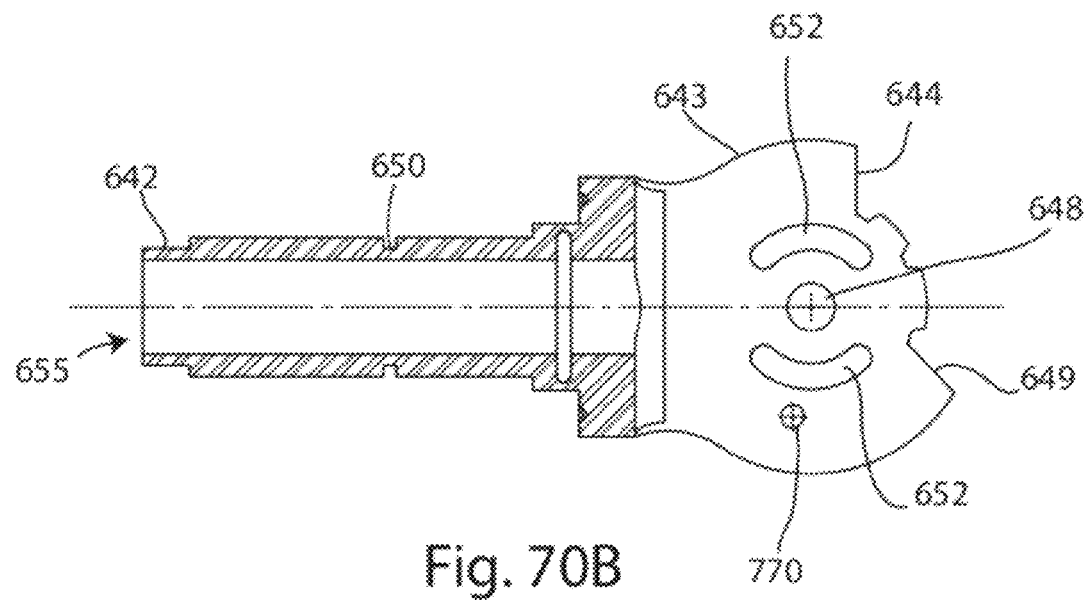

FIGS. 67A-67C show various isometric views of a first handle 602, according to one embodiment of the present disclosure. The first handle 602 has a proximal end 696 and a distal end 697. The first handle 602 can have a top surface 605, a bottom surface 615, and two side surfaces 604. The top surface 605 can have a spatulate shape and/or curve downward in the distal to proximal direction to better conform to the surgeon's palm. In some embodiments, the top surface 605 can have a radius of curvature, or substantially lie along a radius of curvature. In some embodiments, the radius of curvature can be between about 2 and 4 inches. In other embodiments, the radius of curvature can be between about 2.5 inches and 3.5 inches. In a particular embodiment, the radius of curvature is about 2.9 inches.

The top surface 605 of the first handle 602 may have a convex or rounded shape in the lateral direction between the two side surfaces 604 of the first handle 602. The top surface 605 is preferably shaped to be substantially wide enough between the two side surfaces 604 to provide adequate comfort to the surgeon's palm by providing sufficient surface contact area between the top surface 605 and the surgeon's palm to reduce or eliminate "hot spots" from forming on the surgeon's palm. The top surface 605 can have a maximum width and a minimum width in the lateral direction between the two side surfaces. In some embodiments, the minimum width of the top surface is located closer to the distal end of the first handle and the maximum width of the top surface is located closer to the proximal end of the first handle. In other embodiments the minimum width is between about 0.25 inches and about 0.75 inches. In a particular embodiment, the minimum width is about 0.5 inches. In some embodiments, the maximum width is between about 0.5 inches and about 1.25 inches. In one embodiment, the maximum width is about 0.88 inches. The location of the minimum width of the top surface can be chosen to correspond to the area of the top surface 605 that the surgeon's thumb traverses when the surgeon switches between a "finger loop" grip style and a "palm" grip style. Having the minimum width of the top surface in this area of the top surface 605 can allow the surgeon to more easily switch between the "finger loop" grip style and the "palm" grip style because the smaller width makes it easier for the surgeon's thumb to traverse this area of the handle.

The top surface 605 may include a button slot 619 configured to receive a portion of a ratcheting mechanism, such as a button. Moreover, the side surfaces 604 may include a thumb or finger rest area 608 formed on or into the side surfaces 604 to provide extra support for the surgeon's thumb when engaged along the side surface 604. The first handle 602 may have one or more finger loop holes 610 to receive one or more fingers during procedures requiring greater precision. The finger loop hole contact surface 609 may be convex in shape and wide enough to avoid or eliminate any "hot spots" from occurring on the surgeon's fingers during extended hours of operation. The first handle 602 can have a projection portion 611 at the proximal end 696 of the first handle 602. The projection portion 611 may provide greater surface area to interact with the surgeon's palm against the top surface 605. In some embodiments, the projection portion 611 can include an electrical connector to receive external input.

Any or all of the surfaces of the first handle 602 may include a comfort material (not shown) attached to one or more of the surfaces of the first handle 602, such as a soft rubber, polymer, or silicone. The comfort material may be applied to the first handle 602 after manufacture, or the comfort material may be integrally formed or molded to the first handle 602 during manufacture by any suitable manufacturing processes including, but not limited to, bonding or overmolding.

The distal end 697 of the first handle 602 may include a head portion 612 for receiving a suitably shaped pivot housing 641 into the pivot housing slot 617. The head portion 612 may have stop pin holes 603 formed through both sides of the head portion 612 for receiving stop pins 668, as will be discussed in further detail below. The head portion 612 can have a pivot pin hole 606 formed through the head portion 612 configured to receive one or more pivot pins 664. The first handle 602 may include a pin hole 607 formed through, or substantially through, the side surfaces 604 of the first handle 602 and configured to receive a pivot pin 635 to pivotably secure a second handle 622. In this embodiment, the surgical instrument 600 includes a dual pivot design with a first pivot connecting the handle section 601 to the working shaft section 674, and a second pivot connecting the second handle 622 to the first handle 602. Moreover, the first and second pivots are not coaxial with each other in this embodiment.

Referring to FIG. 67C, the first handle 602 may include a receiver slot 613 configured and shaped to receive the head portion 627 of a suitable second handle 622. FIG. 67C also illustrates the pivot housing slot 617 configured to receive a suitable pivot housing 641, in greater detail. FIG. 67C also illustrates an actuator aperture 618 formed within the first handle 602 proximal to the head portion 612 and shaped to allow an actuator 670 to be disposed therethrough. The first handle 602 may also have a ratchet slot 698 formed therein and configured to receive a suitable ratcheting mechanism.

Referring now to FIGS. 68A-68D, a portion of a second handle 687 in accordance with one embodiment of the present disclosure is shown. The second handle portion 687 can have a proximal end 637 and a distal end 638. The second handle portion 687 may include a head portion 627 configured to interact with the receiver slot 613 of the first handle 602, as shown in FIGS. 67B-67C. The head portion 627 of the second handle 622 can have a latch release cavity 623 formed through the head portion 627. The latch release cavity 623 may have an oblong or elongated oval shape configured to receive a pivot pin 635 to allow the pivot pin 635 to move translationally within the latch release cavity 623. The latch release cavity 623 can have a spring detent 624 just below the latch release cavity 623 to help control and bias the translational movement of the pivot pin 635, discussed previously. The head portion 627 can have a slot 633 formed therein and configured to receive a suitable rigid member 742, as shown in FIG. 71B. The rigid member 742 can be pivotably attached to the second handle portion 687 with a pivot pin 740 threaded through the pin hole 744.

FIGS. 69A-70B show a pivot housing 641, in accordance with one embodiment of the present disclosure. The pivot housing 641 may include a hollow shaft 642 at its distal end and a pivot head portion 656 at its proximal end. The pivot head portion 656 may have a top surface 643, a bottom surface 654, side surfaces 647, a top angled surface 644, and a bottom angled surface 649. The top surface 643 and the bottom surface 654 may have partially spherical shapes configured to receive a suitable rotation knob 675 to allow the rotation knob 675 to rotate freely about the pivot head portion 656. The pivot head portion 656 may include one or more pivot pin holes 648 formed through the pivot head portion 656 between the sides 647. Additionally, the pivot head portion 656 may include stop pin slots 652 formed through the pivot head portion 656 having elongated and curved oval shapes. The pivot head portion 656 may also include one or more locking teeth 645, and/or one or more locking member receiver slots 699, formed in a surface of the pivot head portion 656. The hollow shaft 642 may have an annular groove 650 formed therein. The annular groove 650 may be shaped and configured to receive a retaining pin (not shown) to allow the rotation knob 675 to rotate freely about the pivot housing 641, while keeping the rotation knob 675 from moving translationally with respect to the working shaft 682. The hollow shaft 642 can have an inner bore 655 in communication with the one or more pivot pin holes 648 and a proximal opening 646 in the pivot head portion 656. The pivot housing 641 can also have a pin hole 770 to pivotably connect a suitable connector 760 within the pivot housing 641.

Figure 71A:
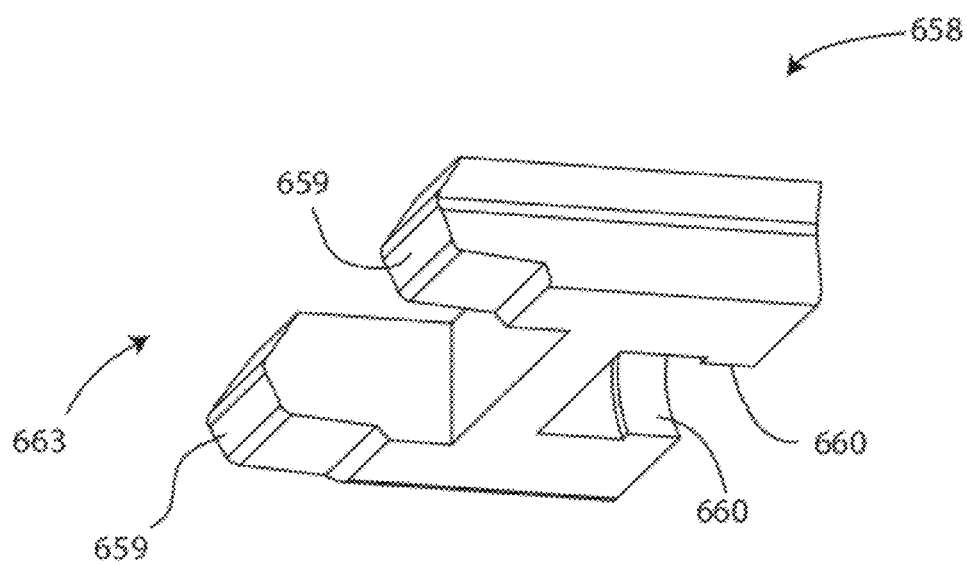
Figure 71B:
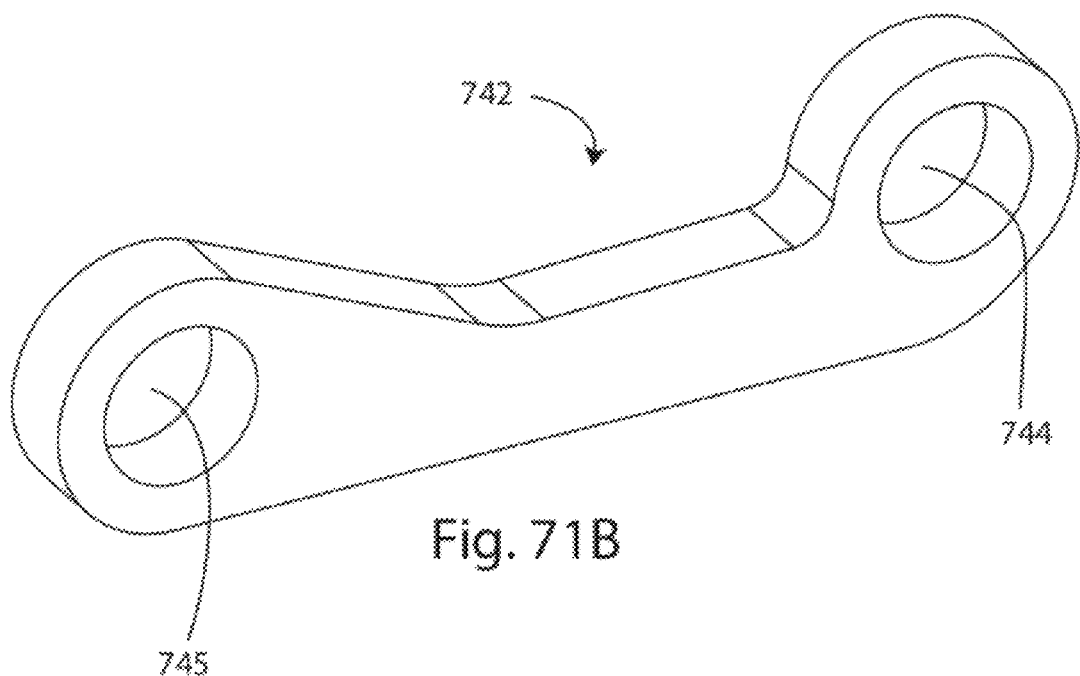

FIG. 71A shows a locking member 658 in accordance with one embodiment of the present disclosure. The locking member 658 may have one or more locking surfaces 663 including one or more locking teeth 659 formed in a surface of the locking member 658 and configured to engage the locking surface 657 of a suitable pivot housing 641, which can also include one or more teeth 645, and or one or more locking member receiver slots 699. The locking member 658 can also have projections 660 configured to interact with retainer members 686 formed on the head portion 627 of the second handle 622 to keep the locking member 658 engaged with the second handle 622.

FIG. 71B shows a portion of an actuator 670 according to another embodiment of the present disclosure. The rigid member 742 can have pin holes 744, 745 configured to receive suitable pivot pins 740, 741 such that the rigid member 742 can be pivotably connected to the second handle 622 and the connector 760, as can be seen in FIGS. 74A-83.

Figure 72A:
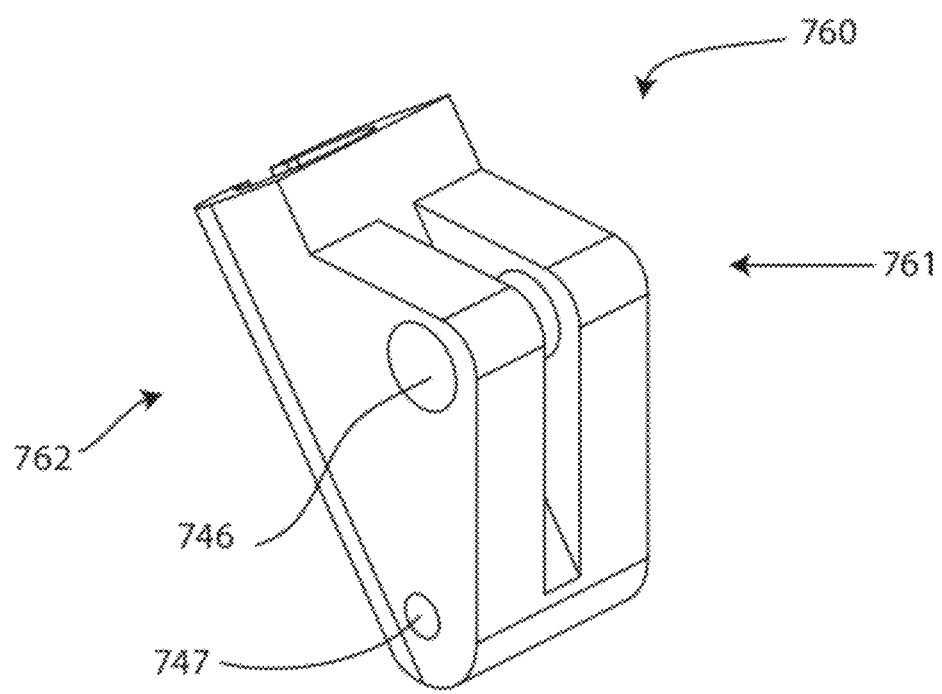
Figure 72B:
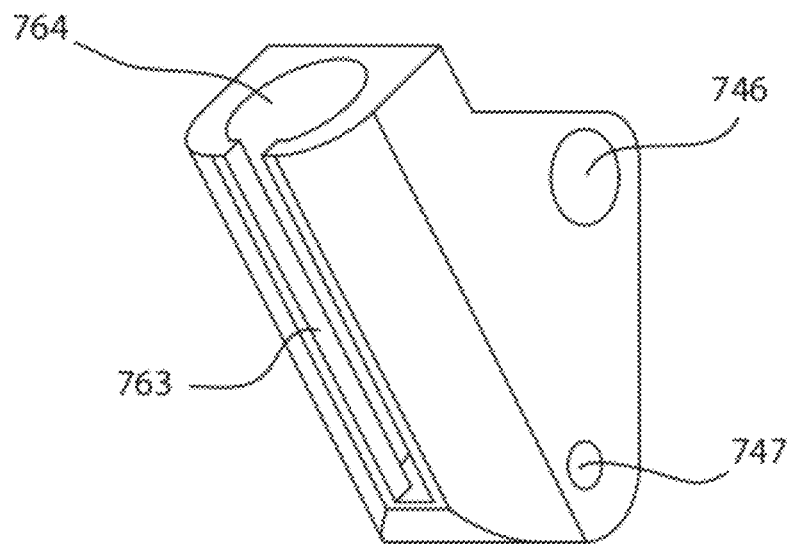
Figure 73A:
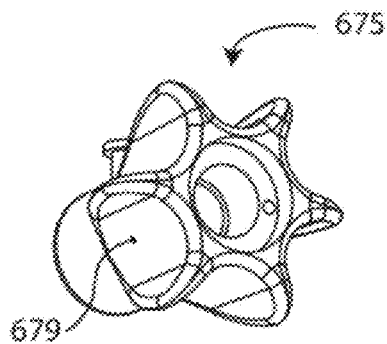
Figure 73B:
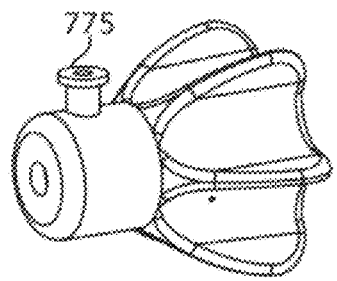
Figure 73C:
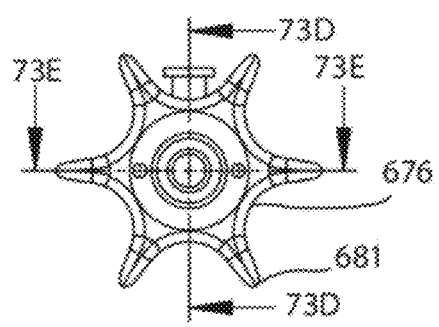
Figure 73D:
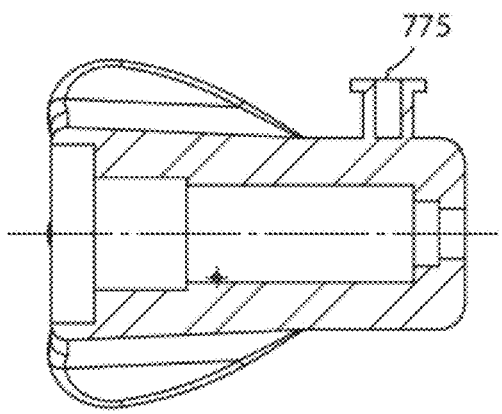
Figure 73E:
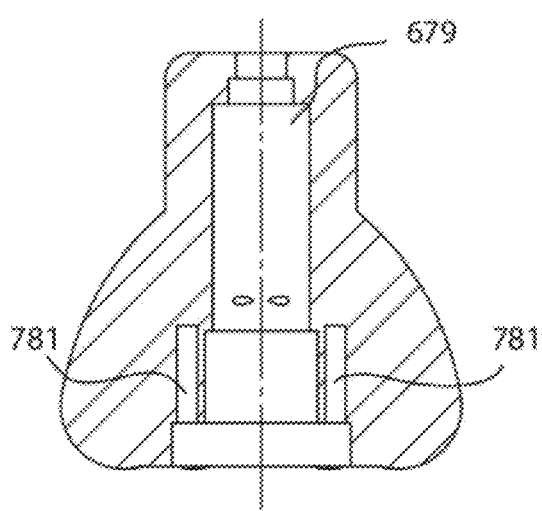

FIGS. 72A-72B illustrate another embodiment of a connector 760 which may be used with the surgical instruments disclosed herein. The connector 760 can have a proximal end 761 and a distal end 762. The proximal end 761 of the connector 760 can have a pin hole 746 configured to receive a suitable pivot pin threaded through the pin hole 745 of the rigid member 742. The distal end 762 of the connector 760 can have a connection aperture 764 in communication with a longitudinal aperture 763 configured to receive the proximal end 751 of a suitable working rod 750.

FIGS. 73A-73E show a rotation knob 675 in accordance with another embodiment of the present disclosure. The rotation knob 675 can have one or more ribs 681 and one or more depressions 676 formed in the outer surface of the rotation knob 675. The rotation knob 675 can also have one or more longitudinal apertures 781 configured to receive springs 782 and spheres 783 therein. The rotation knob 675 may also have a port 775 connected to a surface of the rotation knob 675. The port 775 can be in communication with the inner chamber 679 of the rotation knob 675 and can be used as an aid in the cleaning process. For example, pressurized water can be forced into the port 675 to help clean the inside of the rotation knob 675. The rotation knob 675 can be held in place with a suitable retaining pin (not shown) disposed within aperture 679, similar to other embodiments disclosed herein.

The operation of the actuator 670 between the second handle 622 and the working rod 750 will now be explained with reference to FIGS. 74A-83. Referring to FIG. 75, the actuator 670, including the rigid member 742 and the connector 760, can be used to push or pull the working rod 750. The rigid member 742 can be pivotably engaged with the second handle 622 and pivotably engaged with the connector 760. The connector 760 can also be pivotably engaged with the pivot housing 641 about a pivot pin 759. As the second handle 622 is rotated toward the first handle 602, the rigid member 742 is pulled in the proximal direction causing the connector 760 to pivot in the proximal direction, pulling the working rod 750 in the proximal direction. Conversely, rotating the second handle 622 away from the first handle 602 pushes the rigid member 742 in the distal direction causing the connector 760 to pivot in the distal direction, pushing the working rod 750 in the distal direction.

The distance between the pivot pins 635 and 740, as well as the distance between the pivot pin 635 and the center of force applied to the second handle 622, can be chosen to obtain a desired mechanical advantage applied to the rigid member 742. For example, the distance between the pivot pins 635 and 740 can be chosen to be about 0.25 inches and the distance between the pivot pin 635 and the center of force applied to the second handle 622 can be chosen to be about 2.5 inches. In this embodiment, the ratio of these distances (2.5 inches/0.25 inches) would result in the mechanical advantage of about 10. However, it is to be understood that other distances and ratios can be chosen to obtain other mechanical advantages.

In some embodiments, the location of the pivot pin 741 can be chosen to be substantially coaxial with the pivot pins 664 which control the articulation of the handle section 601 in relation to the working shaft section 674. In one embodiment, the axis of the pivot pin 741 is substantially coaxial with the axis of the pivot pins 664 when the second handle 622 is in the "at rest" position. If the second handle 622 is maintained in the "at rest" position as the handle section 601 is articulated, then the axes of the pivot pins 741 and 664 will substantially stay aligned with each other as the handle section 601 is articulated in the working rod 750 will not substantially move as the handle section 601 is articulated.

In other embodiments, the location of the pivot pin 741 relative to the pivot pins 664 can be chosen such that they are not substantially coaxial with each other. In these embodiments, articulating the handle section 601 can cause the working rod 750 to move, affecting the end effector. In these embodiments, the location of the pivot pin 741 relative to the pivot pins 664 is preferably chosen to minimize movement of the end effector as the handle section 601 is articulated. Accordingly, the movement of the end effector may be small and virtually imperceptible to the surgeon.

In FIGS. 84-97, a surgical instrument 800 in accordance with another embodiment of the present disclosure is illustrated. FIG. 84 shows an isometric view of a surgical instrument 800 having a working shaft section 874 at its distal end, a handle section 801 at its proximal end, and a pivot section 840 intermediate the working shaft section 874 and the handle section 801. The handle section 801 may include a first handle 802 and a second handle 822. FIG. 85 shows a side view of the surgical instrument 800 of FIG. 84 with the handle section 801 adjusted in a "drop-down" position relative to the longitudinal axis 883 of the working shaft section 874, similar to other embodiments disclosed herein. FIG. 86 shows a side view of the surgical instrument 800 of FIG. 84 with the handle section 801 adjusted in an "in-line" position relative to the working shaft section 874. FIG. 87 shows a side view of the surgical instrument 800 of FIG. 84 with the handle section 801 adjusted in an "angled-up" position relative to the working shaft section 874.

FIG. 88 shows an exploded view of the surgical instrument 800. FIGS. 91A-95C illustrate the individual components of FIG. 88 in greater detail. A detailed description of the structure and features for each individual component will be given in a generally proximal to distal direction with reference to FIGS. 91A-95C. A detailed description of how each of the individual components interrelate with one another will then be given, along with the functional relationships between each component. Methods of using the surgical instrument 800 will also be given to illustrate how a surgeon can utilize the surgical instrument 800 to achieve greater ergonomic postures during surgery.

FIGS. 91A-91C show various isometric views of the first handle 802, according to one embodiment of the present disclosure. The first handle 802 has a proximal end 896 and a distal end 897. The first handle 802 can have a top surface 805, a bottom surface 815, and two side surfaces 804. The top surface 805 can have a spatulate shape and/or curve downward in the distal to proximal direction to better conform to the surgeon's palm. In some embodiments, the top surface 805 can have a radius of curvature, or substantially lie along a radius of curvature. In some embodiments, the radius of curvature can be between about 2 and 4 inches. In other embodiments, the radius of curvature can be between about 2.5 inches and 3.5 inches. In a particular embodiment, the radius of curvature is about 2.9 inches.

The top surface 805 of the first handle 802 may have a convex or rounded shape in the lateral direction between the two side surfaces 804 of the first handle 802. The top surface 805 is preferably shaped to be substantially wide enough between the two side surfaces 804 to provide adequate comfort to the surgeon's palm by providing sufficient surface contact area between the top surface 805 and the surgeon's palm to reduce or eliminate "hot spots" from forming on the surgeon's palm. The top surface 805 can have a maximum width and a minimum width in the lateral direction between the two side surfaces. In some embodiments, the minimum width of the top surface is located closer to the distal end of the first handle and the maximum width of the top surface is located closer to the proximal end of the first handle. In other embodiments the minimum width is between about 0.25 inches and about 0.75 inches. In a particular embodiment, the minimum width is about 0.5 inches. In some embodiments, the maximum width is between about 0.5 inches and about 1.25 inches. In one embodiment, the maximum width is about 0.88 inches. The location of the minimum width of the top surface can be chosen to correspond to the area of the top surface 805 that the surgeon's thumb traverses when the surgeon switches between a "finger loop" grip style and a "palm" grip style. Having the minimum width of the top surface in this area of the top surface 805 can allow the surgeon to more easily switch between the "finger loop" grip style and the "palm" grip style because the smaller width makes it easier for the surgeon's thumb to traverse this area of the handle. The side surfaces 804 may include a thumb or finger rest area 808 formed on or into the side surfaces 804 to provide extra support for the surgeon's thumb when engaged along the side surface 804. The first handle 802 may have one or more finger loop holes 810 to receive one or more fingers during procedures requiring greater precision. The finger loop hole contact surface 809 may be convex in shape and wide enough to avoid or eliminate any "hot spots" from occurring on the surgeon's fingers during extended hours of operation. The first handle 802 can have a projection portion 811 at the proximal end 896 of the first handle 802. The projection portion 811 may provide greater surface area to interact with the surgeon's palm against the top surface 805. In some embodiments, the projection portion 811 can include an electrical connector to receive external input.

Any or all of the surfaces of the first handle 802 may include a comfort material (not shown) attached to one or more of the surfaces of the first handle 802, such as a soft rubber, polymer, or silicone. The comfort material may be applied to the first handle 802 after manufacture, or the comfort material may be integrally formed or molded to the first handle 802 during manufacture by any suitable manufacturing processes including, but not limited to, bonding or overmolding.

The distal end 897 of the first handle 802 may include a head portion 812 for receiving a suitably shaped second handle 822 and connector 960 within the opening 925, as will be discussed in more detail below. The head portion 812 can also have lock members 922 configured to interact with complementary shaped lock receivers 923 formed in the pivot housing 841. The first handle 802 can also have a stop pin slot 852 to limit the articulation of a second handle 822 pivotably connected to the first handle 802.

FIGS. 92A-92C show a second handle 822 in accordance with another embodiment of the present disclosure. The second handle 822 can have a top surface 826, a finger loop hole 830, an inner contact surface 829, a projection 832 defining a contact surface 831 and a recess portion 828. The second handle 822 can also have a stop pin hole 803, a pivot pin hole 848, lock members 922, and a working rod slot 926.

FIGS. 93A-93D show a pivot housing 841 in accordance with another embodiment of the present disclosure. The pivot housing 841 can have lock receivers 923 formed in one or more sides and configured to interact with lock members 922 formed in the head portion 812 of the first handle 802. The pivot housing 841 can also have an annular groove 850 configured to receive a retaining pin (not shown) to engage a rotation knob 875.

FIGS. 94A-94B show isometric views of a connector 960 in accordance with the present embodiment. The connector 960 can have lock receivers 923 formed therein, a pivot pin hole 848, a tab 927, and a working rod connector portion 961.

FIGS. 95A-95C show various views of a rotation knob 875 according to another embodiment of the present disclosure. The rotation knob 875 can have ribs 881 and depressions 879 formed therein. The rotation knob 875 can also have a port 975 to aid in cleaning, as discussed previously. The rotation knob and 75 can also have an aperture 979 configured to receive a retaining pin (not shown) to engage the retaining knob 875 to the pivot housing 841. The rotation knob and 75 can also have an inner chamber 879 configured to receive a suitable working rod 950.

The operation of the surgical instrument 800 will now be given with reference to FIGS. 96A-97. Referring to FIG. 97, as the second handle 822 is rotated toward the first handle 802, the working rod connector portion 961 rotates in the proximal direction pulling the working rod 950 in the proximal direction. As the second handle 822 rotates away from the first handle 802, the working rod connector portion 961 rotates in the distal direction pushing the working rod 950 in the distal direction.

Pivoting the handle section 801 relative to the working shaft section 874 will now be explained with reference to FIGS. 88-94B. The biasing spring 998 is disposed between an inner surface of the pivot housing 841 and the first handle 802.

The biasing spring 998 pushes the first handle 802 toward one side of the pivot housing 841 causing the lock members 922 of the second handle 822 to mate with the lock receivers 923 formed in the connector 960 and the lock members 922 of the first handle 802 to mate with the lock receivers 923 formed in the pivot housing 841. Thus, the pivot section 840 is locked in this position. The pivot section 840 can be unlocked by grabbing the handle section 801 and applying a counterforce against the biasing spring 998 to disengage the lock members 922 from the lock receivers 923. The pivot section 840 can then be articulated by maintaining this counterforce and rotating the handle section 801 to the desired location. Once the desired location is obtained, the pivot section 840 can be re-locked by discontinuing the counterforce against the biasing spring 998, causing the handle section 801 to move translationally such that lock members 922 can engage their respective lock receivers 923.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

Certain elements disclosed herein may be interpreted as means for pivoting the handle section relative to the working shaft section for the various surgical instruments disclosed herein. For example, in the various embodiments set forth above the pivoting means may be element 140 as shown in FIG. 1, or element 240 as shown in FIG. 16, or element 440 as shown in FIG. 44, or element 640 as shown in FIG. 60, or element 840 as shown in FIG. 84.

Certain elements disclosed herein may be interpreted as locking means for preventing the handle section from pivoting relative to the working shaft section disclosed herein. For example, in the various embodiments set forth above the locking means may be elements 157 and 163 in FIGS. 8C and 9, or elements 263 and 257 in FIGS. 27 and 30B, or elements 463 and 457 in FIGS. 53B and 54A, or elements 663 and 657 in FIGS. 70A and 71A, or elements 923 and 922 in FIGS. 89B, 90B, 91C, 92B, 93A, and 94A.

Certain elements disclosed herein may be interpreted as means for pivoting the second handle relative to the first handle for the various surgical instruments disclosed herein. For example, in the various embodiments set forth above the second handle pivoting means may be element 135 in FIG. 5, or element 235 in FIG. 21, or element 435 in FIG. 47, or element 635 in FIG. 66, or element 864 in FIG. 88.

Certain elements disclosed herein may be interpreted as actuating means for affecting the end effector. For example, in the various embodiments set forth above the actuating means may be element 170 in FIG. 5, or element 270 in FIG. 21, or elements 470 and 560 in FIG. 47, or elements 742 and 760 in FIG. 66, or element 961 in FIG. 94B.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The term "substantial" or "substantially" means, in general, a deviation from a reference state by an unsatisfactory amount, or a change sufficient to produce an unsatisfactory result. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The invention claimed is:

1. A surgical instrument for improved ergonomic positions, comprising:
   a working shaft section at a distal end of the surgical instrument;
   a first pivot comprising a pivot head portion comprising three distinct slots on the surface of the pivot head portion, the three distinct slots are configured to receive a locking member, wherein the locking member is connected to a handle section;
   a second pivot; and
   the handle section positioned at a proximal end of the surgical instrument comprising a first handle and a second handle, with the handle section pivotable relative to the working shaft section about the first pivot, and wherein the first and second handles are pivotably connected to each other about the second pivot;
   wherein the first handle comprises a button positioned on a top surface of the first handle and a projection portion extending from a proximal end of the first handle, wherein the projection portion comprises a recess portion recessed into the projection portion.

2. The surgical instrument of claim 1, wherein the second pivot is not coaxial with the first pivot.

3. The surgical instrument of claim 2, further comprising an end effector at a distal end of the working shaft section, wherein the end effector remains in a substantially constant functional state as the handle section pivots about the first pivot.

4. The surgical instrument of claim 3, further comprising an actuator engaged with the second handle and the end effector, the actuator configured to actuate the end effector in response to moving the second handle relative to the first handle, wherein the actuator defines an actuation path length between the second handle and the end effector, and wherein the actuation path length remains substantially constant as the handle section pivots relative to the working shaft section through the first pivot such that pivoting the handle section relative to the working shaft section does not affect the end effector.

5. The surgical instrument of claim 2, wherein the first pivot comprises:
   a pivot housing comprising at least one pivot pin hole formed therein;

at least one pivot pin; and at least one pivot pin hole formed in the first handle, wherein the pivot housing is pivotably connected to the first handle about the at least one pivot pin threaded through the at least one pivot pin hole of the first handle and the at least one pivot pin hole of the pivot housing.

6. The surgical instrument of claim 5, wherein the first pivot further comprises:

at least one stop pin slot formed in the pivot housing;

at least one stop pin hole formed in the first handle; and at least one stop pin, wherein the at least one stop pin is threaded through the at least one stop pin hole formed in the first handle and into the at least one stop pin slot formed in the pivot housing, and wherein the size and shape of the at least one stop pin slots is configured to prevent the first handle from pivoting relative to the working shaft section beyond a predetermined angular range in either direction.

7. The surgical instrument of claim 2, wherein the second pivot comprises:

a latch release cavity formed in the second handle;

a second handle pivot pin; and at least one second handle pivot pin hole formed in the first handle, wherein the second handle pivot pin is threaded through the at least one second handle pivot pin hole formed in the first handle and through the latch release cavity formed in the second handle to pivotably connect the second handle relative to the first handle.

8. A method for improved ergonomics during surgery, the method comprising:

providing a surgical instrument for improved ergonomics, the surgical instrument comprising:

a working shaft section at a distal end of the surgical instrument;

a first pivot comprising a pivot head portion comprising three distinct slots on the surface of the pivot head portion, the three distinct slots are configured to receive a locking member, wherein the locking member is connected to a handle section;

a second pivot; and the handle section at a proximal end of the surgical instrument comprising a first handle and a second handle, with the handle section pivotable relative to the working shaft section about the first pivot, and wherein the first and second handles are pivotably connected to each other about the second pivot:, wherein the first handle comprises a button positioned on a top surface of the first handle and a projection portion extending from a proximal end of the first handle, wherein the projection portion comprises a recess portion recessed into the projection portion;

pivoting the handle section relative to the working shaft section about the first pivot; and pivoting the first and second handles relative to each other about the second pivot.

9. The method of claim 8, wherein the second pivot is not coaxial with the first pivot.

10. The method of claim 9, further comprising an end effector at a distal end of the working shaft section, wherein the end effector remains in a substantially constant functional state as the handle section pivots about the first pivot.

11. The method of claim 10, further comprising an actuator engaged with the second handle and the end effector, the actuator configured to actuate the end effector in response to moving the second handle relative to the first handle, wherein the actuator defines an actuation path length between the second handle and the end effector, and wherein the actuation path length remains substantially constant as the handle section pivots relative to the working shaft section through the first pivot.

12. The method of claim 9, wherein the first pivot comprises:

a pivot housing comprising at least one pivot pin hole formed therein;

at least one pivot pin; and at least one pivot pin hole formed in the first handle, wherein the pivot housing is pivotably connected to the first handle about the at least one pivot pin threaded through the at least one pivot pin hole of the first handle and the at least one pivot pin hole of the pivot housing.

13. The method of claim 12, wherein the first pivot further comprises:

at least one stop pin slot formed in the pivot housing;

at least one stop pin hole formed in the first handle; and at least one stop pin, wherein the at least one stop pin is threaded through the at least one stop pin hole formed in the first handle and into the at least one stop pin slot formed in the pivot housing, and wherein the size and shape of the at least one stop pin slots is configured to prevent the first handle from pivoting relative to the working shaft section beyond a predetermined angular range in either direction.

14. A surgical instrument for improved ergonomic positions, comprising:

a working shaft section at a distal end of the surgical instrument;

a first pivoting means;

a second pivoting means; and a handle section at a proximal end of the surgical instrument comprising a first handle and a second handle, with the handle section pivotable relative to the working shaft section about the first pivoting means, and wherein the first and second handles are pivotably connected to each other about the second pivoting means;

wherein the first handle comprises a projection portion extending from a proximal end of the first handle and a recess portion recessed into the projection portion.

15. The surgical instrument of claim 14, wherein the second pivoting means is not coaxial with the first pivoting means.

16. The surgical instrument of claim 15, further comprising an end effector at a distal end of the working shaft section, wherein the end effector remains in a substantially constant functional state as the handle section pivots about the first pivot.

17. A surgical instrument for improved ergonomic positions, comprising:

a working shaft section at a distal end of the surgical instrument;

an end effector at a distal end of the working shaft section;

a handle section at a proximal end of the surgical instrument; and a pivot section intermediate the working shaft section and the handle section, wherein the handle section is pivotable relative to the working shaft section and the end effector remains in a substantially constant functional state as the handle section pivots relative to the working shaft section, wherein the handle section can be selectively positioned in three angled positions relative to the working shaft section;

wherein the pivot section comprises a pivot head portion comprising three distinct slots on the surface of the pivot head portion, the three distinct slots are configured to receive a locking member, wherein the locking member is connected to the handle section.

18. The surgical instrument of claim 17, further comprising a longitudinal axis defined by the working shaft section, a handle section axis, and an angle $\alpha$ a defining an angular relationship between the longitudinal axis and the handle section axis, wherein the handle section can be selectively positioned in an infinite number of angled positions relative to the longitudinal axis of the working shaft section over a range of angles defined by an angle $\alpha_{max}$ and an angle $\alpha_{min}$.

19. The surgical instrument of claim 18, wherein the handle section can be selectively positioned in multiple discrete angled positions $\alpha$ relative to the longitudinal axis of the working shaft section.

20. The surgical instrument of claim 19, wherein the handle section can be selectively positioned in three discrete angled positions $\alpha$ relative to the longitudinal axis of the working shaft section.

21. The surgical instrument of claim 19, wherein the three discrete angled positions $\alpha$ are about −35°, 0°, and 35°.

22. The surgical instrument of claim 18, wherein $\alpha_{max}$ is any number between about 0° and 180° and $\alpha_{min}$ is any number between about 0° and −180°.

23. The surgical instrument of claim 22, wherein $\alpha_{max}$ is any number between about 0° and 90° and $\alpha_{min}$ is any number between about 0° and −90°.

24. A method for improved ergonomics during surgery, the method comprising:
providing a surgical instrument for improved ergonomics, the surgical instrument comprising:
a working shaft section at a distal end of the surgical instrument;
an end effector at a distal end of the working shaft section;
a handle section at a proximal end of the surgical instrument;
a button positioned on a top surface of a first handle of the handle section; and
a pivot section intermediate the working shaft section and the handle section, wherein the pivot section comprises a pivot head portion comprising three distinct slots on the surface of the pivot head portion, the three distinct slots are configured to receive a locking member, wherein the locking member is connected to the handle section; and
pivoting the handle section relative to the working shaft section, wherein the end effector remains in a substantially constant functional state as the handle section pivots, and wherein the handle section can be selectively positioned in at least three angled positions relative to the working shaft section.

25. The method of claim 24, further comprising:
providing the surgical instrument for improved ergonomics, wherein the surgical instrument further comprises:
a longitudinal axis defined by the working shaft section;
a handle section axis; and
an angle $\alpha$ defining an angular relationship between the longitudinal axis and the handle section axis, wherein the handle section can be selectively positioned in an infinite number of angled positions relative to the longitudinal axis of the working shaft section over a range of angles defined by an angle $\alpha_{max}$ and an angle $\alpha_{min}$;
selecting an angle position from the infinite number of angled positions between $\alpha_{max}$ and an angle $\alpha_{min}$; and
pivoting the handle section to the selected angle position.

26. The method of claim 25, wherein $\alpha_{max}$ is any number between about 0° and 180° and $\alpha_{min}$ is any number between about 0° and −180°.

27. The method of claim 24, further comprising:
providing the surgical instrument for improved ergonomics, wherein the surgical instrument further comprises:
a longitudinal axis defined by the working shaft section;
a handle section axis; and
an angle $\alpha$ defining an angular relationship between the longitudinal axis and the handle section axis, wherein the handle section can be selectively positioned in multiple discrete angled positions $\alpha$ relative to the longitudinal axis of the working shaft section;
selecting a discrete angled position $\alpha$ from the multiple discrete angled positions; and
pivoting the handle section to the selected discrete angled position $\alpha$.

28. The method of claim 27, further comprising:
providing the surgical instrument for improved ergonomics, wherein the handle section can be selectively positioned in three discrete angled positions;
selecting one of the three discrete angled positions; and
pivoting the handle section to the selected discrete angled position.

29. The method of claim 27, wherein the three discrete angled positions $\alpha$ are about −35°, 0°, and 35°.

30. A surgical instrument for improved ergonomic positions, comprising:
a working shaft section at a distal end of the surgical instrument;
an end effector at a distal end of the working shaft section; and
a handle section at a proximal end of the surgical instrument, wherein the handle section comprises a first handle having a proximal end, a distal end, two side surfaces, and a top surface, with a projection portion extending from the proximal end of the first handle and a recess portion recessed into the projection portion opposite the top surface, wherein the top surface comprises a button at the distal end of the first handle, wherein the handle section is pivotable relative to the working shaft section, and wherein the end effector remains in a substantially constant functional state as the handle section pivots relative to the working shaft section.

31. The surgical instrument of claim 30, wherein the top surface curves downward in the distal to proximal direction and has a spatulate shape.

32. The surgical instrument of claim 31, wherein the top surface substantially lies along a radius of curvature.

33. The surgical instrument of claim 32, wherein the radius of curvature is between about 2 and 4 inches.

34. The surgical instrument of claim 32, wherein the radius of curvature is between about 2.5 inches and 3.5 inches.

35. The surgical instrument of claim 32, wherein the radius of curvature is about 2.9 inches.

36. The surgical instrument of claim 31, wherein the top surface has a convex or rounded shape in the lateral direction between the two side surfaces.

37. The surgical instrument of claim 31, wherein the top surface has a maximum width and a minimum width in the lateral direction between the two side surfaces.

38. The surgical instrument of claim 37, wherein the minimum width of the top surface is located closer to the distal end of the first handle and the maximum width of the top surface is located closer to the proximal end of the first handle.

39. The surgical instrument of claim 38, wherein the minimum width is between about 0.25 inches and about 0.75 inches.

40. The surgical instrument of claim 38, wherein the maximum width is between about 0.5 inches and about 1.25 inches.

41. The surgical instrument of claim 38, wherein the minimum width is about 0.5 inches and the maximum width is about 0.88 inches.

42. The surgical instrument of claim 31, wherein at least one of the two side surfaces further comprises a thumb or finger rest area.

43. The surgical instrument of claim 31, wherein the first handle further comprises a finger loop.

44. The surgical instrument of claim 30, wherein the first handle further comprises a comfort material.

45. The surgical instrument of claim 44, wherein the comfort material is silicone.

46. The surgical instrument of claim 45, wherein the silicone comfort material is applied to the at least one of the first and second handles by an over-molding manufacturing process.

47. The surgical instrument of claim 30, further comprising a second handle with at least one finger contact surface.

48. The surgical instrument of claim 47, wherein the at least one finger contact surface substantially lies along a radius of curvature.

49. The surgical instrument of claim 48, wherein the radius of curvature is between about 1.5 and 3.5 inches.

50. The surgical instrument of claim 48, wherein the radius of curvature is between about 2 inches and 3 inches.

51. The surgical instrument of claim 48, wherein the radius of curvature is about 2.5 inches.

52. The surgical instrument of claim 48, wherein the second handle further comprises a finger loop having a first finger contact surface configured to receive the ring finger and the middle finger, a projection having a second finger contact surface configured to receive the pinky finger, and a recess portion having a third finger contact surface configured to receive the index finger, wherein the first and second finger contact surfaces substantially lie along a radius of curvature of about 2.5 inches, and wherein the third finger contact surface is offset from the radius of curvature by about 0.0625 inches.

53. A method for improved ergonomics during surgery, the method comprising:
provide a surgical instrument for improved ergonomics, the surgical instrument comprising:
a working shaft section at a distal end of the surgical instrument;
an end effector at a distal end of the working shaft section; and
a handle section at a proximal end of the surgical instrument, wherein the handle section comprises a first handle having a proximal end, a distal end, two side surfaces, and a top surface, with a projection portion extending from the proximal end of the first handle and a recess portion recessed into the projection portion opposite the top surface, wherein the top surface comprises a button at the distal end of the first handle, wherein the handle section is pivotable relative to the working shaft section; and
pivoting the handle section relative to the working shaft section, wherein the end effector remains in a substantially constant functional state as the handle section pivots relative to the working shaft section.

54. The method of claim 53, wherein the top surface curves downward in the distal to proximal direction and has a spatulate shape.

55. The method of claim 54, wherein the top surface substantially lies along a radius of curvature.

56. The method of claim 55, wherein the radius of curvature is between about 2 and 4 inches.

57. The method of claim 55, wherein the radius of curvature is between about 2.5 inches and 3.5 inches.

58. The method of claim 55, wherein the radius of curvature is about 2.9 inches.

59. A surgical instrument for improved ergonomic positions, comprising:
a working shaft section at a distal end of the surgical instrument;
a handle section at a proximal end of the surgical instrument, with the handle section pivotable relative to the working shaft section, wherein the handle section comprises a first handle with a top surface and a projection portion, the projection portion extending from the proximal end of the first handle and a recess portion recessed into the projection portion opposite the top surface; and
a locking mechanism that prevents the handle section from pivoting relative to the working shaft section when the locking mechanism is engaged, and wherein the locking mechanism allows the handle section to pivot relative to the working shaft section when the locking mechanism is not engaged, wherein the locking mechanism is connected to the handle section and engages a pivot housing comprising three distinct slots on the surface of the pivot housing.

60. The surgical instrument of claim 59, wherein the locking mechanism further comprises:
a pivot section comprising the pivot housing comprising a first locking surface; and
a locking member comprising a second locking surface, wherein the first locking surface and the second locking surface are configured to engage with each other in a first state to lock the pivot section and prevent the handle section from pivoting relative to the working shaft section, and wherein the first locking surface and the second locking surface are configured to disengage with each other in a second state to unlock the pivot section and allow the handle section to pivot relative to the working shaft section.

61. The surgical instrument of claim 60, further comprising a longitudinal axis defined by the working shaft section, a handle section axis, and an angle a defining an angular relationship between the longitudinal axis and the handle section axis, wherein the handle section can be selectively positioned in an infinite number of angled positions relative to the longitudinal axis of the working shaft section over a range of angles defined by an angle $\alpha_{max}$ and an angle $\alpha_{min}$ and wherein the first and second locking surfaces are configured to lock at any angled position within the range of angles defined by $\alpha_{max}$ and $\alpha_{min}$.

62. The surgical instrument of claim 61, wherein the handle section can be selectively positioned in multiple discrete angle positions relative to the longitudinal axis of the working shaft section over a range of angles defined by an angle $\alpha_{max}$ and an angle $\alpha_{min}$, and wherein the first and second locking surfaces are configured to lock in the multiple discrete angled positions within the range of angles defined by $\alpha_{max}$ and $\alpha_{min}$.

63. The surgical instrument of claim 62, wherein the first locking surface comprises one or more teeth and the second locking surface comprises one or more teeth configured to engage the one or more teeth of the first locking surface.

64. The surgical instrument of claim 62, wherein the handle section can be selectively positioned in three discrete angled positions relative to the longitudinal axis of the working shaft section, and wherein the first and second locking surfaces are configured to lock in three discrete angled positions.

65. The surgical instrument of claim 64, wherein the first locking surface is the three distinct slots.

66. The surgical instrument of claim 64, wherein the three discrete angled positions are about 35°, 0°, and −35°.

67. The surgical instrument of claim 61, wherein at least one of the first locking surface and the second locking surface comprises a frictional material that allows the first locking surface and the second locking surface to frictionally engage one another at any point and at any angle.

68. A method for improved ergonomics during surgery, the method comprising:
   providing a surgical instrument for improved ergonomics, the surgical instrument comprising:
      a working shaft section at a distal end of the surgical instrument; and
      a handle section at a proximal end of the surgical instrument, with the handle section pivotable relative to the working shaft section, wherein the handle section comprises a first handle with a top surface and a projection portion, the projection portion extending from the proximal end of the first handle and a recess portion recessed into the projection portion opposite the top surface;
      wherein a pivot section comprises a locking mechanism that prevents the handle section from pivoting relative to the working shaft section when the locking mechanism is engaged, and wherein the locking mechanism allows the handle section to pivot relative to the working shaft section when the locking mechanism is not engaged, wherein the locking mechanism is connected to the handle section and engages a pivot housing comprising three distinct slots on a surface of the pivot housing;
   disengaging the locking mechanism to allow the handle section to pivot;
   pivoting the handle section to a desired angle position; and
   engaging the locking mechanism to prevent the handle section from pivoting.

69. The method of claim 68, further comprising:
   providing the surgical instrument for improved ergonomics, wherein the surgical instrument further comprises:
      the pivot section comprising the pivot housing comprising a first locking surface; and
      a locking member comprising a second locking surface, wherein the first locking surface and the second locking surface are configured to engage with each other in a first state to lock the pivot section and prevent the handle section from pivoting relative to the working shaft section, and wherein the first locking surface and the second locking surface are configured to disengage with each other in a second state to unlock the pivot section and allow the handle section to pivot relative to the working shaft section;
   disengaging the first locking surface and the second locking surface in the second state;
   pivoting the handle section to a desired angle position; and
   engaging the first locking surface and the second locking surface in the first state.

70. The method of claim 69, wherein the handle section can be selectively positioned in multiple discrete angle positions relative to the longitudinal axis of the working shaft section, and wherein the first and second locking surfaces are configured to lock in the multiple discrete angled positions.

71. The method of claim 70, wherein the first locking surface comprises one or more teeth and the second locking surface comprises one or more teeth configured to engage the one or more teeth of the first locking surface.

72. The method of claim 70, wherein the handle section can be selectively positioned in three discrete angled positions relative to the longitudinal axis of the working shaft section, and wherein the first and second locking surfaces are configured to lock in three discrete angled positions.

73. A surgical instrument for improved ergonomic positions, comprising:
   a working shaft section at a distal end of the surgical instrument;
   an end effector at a distal end of the working shaft section;
   a handle section at a proximal end of the surgical instrument, wherein the handle section comprises a first handle and a second handle;
   a pivot section intermediate the handle section and the working shaft section, wherein the handle section is pivotable relative to the working shaft section about the pivot section, wherein the pivot section comprises a pivot head portion comprising three distinct slots on the surface of the pivot head portion, the three distinct slots are configured to receive a locking member, wherein the locking member is connected to the handle section; and
   an actuator comprising a proximal end and a distal end, wherein the proximal end of the actuator is engaged with at least one of the first and second handles and the distal end of the actuator is coupled to the end effector such that moving the first and second handles relative to each other causes the actuator to affect the end effector.

74. The surgical instrument of claim 73, wherein the actuator comprises an elongated flexible member having a proximal end and a distal end, and wherein the proximal end of the elongated flexible member engages the second handle and the distal end of the elongated flexible member engages the end effector.

75. The surgical instrument of claim 74, wherein the elongated flexible member is a cable that can flex or bend laterally while substantially resisting longitudinal tension forces.

76. The surgical instrument of claim 75, wherein the pivot section further comprises a pivot pin with a guide hole formed through the pivot pin, the guide hole being configured to receive the cable therethrough and to substantially retain the cable along the centerline of the pivot section as the handle section articulates with respect to the working shaft section.

77. The surgical instrument of claim 76, further comprising a tension member configured to apply a substantially constant tension force to the cable.

78. The surgical instrument of claim 77, wherein the tension member is a spring.

79. The surgical instrument of claim 73, wherein the actuator comprises two rigid portions connected by a flexible portion disposed between the two rigid portions, wherein the two rigid portions connected by the flexible portion substantially resist tension and compression forces applied in the longitudinal direction and allow the two rigid portions to articulate with respect to each other, so that the actuator can transmit tension and compression forces to the end effector while allowing the handle section to pivot.

80. The surgical instrument of claim 73, further comprising a working rod having a proximal end and a distal end, wherein the proximal end of the working rod is engaged with the distal end of the actuator, and wherein the distal end of the working rod is engaged with the end effector.

81. The surgical instrument of claim 73, wherein the actuator comprises:
- a first rigid portion;
- a second rigid portion;
- a first actuator pivot;
- a second actuator pivot; and
- a third actuator pivot, wherein the first actuator pivot engages the first rigid portion with the second handle, the second actuator pivot engages the first rigid portion with the second rigid portion, and wherein the third actuator pivot engages the second rigid portion to a stationary member.

82. The surgical instrument of claim 81, wherein the second actuator pivot is substantially coaxial with the pivot section for at least one positional relationship between the first handle and the second handle.

83. The surgical instrument of claim 81, wherein a mechanical advantage acting on the second rigid portion, through the first rigid portion, corresponds to a ratio of about 10.

84. A method for improved ergonomics during surgery, the method comprising:
providing a surgical instrument for improved ergonomics, the surgical instrument comprising:
- a working shaft section at a distal end of the surgical instrument;
- an end effector at a distal end of the working shaft section;
- a handle section at a proximal end of the surgical instrument, with a projection portion extending from the proximal end of the first handle and a recess portion recessed into the projection portion opposite the top surface, wherein the top surface comprises a button at the distal end of the first handle, with the handle section pivotable relative to the working shaft section about a pivot, and wherein the handle section comprises a first handle and a second handle; and
- an actuator comprising a proximal end and a distal end, wherein the proximal end of the actuator is engaged with at least one of the first and second handles and the distal end of the actuator is coupled to the end effector such that moving the first and second handles relative to each other causes the actuator to affect the end effector;

moving the first and second handles relative to each other to cause the actuator to affect the end effector.

85. The method of claim 84, wherein the actuator comprises an elongated flexible member having a proximal end and a distal end, and wherein the proximal end of the elongated flexible member engages the second handle and the distal end of the elongated flexible member engages the end effector.

86. The method of claim of claim 85, wherein the elongated flexible member is a cable that can flex or bend laterally while substantially resisting longitudinal tension forces.

87. The method of claim of claim 86, wherein the pivot further comprises a pivot pin with a guide hole formed through the pivot pin, the guide hole being configured to receive the cable therethrough and to substantially retain the cable along the centerline of the pivot as the handle section articulates with respect to the working shaft section.

88. The method of claim of claim 87, further comprising a tension member configured to apply a substantially constant tension force to the cable.

* * * * *